United States Patent
Lajoie et al.

(10) Patent No.: US 9,688,994 B2
(45) Date of Patent: Jun. 27, 2017

(54) METHODS OF INTRODUCING NUCLEIC ACIDS INTO CELLULAR DNA

(71) Applicant: President and Fellows of Harvard College, Cambridge, MA (US)

(72) Inventors: Marc J. Lajoie, Cambridge, MA (US); Christopher J. Gregg, Roslindale, MA (US); Joshua A. Mosberg, Cambridge, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/954,351

(22) Filed: Jul. 30, 2013

(65) Prior Publication Data

US 2014/0045267 A1 Feb. 13, 2014

Related U.S. Application Data

(60) Provisional application No. 61/677,375, filed on Jul. 30, 2012.

(51) Int. Cl.
*C12N 15/70* (2006.01)
*C12N 15/10* (2006.01)

(52) U.S. Cl.
CPC ........... *C12N 15/70* (2013.01); *C12N 15/102* (2013.01); *C12N 15/1024* (2013.01)

(58) Field of Classification Search
None
See application file for complete search history.

(56) References Cited

U.S. PATENT DOCUMENTS 8,153,432 B2   4/2012   Church et al.

OTHER PUBLICATIONS

Grompe et al., Journal of Bacteriology, 1991, vol. 173, pp. 1268-1278.*
Britton et al., Journal of Bacteriology, 1997, vol. 179, pp. 4575-4582.*
Ivessa et al., Cell, 2000, vol. 100, pp. 479-489.*
Zieg et al., Journal of Bacteriology, vol. 134, pp. 958-966, 1978.*
Michel et al., PNAS, 2001, vol. 98, pp. 8181-8188.*
Lao-Sirieix et al., TRENDS in Genetics, 2005, vol. 21, pp. 568-572.*
Asai, et al. (1994) D-loops and R-loops: alternative mechanisms for the initiation of chromosome replication in *Escherichia coli*. Journal of Bacteriology, 176, 1807-1812.
Blomfield, et al. (1991), Allelic exchange in *Escherichia coli* using the Bacillus subtilis sacB gene and a temperature-sensitive pSC101 replicon, Mol. Microbiol., 5, 1447-1457.

Carr, et al. (2012) Enhanced Multiplex Genome Engineering through Cooperative Oligonucleotide Co-selection. Nucleic Acids Res., 1-11.
Corn, et al. (2006) Regulation of bacterial priming and daughter strand synthesis through helicase-primase interactions. Nucleic Acids Res., 34, 4082-4088.
Costantino, et al. (2003) Enhanced levels of lambda Red-mediated recombinants in mismatch repair mutants. Proc Natl Acad Sci U S A, 100, 15748-15753.
DeVito, J.A. (2008) Recombineering with tolC as a selectable/counter-selectable marker: remodeling the rRNA operons of *Escherichia coli*. Nucleic Acids Res, 36, e4.
Ellis, et al. 2001, High efficiency mutagenesis, repair, and engineering of chromosomal DNA using single-stranded oligonucleotides, Proc. Natl. Acad. Sci. U. S. A., 98, 6742-6746.
Erler, et al. (2009) Conformational Adaptability of Red beta during DNA Annealing and Implications for Its Structural Relationship with Rad52. J. Mol. Biol., 391, 586-598.
Gibson, et al. (2010) Creation of a Bacterial Cell Controlled by a Chemically Synthesized Genome. Science, 329, 52-56.
Isaacs, et al. 2011, Precise manipulation of chromosomes in vivo enables genome-wide codon replacement, Science, 333, 348-353.
Li, et al. (2003) Identification of factors influencing strand bias in oligonucleotide-mediated recombination in *Escherichia coli*. Nucleic Acids Res, 31, 6674-6687.
Lia, et al. (2012) Polymerase Exchange During Okazaki Fragment Synthesis Observed in Living Cells. Science, 335, 328-331.
Maresca, et al. (2010), Single-stranded heteroduplex intermediates in lambda Red homologous recombination, BMC Mol. Biol., 11.
Mosberg, et al. (2010) Lambda Red Recombineering in *Escherichia coli* Occurs Through a Fully Single-Stranded Intermediate. Genetics, 186, 791-799.
Nakayama, et al. (2005) Improvement of recombination efficiency by mutation of Red proteins. Biotechniques, 38, 917-924.
Oakley, et al. (2005) Crystal and Solution Structures of the Helicase-binding Domain of *Escherichia coli* Primase. Journal of Biological Chemistry, 280, 11495-11504.
Okazaki, R., et al. (1968), Mechanism of DNA chain growth. I. Possible discontinuity and unusual secondary structure of newly synthesized chains, Proceedings of the National Academy of Sciences, 59, 598-605.
Posfai, et al. (2006) Emergent properties of reduced-genome *Escherichia coli*. Science, 312, 1044-1046.
Rybalchenko, et al. (2004) Strand invasion promoted by recombination protein ? of coliphage ?. Proc. Natl. Acad. Sci. U. S. A., 101, 17056-17060.
Smith, et al. (2003) Generating a synthetic genome by whole genome assembly: phi X174 bacteriophage from synthetic oligonucleotides. Proc. Natl. Acad. Sci. U. S. A., 100, 15440-15445.
Tanner, et al. (2008) Single-molecule studies of fork dynamics in *Escherichia coli* DNA replication. Nat Struct Mol Biol, 15, 170-176.

(Continued)

*Primary Examiner* — Mindy G Brown
(74) *Attorney, Agent, or Firm* — Banner & Witcoff, Ltd.

(57) ABSTRACT

A method of introducing a nucleic acid sequence into a cell is provided where the cell has impaired or inhibited or disrupted DnaG primase activity or impaired or inhibited or disrupted DnaB helicase activity, or larger or increased gaps or distance between Okazaki fragments or lowered or reduced frequency of Okazaki fragment initiation, or the cell has increased single stranded DNA (ssDNA) on the lagging strand of the replication fork including transforming the cell through recombination with a nucleic acid oligomer.

18 Claims, 7 Drawing Sheets
(7 of 7 Drawing Sheet(s) Filed in Color)

(56) References Cited

OTHER PUBLICATIONS

Tashiro, et al. (2011) A nucleoside kinase as a dual selector for genetic switches and circuits. Nucleic Acids Res., 39, e12.

Tougu, et al. (1996) The Extreme C Terminus of Primase is Required for Interaction with DnaB at the Replication Fork. Journal of Biological Chemistry, 271, 21391-21397.

Tougu, et al. (1996) The Interaction between Helicase and Primase Sets the Replication Fork Clock. Journal of Biological Chemistry, 271, 21398-21405.

Wang, et al. (2009), Programming cells by multiplex genome engineering and accelerated evolution, Nature, 460, 894-898.

Wang, et al. (2011) Modified bases enable high-efficiency oligonucleotide-mediated allelic replacement via mismatch repair evasion. Nucleic Acids Res, 39, 7336-7347.

Wang, et al. (2011) Multiplexed genome engineering and genotyping methods: Applications for Synthetic Biology and Metabolic Engineering. Methods in Enzymology, vol. 48:409-426.

Wang, et al. (2012) Genome-scale promoter engineering by coselection MAGE. Nat Meth, 9, 591-593.

Warming, et al. (2005) Simple and highly efficient BAC recombineering using galK selection, Nucleic Acids Res., 33, e36.

Yao, et al. (2009) Single-molecule analysis reveals that the lagging strand increases replisome processivity but slows replication fork progression. Proceedings of the National Academy of Sciences, 106, 13236-13241.

Zechner, et al. (1992) Coordinated leading- and lagging-strand synthesis at the *Escherichia coli* DNA replication fork. II. Frequency of primer synthesis and efficiency of primer utilization control Okazaki fragment size. Journal of Biological Chemistry, 267, 4045-4053.

\* cited by examiner

METHODS OF INTRODUCING NUCLEIC ACIDS INTO CELLULAR DNA

RELATED APPLICATIONS

This application claims priority from U.S. provisional patent application No. 61/677,375, filed Jul. 30, 2012 and is hereby incorporated herein by reference in its entirety for all purposes.

STATEMENT OF GOVERNMENT INTERESTS

This invention was made with government support under Department of Energy Genomes to Life Center grant number DE-FG02-02ER63445 and National Institutes of Health grant number P50 HG005550. The Government has certain rights in the invention.

FIELD

The present invention relates in general to methods of introducing multiple nucleic acid sequences into one or more target cells.

BACKGROUND

High throughput genome engineering has been used to create organisms with designed genomes. See Smith, H. O., Hutchison, C. A., Pfannkoch, C. and Venter, J. C. (2003), Generating a synthetic genome by whole genome assembly: phi X174 bacteriophage from synthetic oligonucleotides, Proc. Natl. Acad. Sci. U.S.A., 100, 15440-15445 and Gibson, D. G., Glass, J. I., Lartigue, C., Noskov, V. N., Chuang, R. Y., Algire, M. A., Benders, G. A., Montague, M. G., Ma, L., Moodie, M. M. et al. (2010), Creation of a Bacterial Cell Controlled by a Chemically Synthesized Genome, Science, 329, 52-56. Certain methods of genome engineering involving recombination are known. See Wang, H. H., Isaacs, F. J., Carr, P. A., Sun, Z. Z., Xu, G., Forest, C. R. and Church, G. M. (2009), Programming cells by multipleX genome engineering and accelerated evolution, Nature, 460, 894-898; U.S. Pat. No. 8,153,432; See Can, P. A., Wang, H. H., Sterling, B., Isaacs, F. J., Lajoie, M. J., Xu, G., Church, G. M. and Jacobson, J. M. (2012), Enhanced MultipleX Genome Engineering through Cooperative Oligonucleotide Co-selection. Nucleic Acids Res., 1-11; Zechner et al., Coordinated leading- and lagging-strand synthesis at the E. Coli DNA replication fork. II. Frequency of primer synthesis and efficiency of primer utilization control of Okazaki fragment size, *Journal of Biological Chemistry*, 267, 4045-4053 (1992). See Wang, H. H., Kim, H., Cong, L., Jeong, J., Bang, D. and Church, G. M. (2012), Genome-scale promoter engineering by coselection MAGE, Nat Meth, 9, 591-593. Such methods typically involve introducing eXogenous DNA into the genomes of dividing cells. Such methods can utilize phage λ Redβ recombinase, which binds to ssDNA oligos, protecting them from ssDNA eXonucleases, and facilitating their annealing to the lagging strand of the replication fork. See Ellis, H. M., Yu, D. G., DiTizio, T. and Court, D. L. (2001), High efficiency mutagenesis, repair, and engineering of chromosomal DNA using single-stranded oligonucleotides, Proc. Natl. Acad. Sci. U.S.A., 98, 6742-6746. Generating a heterogenic population has been harnessed for directed evolution of biosynthetic pathways and eXtensive cycling toward isogenic populations has been used to remove all 314 TAG stop codons in subsets across 32 E. coli strains. See Isaacs, F. J., Carr, P. A., Wang, H. H., Lajoie, M. J., Sterling, B., Kraal, L., Tolonen, A. C., Gianoulis, T. A., Goodman, D. B., Reppas, N. B. et al. (2011), Precise manipulation of chromosomes in vivo enables genome-wide codon replacement, Science, 333, 348-353.

Several approaches are known for improving introduction of eXogenous nucleic acids into the genome of a cell such as targeting oligos to the lagging strand of the replication fork, See Li, X. T., Costantino, N., Lu, L. Y., Liu, D. P., Watt, R. M., Cheah, K. S., Court, D. L. and Huang, J. D. (2003), Identification of factors influencing strand bias in oligonucleotide-mediated recombination in *Escherichia coli*, Nucleic Acids Res, 31, 6674-6687, evading mismatch repair using modified nucleotides, See Wang, H. H., Xu, G., Vonner, A. J. and Church, G. M. (2011), Modified bases enable high-efficiency oligonucleotide-mediated allelic replacement via mismatch repair evasion, Nucleic Acids Res, 39, 7336-7347, minimizing oligo secondary structure and optimizing homology lengths, blocking oligo degradation with 5' phosphorothioate bonds, avoiding sequences with high degrees of off-target homology elsewhere in the genome, and removing the mismatch repair protein MutS to avoid reversion of mutated alleles. See Costantino, N. and Court, D. L. (2003), Enhanced levels of lambda Red-mediated recombinants in mismatch repair mutants, Proc Natl Acad Sci USA, 100, 15748-15753.

Okazaki Fragment (OF) size can be modulated by the frequency of OF primer synthesis by DnaG primase. Tougu et al. have reported E. coli primase variants with impaired helicase binding, resulting in less-frequent OF initiation, but normal replication fork rate, priming efficiency, and primer utilization during in vitro replication. These variants, K580A and Q576A, resulted in in vitro OFs that were approXimately 1.5- and 8-fold longer (respectively) than those initiated by wild type (wt) DnaG. See Tougu, K. and Marians, K. J. (1996), The EXtreme C Terminus of Primase Is Required for Interaction with DnaB at the Replication Fork, Journal of Biological Chemistry, 271, 21391-21397.

SUMMARY

Embodiments of the present disclosure are directed to methods for introducing one or more eXogenous nucleic acids into the DNA or genome of a cell where the cell has impaired or inhibited or disrupted primase activity or impaired or inhibited or disrupted helicase activity. Embodiments of the present disclosure are directed to methods for introducing one or more eXogenous nucleic acids into the DNA or genome of a cell which has been genetically altered to impair or inhibit or disrupt primase activity or impair or inhibit or disrupt helicase activity.

Embodiments of the present disclosure are directed to methods for introducing a plurality of eXogenous nucleic acids into the DNA of a cell where the cell has impaired or inhibited or disrupted primase activity or impaired or inhibited or disrupted helicase activity. Embodiments of the present disclosure are directed to methods for introducing one or more eXogenous nucleic acids into the DNA of a cell through recombination where the cell has impaired or inhibited or disrupted primase activity or impaired or inhibited or disrupted helicase activity. Embodiments of the present disclosure are directed to methods for introducing a plurality of nucleic acids into the DNA of a cell through recombination where the cell has impaired or inhibited or disrupted primase activity or impaired or inhibited or disrupted helicase activity.

Embodiments of the present disclosure include methods of disrupting interaction between primase and helicase in a cell while introducing one or more or a plurality of eXogenous nucleic acids into the DNA of the cell. According to certain aspects, disrupting the interaction between primase and helicase increases accessible eXogenous ssDNA on a lagging strand of a replication fork in the cell. According to certain aspects, disrupting the interaction between primase and helicase increases accessible eXogenous ssDNA on a lagging strand of a replication fork in the cell and increases allele replacement frequencies in transformation or transfection methods described herein.

According to one aspect, multiple nucleic acid sequences are introduced by recombination into a plurality of cells using a multipleX method where a plurality of cells in a vessel receive multiple nucleic acids into their genomes through recombination and where the cells have impaired or inhibited or disrupted primase activity or impaired or inhibited or disrupted helicase activity. The cells can then be the subject of further recombination of one or more eXogenous nucleic acid sequences into their genomes, for eXample, by cyclic addition of eXogenous nucleic acids into cells in parallel, i.e. multiple cells being subjected to recombination in a vessel. The addition of one or more nucleic acids can be random or in a specific order or location within the genome. The addition of one or more nucleic acids can be with or without use of one or more selectable markers.

Accordingly, embodiments of the present disclosure are directed to a method including introducing one or more or a plurality of nucleic acid sequences (such as eXogenous sequences) into a cell having impaired or inhibited or disrupted primase activity or impaired or inhibited or disrupted helicase activity. Embodiments of the present disclosure are also directed to a method including transforming or transfecting a cell having impaired or inhibited or disrupted primase activity or impaired or inhibited or disrupted helicase activity with one or more or a plurality of nucleic acid sequences. According to certain aspects, a transformed or transfected cell having impaired or inhibited or disrupted primase activity or impaired or inhibited or disrupted helicase activity which has one or more or a plurality of nucleic acid sequences inserted into its genome (for eXample by a process referred to as recombination), may be further transformed or transfected one or more times resulting in a cell having multiple eXogeneous nucleic acid sequences in its genome.

According to one aspect, a method is provided including transforming or transfecting a cell having impaired or inhibited or disrupted primase activity or impaired or inhibited or disrupted helicase activity using transformation medium or transfection medium including at least one nucleic acid oligomer, replacing the transformation medium or transfection medium with growth medium, incubating the cell in the growth medium, and repeating the steps of transforming or transfecting and incubating the cell in growth medium until multiple nucleic acid sequences have been introduced into the cell. In certain aspects, a pool of nucleic acid oligomers is added to the cell having impaired or inhibited or disrupted primase activity or impaired or inhibited or disrupted helicase activity in the transformation or transfection step. In other aspects, an oligomer is single-stranded DNA. In other aspects, multiple mutations are generated in a chromosome or in a genome. In still other aspects, the growth medium contains an antibiotic, and/or the growth medium is minimal medium. In certain other aspects, a plurality of cells having impaired or inhibited or disrupted primase activity or impaired or inhibited or disrupted helicase activity is contacted with a nucleic acid oligomer in the transformation or transfection step. In certain other aspects, a plurality of cells having impaired or inhibited or disrupted primase activity or impaired or inhibited or disrupted helicase activity is contacted with a plurality of nucleic acid oligomers in the transformation or transfection step. In certain other aspects, the cell or cells may be contained within a vessel such as a microfuge tube, a test tube, a cuvette, a multi-well plate, a microfiber, a flow system or other structures or systems known to those of skill in the art for carrying out the transformation or transfection of cells. According to certain aspects, the method may be automated.

According to one aspect, a cell having impaired or inhibited or disrupted primase activity is understood to mean that the primase activity in the cell is below that normally present in a wild type cell of the same type. According to one aspect, a cell having impaired or inhibited or disrupted primase activity is understood to mean that the primase has a diminished interaction with helicase. According to one aspect, a cell can be genetically modified to impair, inhibit or disrupt primase activity directly or indirectly. According to one aspect, the cell may still eXhibit primase activity, but the primase activity has been impaired, inhibited or disrupted compared to a wild type cell of the same type.

According to one aspect, a cell having impaired or inhibited or disrupted helicase activity is understood to mean that the helicase activity in the cell is below that normally present in a wild type cell of the same type. According to one aspect, a cell having impaired or inhibited or disrupted helicase activity is understood to mean that the helicase has a diminished interaction with primase. According to one aspect, a cell can be genetically modified to impair, inhibit or disrupt helicase activity directly or indirectly. According to one aspect, the cell may still eXhibit helicase activity, but the helicase activity has been impaired, inhibited or disrupted compared to a wild type cell of the same type.

Embodiments of the present disclosure are directed to methods for introducing one or more eXogenous nucleic acids into the DNA or genome of a cell where the cell has increased single stranded DNA (ssDNA) on the lagging strand of the replication fork. Embodiments of the present disclosure are directed to methods for introducing one or more eXogenous nucleic acids into the DNA or genome of a cell which has been genetically altered to increase single stranded DNA (ssDNA) on the lagging strand of the replication fork.

According to one aspect, a cell having increased single stranded DNA (ssDNA) on the lagging strand of the replication fork is understood to mean that the amount or frequency of single stranded DNA (ssDNA) on the lagging strand of the replication fork is above that normally present in a wild type cell of the same type. According to one aspect, a cell can be genetically modified to increase single stranded DNA (ssDNA) on the lagging strand of the replication fork.

Embodiments of the present disclosure are directed to methods for introducing a plurality of eXogenous nucleic acids into the DNA of a cell where the cell has increased single stranded DNA (ssDNA) on the lagging strand of the replication fork or has been genetically altered to increase single stranded DNA (ssDNA) on the lagging strand of the replication fork. Embodiments of the present disclosure are directed to methods for introducing one or more eXogenous nucleic acids into the DNA of a cell through recombination where the cell has increased single stranded DNA (ssDNA) on the lagging strand of the replication fork or has been genetically altered to increase single stranded DNA (ssDNA) on the lagging strand of the replication fork. Embodiments of the present disclosure are directed to methods for introducing a plurality of nucleic acids into the DNA of a cell through recombination where the cell has increased single stranded DNA (ssDNA) on the lagging strand of the replication fork or has been genetically altered to increase single stranded DNA (ssDNA) on the lagging strand of the replication fork.

Embodiments of the present disclosure include methods of increasing single stranded DNA (ssDNA) on the lagging strand of the replication fork or genetically altering a cell to increase single stranded DNA (ssDNA) on the lagging strand of the replication fork while introducing one or more or a plurality of eXogenous nucleic acids into the DNA of the cell. According to certain aspects, disrupting the interaction between primase and helicase such as by genetically altering a cell to impair or inhibit primase activity or impair or inhibit helicase activity or both increases accessible eXogenous ssDNA on a lagging strand of a replication fork in the cell. According to certain aspects, disrupting the interaction between primase and helicase increases accessible eXogenous ssDNA on a lagging strand of a replication fork in the cell and increases allele replacement frequencies in transformation or transfection methods described herein.

According to one aspect, multiple nucleic acid sequences are introduced by recombination into a plurality of cells using a multipleX method where a plurality of cells in a vessel receive multiple nucleic acids into their genomes through recombination and where the cells have increased single stranded DNA (ssDNA) on the lagging strand of the replication fork or have been genetically altered to increase single stranded DNA (ssDNA) on the lagging strand of the replication fork. The cells can then be the subject of further recombination of one or more eXogenous nucleic acid sequences into their genomes, for eXample, by cyclic addition of eXogenous nucleic acids into cells in parallel, i.e. multiple cells being subjected to recombination in a vessel. The addition of one or more nucleic acids can be random or in a specific order or location within the genome. The addition of one or more nucleic acids can be with or without use of one or more selectable markers.

Accordingly, embodiments of the present disclosure are directed to a method including introducing one or more or a plurality of nucleic acid sequences (such as eXogenous sequences) into a cell having increased single stranded DNA (ssDNA) on the lagging strand of the replication fork or having been genetically altered to increase single stranded DNA (ssDNA) on the lagging strand of the replication fork. Embodiments of the present disclosure are also directed to a method including transforming or transfecting a cell having increased single stranded DNA (ssDNA) on the lagging strand of the replication fork or having been genetically altered to increase single stranded DNA (ssDNA) on the lagging strand of the replication fork with one or more or a plurality of nucleic acid sequences. According to certain aspects, a transformed or transfected cell having increased single stranded DNA (ssDNA) on the lagging strand of the replication fork or having been genetically altered to increase single stranded DNA (ssDNA) on the lagging strand of the replication fork which has one or more or a plurality of nucleic acid sequences inserted into its genome (for eXample by a process referred to as recombination), may be further transformed or transfected one or more times resulting in a cell having multiple eXogeneous nucleic acid sequences in its genome.

According to one aspect, a method is provided including transforming or transfecting a cell having increased single stranded DNA (ssDNA) on the lagging strand of the replication fork or having been genetically altered to increase single stranded DNA (ssDNA) on the lagging strand of the replication fork using transformation medium or transfection medium including at least one nucleic acid oligomer, replacing the transformation medium or transfection medium with growth medium, incubating the cell in the growth medium, and repeating the steps of transforming or transfecting and incubating the cell in growth medium until multiple nucleic acid sequences have been introduced into the cell. In certain aspects, a pool of nucleic acid oligomers is added to the cell having increased single stranded DNA (ssDNA) on the lagging strand of the replication fork or having been genetically altered to increase single stranded DNA (ssDNA) on the lagging strand of the replication fork in the transformation or transfection step. In other aspects, an oligomer is single-stranded DNA. In other aspects, multiple mutations are generated in a chromosome or in a genome. In still other aspects, the growth medium contains an antibiotic, and/or the growth medium is minimal medium. In certain other aspects, a plurality of cells having increased single stranded DNA (ssDNA) on the lagging strand of the replication fork or having been genetically altered to increase single stranded DNA (ssDNA) on the lagging strand of the replication fork is contacted with a nucleic acid oligomer in the transformation or transfection step. In certain other aspects, a plurality of cells having increased single stranded DNA (ssDNA) on the lagging strand of the replication fork or having been genetically altered to increase single stranded DNA (ssDNA) on the lagging strand of the replication fork is contacted with a plurality of nucleic acid oligomers in the transformation or transfection step. In certain other aspects, the cell or cells may be contained within a vessel such as a microfuge tube, a test tube, a cuvette, a multi-well plate, a microfiber, a flow system or other structures or systems known to those of skill in the art for carrying out the transformation or transfection of cells. According to certain aspects, the method may be automated.

Embodiments of the present disclosure are directed to methods for introducing one or more eXogenous nucleic acids into the DNA or genome of a cell modified to increase distance between Okazaki fragments, such as nascent Okazaki fragments, or lower or reduce frequency of Okazaki fragment initiation. Embodiments of the present disclosure are directed to methods for introducing one or more eXogenous nucleic acids into the DNA or genome of a cell which has been genetically altered to increase distance between Okazaki fragments or lower or reduce frequency of Okazaki fragment initiation.

According to one aspect, a cell having increased distance between Okazaki fragments is understood to mean that the gaps or distance between Okazaki fragments is above that normally present in a wild type cell of the same type. According to one aspect, a cell can be genetically modified to increase gaps or distance between Okazaki fragments.

According to one aspect, a cell having lowered or reduced frequency of Okazaki fragment initiation is understood to mean that the frequency of Okazaki fragment initiation is below that normally present in a wild type cell of the same type. According to one aspect, a cell can be genetically modified to reduce or lower frequency of Okazaki fragment initiation.

Embodiments of the present disclosure are directed to methods for introducing a plurality of eXogenous nucleic acids into the DNA of a cell where the cell eXhibits larger or increased gaps or increased distance between Okazaki fragments or lowered or reduced frequency of Okazaki fragment initiation. Embodiments of the present disclosure are directed to methods for introducing one or more eXogenous nucleic acids into the DNA of a cell through recombination where the cell has increased distance between Okazaki fragments or lowered or reduced frequency of Okazaki fragment initiation. Embodiments of the present disclosure are directed to methods for introducing a plurality of nucleic acids into the DNA of a cell through recombination where the cell has increased distance between Okazaki fragments or lowered or reduced frequency of Okazaki fragment initiation.

Embodiments of the present disclosure include methods of increasing gaps between Okazaki fragments or lowering or reducing frequency of Okazaki fragment initiation while introducing one or more or a plurality of eXogenous nucleic acids into the DNA of the cell. According to certain aspects, disrupting the interaction between primase and helicase such as by genetically altering a cell to impair or inhibit primase activity or impair or inhibit helicase activity or both increases gaps or distance between Okazaki fragments in the cell or lowers or reduces frequency of Okazaki fragment initiation. According to certain aspects, disrupting the interaction between primase and helicase increases distance between Okazaki fragments in the cell or lowers or reduces frequency of Okazaki fragment initiation and increases allele replacement frequencies in transformation or transfection methods described herein.

According to one aspect, multiple nucleic acid sequences are introduced by recombination into a plurality of cells using a multipleX method where a plurality of cells in a vessel receive multiple nucleic acids into their genomes through recombination and where the cells eXhibits larger or increased gaps or distance between Okazaki fragments or lowered or reduced frequency of Okazaki fragment initiation. The cells can then be the subject of further recombination of one or more eXogenous nucleic acid sequences into their genomes, for eXample, by cyclic addition of eXogenous nucleic acids into cells in parallel, i.e. multiple cells being subjected to recombination in a vessel. The addition of one or more nucleic acids can be random or in a specific order or location within the genome. The addition of one or more nucleic acids can be with or without use of one or more selectable markers.

Accordingly, embodiments of the present disclosure are directed to a method including introducing one or more or a plurality of nucleic acid sequences (such as eXogenous sequences) into a cell eXhibiting larger or increased gaps or distance between Okazaki fragments or lowered or reduced frequency of Okazaki fragment initiation. Embodiments of the present disclosure are also directed to a method including transforming or transfecting a cell having larger or increased gaps or distance between Okazaki fragments or lowered or reduced frequency of Okazaki fragment initiation with one or more or a plurality of nucleic acid sequences. According to certain aspects, a transformed or transfected cell eXhibiting larger or increased gaps or distance between Okazaki fragments or lowered or reduced frequency of Okazaki fragment initiation which has one or more or a plurality of nucleic acid sequences inserted into its genome (for eXample by a process referred to as recombination), may be further transformed or transfected one or more times resulting in a cell having multiple eXogeneous nucleic acid sequences in its genome.

According to one aspect, a method is provided including transforming or transfecting a cell eXhibiting larger or increased gaps or distance between Okazaki fragments or lowered or reduced frequency of Okazaki fragment initiation using transformation medium or transfection medium including at least one nucleic acid oligomer, replacing the transformation medium or transfection medium with growth medium, incubating the cell in the growth medium, and repeating the steps of transforming or transfecting and incubating the cell in growth medium until multiple nucleic acid sequences have been introduced into the cell. In certain aspects, a pool of nucleic acid oligomers is added to the cell eXhibiting larger or increased gaps or distance between Okazaki fragments or lowered or reduced frequency of Okazaki fragment initiation in the transformation or transfection step. In other aspects, an oligomer is single-stranded DNA. In other aspects, multiple mutations are generated in a chromosome or in a genome. In still other aspects, the growth medium contains an antibiotic, and/or the growth medium is minimal medium. In certain other aspects, a plurality of cells eXhibiting larger or increased gaps or distance between Okazaki fragments or lowered or reduced frequency of Okazaki fragment initiation is contacted with a nucleic acid oligomer in the transformation or transfection step. In certain other aspects, a plurality of cells eXhibiting larger or increased gaps or distance between Okazaki fragments or lowered or reduced frequency of Okazaki fragment initiation is contacted with a plurality of nucleic acid oligomers in the transformation or transfection step. In certain other aspects, the cell or cells may be contained within a vessel such as a microfuge tube, a test tube, a cuvette, a multi-well plate, a microfiber, a flow system or other structures or systems known to those of skill in the art for carrying out the transformation or transfection of cells. According to certain aspects, the method may be automated.

Embodiments of the present disclosure are directed to attenuating interaction between DnaG primase and helicase to increase the amount of accessible ssDNA on the lagging strand of the replication fork and enhance multipleX AR frequencies. See FIG. 1. Embodiments of the present disclosure are directed to cells modified to have impaired or inhibited or disrupted primase activity or impaired or inhibited or disrupted helicase activity, or larger or increased gaps or distance between Okazaki fragments or lowered or reduced frequency of Okazaki fragment initiation and their use to increase the amount of accessible ssDNA on the lagging strand of the replication fork and enhance multipleX AR frequencies.

Aspects of the present disclosure are directed to disrupting the interaction between DnaG primase and DnaB helicase in a cell to increase multipleX allele replacement frequencies. Aspects of the present disclosure are directed to a genetically modified cell, i.e. a cell that has been genetically modified to impair or inhibit or disrupt primase activity or impair or inhibit or disrupt helicase activity or increase or enlarge gaps or distance between Okazaki fragments or lower or reduce frequency of Okazaki fragment initiation for use with recombination methods of introducing one or more eXogenous nucleic acids into a cell known to those of skill in the art and reported in the literature, such as manual recombination methods, multipleX automated genome engineering ("MAGE") or co-selection multipleX automated genome engineering ("CoS-MAGE"). It is to be understood that the methods described herein are useful with any recombination method.

According to the present disclosure, a cell deficient in one or more nucleases is useful in methods of transforming or transfecting cells described herein. Accordingly, a useful cell may have impaired or inhibited or disrupted primase activity or impaired or inhibited or disrupted helicase activity, or larger or increased gaps or distance between Okazaki fragments or lowered or reduced frequency of Okazaki fragment initiation, or the cell has increased single stranded DNA (ssDNA) on the lagging strand of the replication fork and the cell may be deficient in one or more nucleases. Nucleases within the scope of the present disclosure include at least those corresponding to the following nuclease genes: chpA, endA, eXoX, mcrB, nfi, recB, recC, recD, recJ, rutC, sbcC, sbcD, tatD, uvrB, vsr, Xni, XonA, XseA, XseB, XthA, yhaV, yhbQ, yihG, ploA, polB, and polC. One of skill in the art will readily be able to identify additional nucleases based on the present disclosure.

BRIEF DESCRIPTION OF THE DRAWINGS

The patent or application file contains at least one drawing eXecuted in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION

Figure 1:
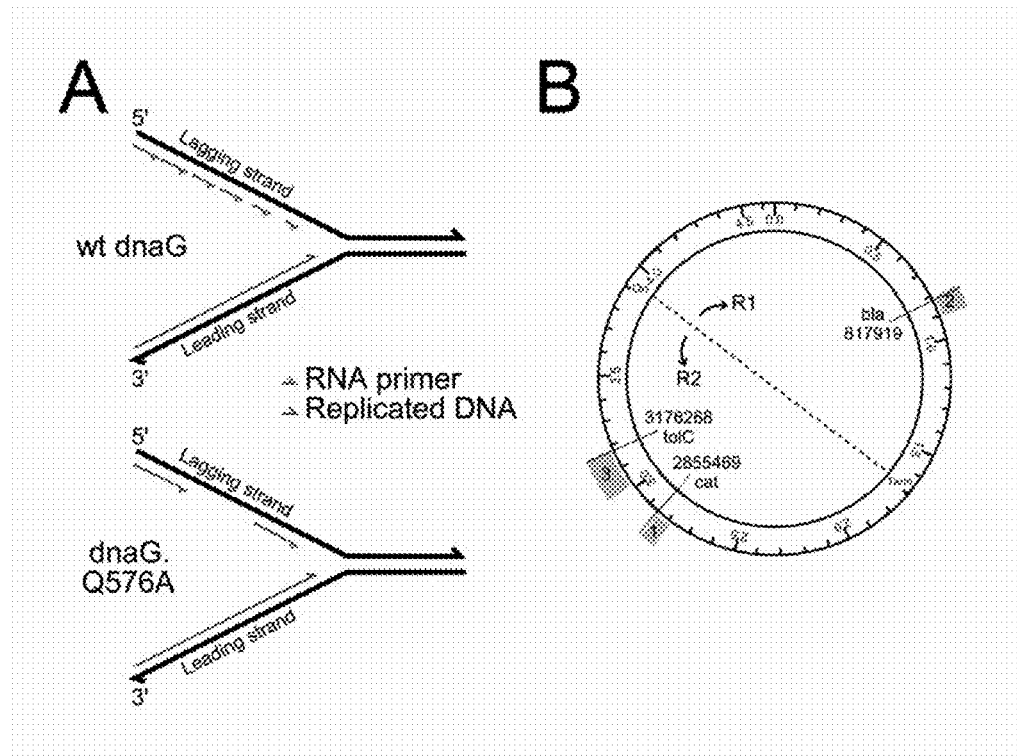
FIG. 1 is a schematic of the effect of dnaG attenuation on replication fork dynamics.

The present invention provides methods for introducing one or more eXogenous nucleic acid sequences (e.g., engineering genetic mutations) in living cells having impaired or inhibited or disrupted primase activity or impaired or inhibited or disrupted helicase activity, or larger or increased gaps or distance between Okazaki fragments or lowered or reduced frequency of Okazaki fragment initiation, as well as methods for constructing combinatorial libraries in vivo, using a variety of microbial, plant and/or animal cells as well as whole organisms. In certain embodiments of the invention, one or more or a plurality or a pool of nucleic acids (e.g., single-stranded RNA oligomers, single-stranded DNA oligomers and the like) is introduced into a set of cells having impaired or inhibited or disrupted primase activity or impaired or inhibited or disrupted helicase activity, or larger or increased gaps or distance between Okazaki fragments or lowered or reduced frequency of Okazaki fragment initiation (e.g., 50 microliters) in a suitable transfection and/or transformation medium in a suitable receptacle. According to one aspect, the one or more or a plurality or pool of eXogenous nucleic acids contain one or more desired mutations.

According to one aspect, use of a cell having impaired or inhibited or disrupted primase activity or impaired or inhibited or disrupted helicase activity weakens interaction between primase and helicase resulting in larger or increased gaps or distance between Okazaki fragments or lowered or reduced frequency of Okazaki fragment initiation. According to one aspect, use of a cell having impaired or inhibited or disrupted primase activity or impaired or inhibited or disrupted helicase activity minimizes or weakens interaction between the primase and helicase causing primase to be recruited to the replication fork in the cell less frequently. This results in fewer Okazaki fragments being initiated, longer average Okazaki fragment sizes, and more eXposed ssDNA on the lagging strand. Accordingly, aspects of the present disclosure are directed to methods of increasing Okazaki fragment length in a cell by using a cell having impaired or inhibited or disrupted primase activity or impaired or inhibited or disrupted helicase activity. Accordingly, aspects of the present disclosure are directed to methods of increasing allele conversion within a cell comprising using a cell having impaired or inhibited or disrupted primase activity or impaired or inhibited or disrupted helicase activity in a method of introducing eXogenous nucleic acids into the cell. Accordingly, aspects of the present disclosure are directed to methods of obtaining a cell with a desired set of changes to its genome including transforming or transfecting a cell having impaired or inhibited or disrupted primase activity or impaired or inhibited or disrupted helicase activity with one or more or a plurality of nucleic acid sequences.

As used herein, the terms "nucleic acid molecule," "nucleic acid sequence," "nucleic acid fragment" and "oligomer" are used interchangeably and are intended to include, but are not limited to, a polymeric form of nucleotides that may have various lengths, including either deoXyribonucleotides or ribonucleotides, or analogs thereof. Oligomers for use in the present invention can be fully designed, partially designed (i.e., partially randomized) or fully randomized. In certain aspects of the invention, a pool of nucleic acids contains single-stranded 90-mers of DNA.

Oligomers can be modified at one or more positions to enhance stability introduced during chemical synthesis or subsequent enzymatic modification or polymerase copying. These modifications include, but are not limited to, the inclusion of one or more alkylated nucleic acids, locked nucleic acids (LNAs), peptide nucleic acids (PNAs), phosphonates, phosphothioates, and the like in the oligomer. EXamples of modified nucleotides include, but are not limited to 5-fluorouracil, 5-bromouracil, 5-chlorouracil, 5-iodouracil, hypoXanthine, Xantine, 4-acetylcytosine, 5-(carboXyhydroXylmethyl)uracil, 5-carboXymethylaminomethyl-2-thiouridine, 5-carboXymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoXyaminomethyl-2-thiouracil, beta-D-mannosylqueosine, 5'-methoXycarboXymethyluracil, 5-methoXyuracil, 2-methylthio-D46-isopentenyladenine, uracil-5-oXyacetic acid (v), wybutoXosine, pseudouracil, queosine, 2-thiocytosine, 5-methyl-2-thiouracil, 2-thiouracil, 4-thiouracil, 5-methyluracil, uracil-5-oXyacetic acid methylester, uracil-5-oXyacetic acid (v), 5-methyl-2-thiouracil, 3-(3-amino-3-N-2-carboXypropyl) uracil, (acp3)w, 2,6-diaminopurine and the like. Nucleic acid molecules may also be modified at the base moiety, sugar moiety or phosphate backbone.

The multiple nucleic acid sequences can be targeted for delivery to target prokaryotic or eukaryotic cells via conventional transformation or transfection techniques. As used herein, the terms "transformation" and "transfection" are intended to refer to a variety of art-recognized techniques for introducing an eXogenous nucleic acid sequence (e.g., DNA) into a target cell, including calcium phosphate or calcium chloride co-precipitation, DEAE-deXtran-mediated transfection, lipofection, electroporation, optoporation, injection and the like. Suitable transfection media include, but are not limited to, water, CaCl$_2$, cationic polymers, lipids, and the like. Suitable materials and methods for transforming or transfecting target cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals. In certain aspects of the invention, oligomer concentrations of 0.1 to 0.5 micromolar (per oligomer) are used.

Useful receptacles for transfection and/or transformation include receptacles routinely used by those of skill in the arts of transfection, transformation and microfluidics. Suitable receptacles for use in the present invention include, but are not limited to, microfuge tubes, test tubes, cuvettes, microscope slides, multi-well plates, microfibers, flow systems, and the like.

Visually detectable markers are suitable for use in the present invention, and may be positively and negatively selected and/or screened using technologies such as fluorescence activated cell sorting (FACS) or microfluidics. EXamples of detectable markers include various enzymes, prosthetic groups, fluorescent markers, luminescent markers, bioluminescent markers, and the like. EXamples of suitable fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. EXamples of suitable bioluminescent markers include, but are not limited to, luciferase (e.g., bacterial, firefly, click beetle and the like), luciferin, aequorin and the like. EXamples of suitable enzyme systems having visually detectable signals include, but are not limited to, galactosidases, glucorinidases, phosphatases, peroXidases, cholinesterases and the like.

A target cell can be any prokaryotic or eukaryotic cell. For eXample, target cells can be bacterial cells such as *E. coli* cells, insect cells such as *Drosophila melanogaster* cells, plant cells such as *Arabidopsis thaliana* cells, yeast cells, amphibian cells such as *Xenopus laevis* cells, nematode cells such as *Caenorhabditis elegans* cells, or mammalian cells (such as Chinese hamster ovary cells (CHO), mouse cells, African green monkey kidney cells (COS), fetal human cells (293T) or other human cells). Other suitable target cells are known to those skilled in the art. Both cultured and eXplanted cells may be used according to the invention. The present invention is also adaptable for in vivo use using viral vectors including, but not limited to, replication defective retroviruses, adenoviruses, adeno-associated viruses and the like.

Target cells useful in the present invention include human cells including, but not limited to, embryonic cells, fetal cells, and adult stem cells. Human stem cells may be obtained, for eXample, from a variety of sources including embryos obtained through in vitro fertilization, from umbilical cord blood, from bone marrow and the like. In one aspect of the invention, target human cells are useful as donor-compatible cells for transplantation, e.g., via alteration of surface antigens of non-compatible third-party donor cells, or through the correction of genetic defect in cells obtained from the intended recipient patient. In another aspect of the invention, target human cells are useful for the production of therapeutic proteins, peptides, antibodies and the like.

The target cells of the invention can also be used to produce nonhuman transgenic, knockout or other genetically-modified animals. Such animals include those in which a genome, chromosome, gene or nucleic acid is altered in part, e.g., by base substitutions and/or small or large insertions and/or deletions of target nucleic acid sequences. For eXample, in one embodiment, a target cell of the invention is a fertilized oocyte or an embryonic stem cell into which the addition of multiple nucleic acid sequences has been performed. Such target cells can then be used to create non-human transgenic animals in which multiple nucleic acid sequences have been introduced into their genome. As used herein, a "transgenic animal" is a non-human animal, such as a mammal, e.g., a rodent such as a ferret, guinea pig, rat, mouse or the like, or a lagomorph such as a rabbit, in which one or more of the cells of the animal includes a transgene. Other eXamples of transgenic animals include non-human primates, cows, goats, sheep, pigs, dogs, cats, chickens, amphibians, and the like. A transgene is eXogenous DNA that is integrated into the genome of a cell from which a transgenic animal develops and which remains in the genome of the mature animal. A knockout is the removal of endogenous DNA from a cell from which a knockout animal develops, which remains deleted from the genome of the mature animal. Methods for generating transgenic and knockout animals via embryo manipulation and microinjection, particularly animals such as mice, have become conventional in the art and are described, for eXample, in U.S. Pat. Nos. 4,736,866 and 4,870,009, both by Leder et al., U.S. Pat. No. 4,873,191 by Wagner et al., and in Hogan, B., Manipulating the Mouse Embryo, (Cold Spring Harbor Laboratory Press, Cold Spring Harbor, N.Y., 1986).

This invention is further illustrated by the following eXample, which should not be construed as limiting. The contents of all references, patents and published patent applications cited throughout this application are hereby incorporated by reference in their entirety for all purposes.

EXAMPLE I

Materials and Methods

Table 1 lists DNA oligonucleotides ("oligo") used in the EXamples. All oligos were ordered with standard purification and desalting from Integrated DNA Technologies. Cultures were grown in LB-LennoX media (LB$^L$; 10 g tryptone, 5 g yeast eXtract, 5 g NaCl per 1 L water). An asterisk (*) indicates use of a phosphorothioate bond to protect against eXonuclease activity. See Wang, H. H., Isaacs, F. J., Carr, P. A., Sun, Z. Z., Xu, G., Forest, C. R. and Church, G. M. (2009), Programming cells by multipleX genome engineering and accelerated evolution, *Nature*, 460, 894-898.

TABLE 1

| Name | Used for | Sequence |
|---|---|---|
| ygaR | Set 1.850 | g*c*gaagatcagtaaagatatagaaggtggtatccctggctattaAcaag gtcaggttttgattccattcattaaagatccagtaacaa*a*a (SEQ ID NO:1) |
| yqaC | Set 1.700 | a*t*taaaaattatgatgggtccacgcgtgtcggcggtgaggcgtaActta ataaaggttgctctacctatcagcagctctacaatgaat*t*c (SEQ ID NO:2) |

TABLE 1-continued

| Name | Used for | Sequence |
| --- | --- | --- |
| gabT | Set 1.600 | t*c*accattgaagacgctcagatccgtcagggtctggagatcatcagcca gtgttttgatgaggcgaagcagtaAcgccgctcctatgc*c*g (SEQ ID NO:3) |
| ygaU | Set 1.500 | t*g*acgccaattcccattatccagcaggcgatggctggcaattaaTtactc ttccggaatacgcaacacttgccccggataaattttat*c*c (SEQ ID NO:4) |
| ygaM | Set 1.400 | g*t*aggtattttatcggcgcactgttaagcatgcgcaaatcgtaAtgcaa aaatgataataaatacgcgtctttgaccccgaagcctg*t*c (SEQ ID NO:5) |
| luxS | Set 1.300 | t*t*tgaactggcttttttcaattaattgtgaagatagtttactgaTtagatgtgc agttcctgcaacttctctttcggcagtgccagtt*c*t (SEQ ID NO:6) |
| mltB | Set 1.250 | a*a*ttttacgaggaggattcagaaaaaagctgattagccagagggaagct cacgcccccctcttgtaaatagTtactgtactcgcgcca*g*c (SEQ ID NO:7) |
| srlE | Set 1.200 | a*c*tgtactgatcgcctggtttgtctccggttttatctatcaataAaggctga aacatgaccgttatttatcagaccaccatcacccgt*a*t (SEQ ID NO:8) |
| norW | Set 1.150 | a*t*cggatgaaagaggcatttggattgttgaaaacattgccgatgtaAgtg ggctactgtgcctaaaatgtcggatgcgacgctggcgc*g*t (SEQ ID NO:9) |
| ascB | Set 1.100 | a*t*cattctggtggtataaaaaagtgattgccagtaatggggaagatttaga gtaAgtaacagtgccggatgcggcgtgaacgccttat*c*c (SEQ ID NO:10) |
| bioD | Set 2.850 | t*c*gaagacgcgatctcgctcgcaatttaaccaaatacagaatggTtaca acaaggcaaggtttatgtactttccggttgccgcattttt*c*t (SEQ ID NO:11) |
| moaE | Set 2.700 | c*g*taaacgtatgtactgagcggtgaaattgccggacgcagcggtgcctt atccggctaacaaaaaaTtaccagcgttttgccgcctgc*t*g (SEQ ID NO:12) |
| ybhM | Set 2.600 | g*c*gatgtgaagtttagttaagttcttagtatgtgcatttacggTtaatgaa aaaaacgcgtatgcctttgccagacaagcgttatag*c*t (SEQ ID NO:13) |
| ybhS | Set 2.500 | t*t*tatcggcctgacgtggctgaaaaccaaacgtcggctggattaAggag aagagcatgtttcatcgcttatggacgttaatccgcaaa*g*a (SEQ ID NO:14) |
| ybiH | Set 2.400 | c*a*tatcgacctgattttgcaaggattatcgcaaaggagtttgtaAtgatga aaaaacctgtcgtgatcggattggcggtagtggtact*t*g (SEQ ID NO:15) |
| ybiR | Set 2.300 | t*c*tgaattaatcttcaaaacttaaagcaaaaggcggactcataatccgcct tttttatttgccagaccTtagttggccgggagtataaa*c*t (SEQ ID NO:16) |
| yliD | Set 2.250 | t*t*tcctgtgaggtgattacccttcaagcaatattcaaacgtaaTtatcctttt aattttcggatccagcgcatcgcgtaaaccatcgc*c*c (SEQ ID NO:17) |
| yliE | Set 2.200 | g*a*ctgactgtaagtacgaacttattgattctggacatacgtaaaTtactctt ttactaattttccacttttatcccaggcggagaatg*g*c (SEQ ID NO:18) |
| ybjK | Set 2.150 | t*c*ggttcaaggttgatgggtttttttgttatctaaaacttatctaTtaccctgca accctctcaaccatcctcaaaatctcctcgcgcg*a*t (SEQ ID NO:19) |
| rimK | Set 2.100 | c*g*caaaagcgcaggcaaaaccatgatcagtaatgtgattgcgaTtaa ccacccgttttcaggcaatattctgtcgtagcgtggcgtt*c*g (SEQ ID NO:20) |
| ygfj | Set 3.850 | c*c*ggacgactttattacagcgaaggaaaggtatactgaaatttaAaaaa cgtagttaaacgattgcgttcaaatatttaatccttccg*g*c (SEQ ID NO:21) |
| recJ | Set 3.700 | g*g*gattgtacccaatccacgctctttttttatagagaagatgacgTtaaatt ggccagatattgtcgatgataatttgcaggctgcggt*t*g (SEQ ID NO:22) |
| argO | Set 3.600 | c*t*ctggaggcaagcttagcgcctctgtttttattttttccatcagatagcgcTt aactgaacaaggcttgtgcatgagcaataccgtctc*t*c (SEQ ID NO:23) |
| yggU | Set 3.500 | a*a*tccgcaacaaatcccgccagaaatcgcggcgttaattaattaAgtat cctatgcaaaaagttgtcctcgcaaccggcaatgtcggt*a*a (SEQ ID NO:24) |
| mutY | Set 3.400 | g*t*ggagcgtttgttacagcagttacgcactggcgcgccggtttaAcgcg tgagtcgataaagaggatgattatgagcagaacgattt*t*t (SEQ ID NO:25) |
| glcC | Set 3.300 | g*c*caccatttgattcgctcggcggtgccgctggagatgaacctgagtta Actggtattaaatctgcttttcatacaatcggtaacgct*t*g (SEQ ID NO:26) |
| yghQ | Set 3.250 | a*c*tgagtcagccgagaagaatttcccgcttattcgcaccttccTtaaat caggtcatacgcttcgagatacttaacgccaaacacca*g*c (SEQ ID NO:27) |
| yghT | Set 3.200 | t*g*gttgatgcagaaaaagcgattacggattttatgaccgcgcgtggttatc actaAtcaaaaatggaaatgcccgatcgccaggaccg*g*g (SEQ ID NO:28) |

TABLE 1-continued

| Name | Used for | Sequence |
|---|---|---|
| ygiZ | Set 3.150 | t*t*ctctgtctatgagagccgttaaaacgactctcatagattttaTtaatagc aaaatataaaccgtccccaaaaaagccaccaaccac*a*a (SEQ ID NO:29) |
| yqiB | Set 3.100 | a*g*ggttaacaggctttccaaatggtgtccttaggtttcacgacgTtaataa accggaatcgccatcgctccatgtgctaaacagtatc*g*c (SEQ ID NO:30) |
| ygfJ_AGR | Set 3X.850 | c*c*actatgtcagccatcgactgtataattaccgctgccggattatcatcaA GGatggggcaatggaaaatgatgttaccctgggaaca*g*g (SEQ ID NO:31) |
| ygfT_AGR | Set 3X.700 | g*a*tgccttcgtatcaaacagagttaacatatcgcgcgccgcctgtCTtc ctgcggccattgcagtgacaaccagatccgcgccatgaa*c*t (SEQ ID NO:32) |
| ubiH_AGR | Set 3X.600 | g*t*gcagagtttgcgccgcattgcccaccagcacggtacgatgggtaata gaCCTggcggcgtgggttaacgccagcggataagcactg*c*g (SEQ ID NO:33) |
| argO_AGR | Set 3X.500 | g*g*attcagccaggtcactgccaacatggtggcgataattttccaCCTg ccttgcttcatgacttcggcgctggctaactcaatattac*t*g (SEQ ID NO:34) |
| yqgC_AGR | Set 3X.400 | g*a*atcctgagaagcgccgagatgggtataacatcggcaggtatgcaaa gcAGGgatgcagagtgcggggaacgaatcttcaccagaac*g*g (SEQ ID NO:35) |
| trmI_AGR | Set 3X.300 | t*t*ttttacgcagacgacggctacggttctttgccattatttcacTCTctcg aacattaagtcccatactccgtgaccaagacgatgac*c*a (SEQ ID NO:36) |
| glcC_AGR | Set 3X.250 | a*c*gatctgctcgacgttcgcgcattactggagggcgaatcggcaAGA ctggcggcaacgctgggaacgcaggctgattttgttgtgat*a*a (SEQ ID NO:37) |
| yghT_AGR | Set 3X.200 | g*t*gaacatcttattaccgttgtcgaaaaatatggtgctgccgaaAGGgt tcatttaggaaaacaggccggaaatgtcggtcgtgcagt*g*a (SEQ ID NO:38) |
| ygiZ_AGR | Set 3X.150 | a*a*tacatatacccaaaactcgaacatttcccgcataaagagtttCCTtaa gataagaataataagtggcgtaagaagaaaaaatgctg*c*a (SEQ ID NO:39) |
| cpdA_AGR | Set 3X.100 | c*t*tcgtgcttttgtgcaaacaggtgagtgtcggtaatttgtaaaatcctgac CCTggcctcaccagccagaggaagggttaacaggct*t*t (SEQ ID NO:1) |
| lacZ_KO1 | Set lacZ jackpot + 61 | T*C*ACTGGCCGTCGTTTTACAACGTCGTGACT GGGAAAACCCTtGaGTTACCCAACTTAATCGCC TTGCAGCACATCCCCCTTTCGCCA*G*C (SEQ ID NO:41) |
| lacZ_KO2 | Set lacZ jackpot + 264 | G*C*TGGAGTGCGATCTTCCTGAGGCCGATAC TGTCGTCGTCCCCTCAtAaTGGCAGATGCACGG TTACGATGCGCCCATCTACACCAAC*G*T (SEQ ID NO:42) |
| lacZ_KO3 | Set lacZ jackpot + 420 | C*A*CATTTAATGTTGATGAAAGCTGGCTACA GGAAGGCCAGACGtaAATTATTTTTGATGGCGT TAACTCGGCGTTTCATCTGTGGTGC*A*A (SEQ ID NO:43) |
| lacZ_KO4 | Set lacZ jackpot + 602 | T*G*ATGGTGCTGCGCTGGAGTGACGGCAGTT ATCTGGAAGATCAGtAgATGTGGCGGATGAGC GGCATTTTCCGTGACGTCTCGTTGCT*G*C (SEQ ID NO:44) |
| lacZ_KO5 | Set lacZ jackpot + 693 | T*A*AACCGACTACACAAATCAGCGATTTCCA TGTTGCCACTCGCTaaAATGATGATTTCAGCCG CGCTGTACTGGAGGCTGAAGTTCAG*A*T (SEQ ID NO:45) |
| lacZ_KO6 | Set lacZ jackpot + 1258 | T*A*CGGCCTGTATGTGGTGGATGAAGCCAAT ATTGAAACCCACtGaATGGTGCCAATGAATCGT CTGACCGATGATCCGCGCTGGTAC*C*G (SEQ ID NO:46) |
| lacZ_KO7 | Set lacZ jackpot + 1420 | G*G*GAATGAATCAGGCCACGGCGCTAATCAC GACGCGCTGTATtGaTGGATCAAATCTGTCGAT CCTTCCCGCCCGGTGCAGTATGAAG*G*C (SEQ ID NO:47) |
| lacZ_KO8 | Set lacZ jackpot + 1599 | G*T*CCATCAAAAAATGGCTTTCGCTACCTGG AGAGACGCGCCCGtaGATCCTTTGCGAATACGC CCACGCGATGGGTAACAGTCTTGGC*G*G (SEQ ID NO:48) |
| lacZ_KO9 | Set lacZ jackpot + 1710 | G*T*TTCGTCAGTATCCCCGTTTACAGGGCGGC TTCGTCTGGGACTaaGTGGATCAGTCGCTGATT AAATATGATGAAAACGGCAACCCG*T*G (SEQ ID NO:49) |
| lacZ_KO10 | Set lacZ jackpot + 1890 | A*G*CGCTGACGGAAGCAAAACACCAGCAGC AGTTTTTCCAGTTCtGaTTATCCGGGCAAACCA TCGAAGTGACCAGCGAATACCTGTTC*C*G (SEQ ID NO:50) |

TABLE 1-continued

| Name | Used for | Sequence |
|---|---|---|
| YgfJ_2*: 2*_lead | Set 3.850_lead oligo | G*C*CGGAAGGATTAAATATTTGAACGCAATC GTTTAACTACGTTTTTTAAATTTCAGTATACCT TTCCTTCGCTGTAATAAAGTCGTCC*G*G (SEQ ID NO:51) |
| recJ_2*: 2*_lead | Set 3.700_lead oligo | C*A*ACCGCAGCCTGCAAATTATCATCGACAA TATCTGGCCAATTTAACGTCATCTTCTCTATAA AAAAGAGCGTGGATTGGGTACAATC*C*C (SEQ ID NO:52) |
| argO_2*: 2*_lead | Set 3.600_lead oligo | G*A*GAGACGGTATTGCTCATGCACAAGCCTT GTTCAGTTAAGCGCTATCTGATGGAAAAATAA AACAGAGGCGCTAAGCTTGCCTCCAG*A*G (SEQ ID NO:53) |
| yggU_2*: 2*_lead | Set 3.500_lead oligo | T*T*ACCGACATTGCCGGTTGCGAGGACAACT TTTTGCATAGGATACTTAATTAATTAACGCCG CGATTTCTGGCGGGATTTGTTGCGGA*T*T (SEQ ID NO:54) |
| mutY_2*: 2*_lead | Set 3.400_lead oligo | A*A*AAATCGTTCTGCTCATAAATCATCCTCTT TATCGACTCACGCGTTAAACCGGCGCGCCAGT GCGTAACTGCTGTAACAAACGCTCC*A*C (SEQ ID NO:55) |
| glcC_2*: 2*_lead | Set 3.300_lead oligo | C*A*AGCGTTACCGATTGTATGAAAAGCAGAT TTAATACCAGTTAACTTAGGTTCATCTCCAGC GGCACCGCCGAGCGAATCAAATGGTG*G*C (SEQ ID NO:56) |
| yghQ_2*: 2*_lead | Set 3.250_lead oligo | G*C*TGGTGTTTGGCGTTAAGTATCTCGAAGCG TATGACCTGATTTAAGGAAGGTGCGAATAAGC GGGGAAATTCTTCTCGGCTGACTCA*G*T (SEQ ID NO:57) |
| yghT_2*: 2*_lead | Set 3.200_lead oligo | C*C*CGGTCCTGGCGATCGGGCATTTCCATTTT TGATTAGTGATAACCACGCGCGGTCATAAAAT CCGTAATCGCTTTTTCTGCATCAAC*C*A (SEQ ID NO:58) |
| ygiZ_2*: 2*_lead | Set 3.150_lead oligo | T*T*GTGGTTGGTGGCTTTTTTGGGGACGGTTT ATATTTTGCTATTAATAAAATCTATGAGAGTC GTTTTAACGGCTCTCATAGACAGAG*A*A (SEQ ID NO:59) |
| yqiB_2*: 2*_lead | Set 3.100_lead oligo | G*C*GATACTGTTTAGCACATGGAGCGATGGC GATTCCGGTTTATTAACGTCGTGAAACCTAAG GACACCATTTGGAAAGCCTGTTAACC*C*T (SEQ ID NO:60) |
| exoX.KO* | exoX KO oligo | t*t*c*g*gcctggagcatgccatgttgcgcattatcgatacagaaacTG Atgcggtttgcagggagggatcgttgagattgcctctgttgatg (SEQ ID NO:61) |
| xseA.KO* | xseA KO oligo | g*a*a*t*ttgatctcgctcacatgttaccttctcaatcccctgcaatTGAtt taccgttagtcgcctgaatcaaacggttcgtctgctgcttg (SEQ ID NO:62) |
| recJ.KO* | recJ KO oligo | g*g*a*g*gcaattcagcgggcaagtctgccgtttcatcgacttcacgTC Acgacgaagttgtatctgttgtttcacgcgaattatttaccgct (SEQ ID NO:63) |
| xonA.KO* | xonA KO oligo | a*a*t*a*acggatttaacctaatgatgaatgacggtaagcaacaatcTG Aaccttttgtttcacgattacgaaacctttggcacgcacccg (SEQ ID NO:64) |
| Lexo.KO.MM* | Lambda exo KO oligo | t*g*a*a*acagaaagccgcagagcagaaggtggcagcatgacaccgt aacattatcctgcagcgtaccgggatcgatgtgagagctgtcgaac (SEQ ID NO:65) |
| dnaG_Q576A | Oligo to make dnaG Q576A mutation | gcacgcatggtttaagcaacgaagaacgcctggagctctggacattaaac GCggaActggcgaaaaagtgatttaacggcttaagtgccg (SEQ ID NO:66) |
| dnaG_K580A | Oligo to make dnaG K580A mutation | cgcacgcatggtttaagcaacgaagaacgcctggagctctggacattaaac caggaActggcgCaaagtgatttaacggcttaagtgcc (SEQ ID NO:67) |
| tolC.90.del | Oligo that deletes endogenous tolC | gaatttcagcgacgtttgactgccgtttgagcagtcatgtgttaaagcttcggc cccgtctgaacgtaaggcaacgtaaagatacgggttat (SEQ ID NO:68) |
| galK_KO1.100 | Oligo to delete 100 bp including a portion of galK | C*G*CGCAGTCAGCGATATCCATTTTCGCGAAT CCGGAGTGTAAGAAAACACACCGACTACAAC GACGGTTTCGTTCTGCCCTGCGCGAT*T*G (SEQ ID NO:69) |
| galK_KO1.1149 | Oligo to delete 1149 bp including a portion of galK | C*G*CGCAGTCAGCGATATCCATTTTCGCGAAT CCGGAGTGTAAGAAACGAAACTCCCGCACTG GCACCCGATGGTCAGCCGTACCGACT*G*T (SEQ ID NO:70) |
| galK_KO1.7895 | Oligo to delete 7895 bp including a portion of galK, galM, gpmA, aroG, ybgS, zitB, pnuC, and nadA | C*G*CGCAGTCAGCGATATCCATTTTCGCGAAT CCGGAGTGTAAGAACTTACCATCTCGTTTTAC AGGCTTAACGTTAAAACCGACATTA*G*C (SEQ ID NO:71) |

TABLE 1-continued

| Name | Used for | Sequence |
|---|---|---|
| ygaR_wt-f | Set 1.850_wt-f mascPCR | AAGGTGGTATCCCTGGCTATTAG (SEQ ID NO:72) |
| yqaC_wt-f | Set 1.700_wt-f mascPCR | CGGCGGTGAGGCGTAG (SEQ ID NO:73) |
| gabT_wt-f | Set 1.600_wt-f mascPCR | TTTTGATGAGGCGAAGCAGTAG (SEQ ID NO:74) |
| ygaU_wt-f | Set 1.500_wt-f mascPCR | GTTGCGTATTCCGGAAGAGTAG (SEQ ID NO:75) |
| ygaM_wt-f | Set 1.400_wt-f mascPCR | GTTAAGCATGCGCAAATCGTAG (SEQ ID NO:76) |
| luxS_wt-f | Set 1.300_wt-f mascPCR | GTTGCAGGAACTGCACATCTAG (SEQ ID NO:77) |
| mltB_wt-f | Set 1.250_wt-f mascPCR | GCTGGCGCGAGTACAGTAG (SEQ ID NO:78) |
| srlE_wt-f | Set 1.200_wt-f mascPCR | GGTTTGTCTCCGGTTTTATCTATCAATAG (SEQ ID NO:79) |
| norW_wt-f | Set 1.150_wt-f mascPCR | GATTGTTGAAAACATTGCCGATGTAG (SEQ ID NO:80) |
| ascB_wt-f | Set 1.100_wt-f mascPCR | CCAGTAATGGGGAAGATTTAGAGTAG (SEQ ID NO:81) |
| bioD_wt-f | Set 2.850_wt-f mascPCR | AGTACATAAACCTTGCCTTGTTGTAG (SEQ ID NO:82) |
| moaE_wt-f | Set 2.700_wt-f mascPCR | GCGGCAAAACGCTGGTAG (SEQ ID NO:83) |
| ybhM_wt-f | Set 2.600_wt-f mascPCR | AAGGCATACGCGTTTTTTTCATTAG (SEQ ID NO:84) |
| ybhS_wt-f | Set 2.500_wt-f mascPCR | CCAAACGTCGGCTGGATTAG (SEQ ID NO:85) |
| ybiH_wt-f | Set 2.400_wt-f mascPCR | AAGGATTATCGCAAAGGAGTTTGTAG (SEQ ID NO:86) |
| ybiR_wt-f | Set 2.300_wt-f mascPCR | TTAGTTATACTCCCGGCCAACTAG (SEQ ID NO:87) |
| yliD_wt-f | Set 2.250_wt-f mascPCR | CGCTGGATCCGAAAATTAAAGGATAG (SEQ ID NO:88) |
| yliE_wt-f | Set 2.200_wt-f mascPCR | TGGGATAAAAGTGGAAAATTAGTAAAAGAGTAG (SEQ ID NO:89) |
| ybjK_wt-f | Set 2.150_wt-f mascPCR | TTGAGAGGGTTGCAGGGTAG (SEQ ID NO:90) |
| rimK_wt-f | Set 2.100_wt-f mascPCR | GCCTGAAAACGGGTGGTTAG (SEQ ID NO:91) |
| ygfJ_wt-f | Set 3.850_wt-f mascPCR | AGCGAAGGAAAGGTATACTGAAATTTAG (SEQ ID NO:92) |
| recJ_wt-f | Set 3.700_wt-f mascPCR | TCATCGACAATATCTGGCCAATTTAG (SEQ ID NO:93) |
| argO_wt-f | Set 3.600_wt-f mascPCR | TGCACAAGCCTTGTTCAGTTAG (SEQ ID NO:94) |
| yggU_wt-f | Set 3.500_wt-f mascPCR | CAGAAATCGCGGCGTTAATTAATTAG (SEQ ID NO:95) |
| mutY_wt-f | Set 3.400_wt-f mascPCR | GGCGCGCCGGTTTAG (SEQ ID NO:96) |
| glcC_wt-f | Set 3.300_wt-f mascPCR | GCTGGAGATGAACCTGAGTTAG (SEQ ID NO:97) |

TABLE 1-continued

| Name | Used for | Sequence |
| --- | --- | --- |
| yghQ_wt-f | Set 3.250_wt-f mascPCR | CTCGAAGCGTATGACCTGATTTAG (SEQ ID NO:98) |
| yghT_wt-f | Set 3.200_wt-f mascPCR | CGCGCGTGGTTATCACTAG (SEQ ID NO:99) |
| ygiZ_wt-f | Set 3.150_wt-f mascPCR | TGGGGACGGTTTATATTTTGCTATTAG (SEQ ID NO:100) |
| yqiB_wt-f | Set 3.100_wt-f mascPCR | CGATGGCGATTCCGGTTTATTAG (SEQ ID NO:235) |
| ygfJ_WT | Set 3X.850_wt-f mascPCR | GCTGCCGGATTATCATCAAGA (SEQ ID NO:236) |
| ygfT_WT | Set 3X.700_wt-f mascPCR | GCAATGGCCGCAGGAAGG (SEQ ID NO:101) |
| ubiH_WT | Set 3X.600_wt-f mascPCR | GCACGGTACGATGGGTAATAGAT (SEQ ID NO:102) |
| argO_WT | Set 3X.500_wt-f mascPCR | GAAGTCATGAAGCAAGGCAGA (SEQ ID NO:103) |
| yqgC_WT | Set 3X.400_wt-f mascPCR | CGGCAGGTATGCAAAGCAGA (SEQ ID NO:104) |
| trmI_WT | Set 3X.300_wt-f mascPCR | AGTATGGGACTTAATGTTCGAGAGG (SEQ ID NO:105) |
| glcC_WT | Set 3X.250_wt-f mascPCR | AGGGCGAATCGGCAAGG (SEQ ID NO:106) |
| yghT_WT | Set 3X.200_wt-f mascPCR | GAAAAATATGGTGCTGCCGAAAGA (SEQ ID NO:107) |
| ygiZ_WT | Set 3X.150_wt-f mascPCR | CTTCTTACGCCACTTATTATTCTTATCTTAAGA (SEQ ID NO:108) |
| cpdA_WT | Set 3X.100_wt-f mascPCR | TGGCTGGTGAGGCCAGA (SEQ ID NO:109) |
| exoX.KO*-wt-f | exoX wt-f mascPCR primer | GCGCATTATCGATACAGAAACCT (SEQ ID NO:110) |
| xseA.KO*-wt-f | xseA wt-f mascPCR primer | CTTCTCAATCCCTGCAATTTTTACC (SEQ ID NO:111) |
| recJ.KO*-wt-f | recJ wt-f mascPCR primer | CAACAGATACAACTTCGTCGCC (SEQ ID NO:112) |
| xonA.KO*-wt-f | xonA wt-f mascPCR primer | GAATGACGGTAAGCAACAATCTACC (SEQ ID NO:113) |
| Lexo_WT-f | Lambda exo KO wt-f mascPCR primer | GGCAGCATGACACCGGA (SEQ ID NO:114) |
| dnaG_Q576A_wt-f | dnaG_Q576A wt-f mascPCR primer | TGGAGCTCTGGACATTAAACCA (SEQ ID NO:115) |
| dnaG_K580A_wt-f | dnaG_K580A wt-f mascPCR primer | CATTAAACCAGGAACTGGCGAA (SEQ ID NO:116) |
| ygaR_mut-f | Set 1.850_mut-f mascPCR | AAGGTGGTATCCCTGGCTATTAA (SEQ ID NO:117) |
| yqaC_mut-f | Set 1.700_mut-f mascPCR | CGGCGGTGAGGCGTAA (SEQ ID NO:118) |
| gabT_mut-f | Set 1.600_mut-f mascPCR | TTTTGATGAGGCGAAGCAGTAA (SEQ ID NO:119) |
| ygaU_mut-f | Set 1.500_mut-f mascPCR | GTTGCGTATTCCGGAAGAGTAA (SEQ ID NO:120) |
| ygaM_mut-f | Set 1.400_mut-f mascPCR | GTTAAGCATGCGCAAATCGTAA (SEQ ID NO:121) |

TABLE 1-continued

| Name | Used for | Sequence |
| --- | --- | --- |
| luxS_mut-f | Set 1.300_mut-f mascPCR | GTTGCAGGAACTGCACATCTAA (SEQ ID NO:122) |
| mltB_mut-f | Set 1.250_mut-f mascPCR | GCTGGCGCGAGTACAGTAA (SEQ ID NO:123) |
| srlE_mut-f | Set 1.200_mut-f mascPCR | GGTTTGTCTCCGGTTTTATCTATCAATAA (SEQ ID NO:124) |
| norW_mut-f | Set 1.150_mut-f mascPCR | GATTGTTGAAAACATTGCCGATGTAA (SEQ ID NO:125) |
| ascB_mut-f | Set 1.100_mut-f mascPCR | CCAGTAATGGGGAAGATTTAGAGTAA (SEQ ID NO:126) |
| bioD_mut-f | Set 2.850_mut-f mascPCR | AGTACATAAACCTTGCCTTGTTGTAA (SEQ ID NO:127) |
| moaE_mut-f | Set 2.700_mut-f mascPCR | GCGGCAAAACGCTGGTAA (SEQ ID NO:128) |
| ybhM_mut-f | Set 2.600_mut-f mascPCR | AAGGCATACGCGTTTTTTTCATTAA (SEQ ID NO:129) |
| ybhS_mut-f | Set 2.500_mut-f mascPCR | CCAAACGTCGGCTGGATTAA (SEQ ID NO:130) |
| ybiH_mut-f | Set 2.400_mut-f mascPCR | AAGGATTATCGCAAAGGAGTTTGTAA (SEQ ID NO:131) |
| ybiR_mut-f | Set 2.300_mut-f mascPCR | TTAGTTATACTCCCGGCCAACTAA (SEQ ID NO:132) |
| yliD_mut-f | Set 2.250_mut-f mascPCR | CGCTGGATCCGAAAATTAAAGGATAA (SEQ ID NO:133) |
| yliE_mut-f | Set 2.200_mut-f mascPCR | TGGGATAAAAGTGGAAAATTAGTAAAAGAGTAA (SEQ ID NO:134) |
| ybjK_mut-f | Set 2.150_mut-f mascPCR | TTGAGAGGGTTGCAGGGTAA (SEQ ID NO:135) |
| rimK_mut-f | Set 2.100_mut-f mascPCR | GCCTGAAAACGGGTGGTTAA (SEQ ID NO:136) |
| ygfJ_mut-f | Set 3.850_mut-f mascPCR | AGCGAAGGAAAGGTATACTGAAATTTAA (SEQ ID NO:137) |
| recJ_mut-f | Set 3.700_mut-f mascPCR | TCATCGACAATATCTGGCCAATTTAA (SEQ ID NO:138) |
| argO_mut-f | Set 3.600_mut-f mascPCR | TGCACAAGCCTTGTTCAGTTAA (SEQ ID NO:139) |
| yggU_mut-f | Set 3.500_mut-f mascPCR | CAGAAATCGCGGCGTTAATTAATTAA (SEQ ID NO:140) |
| mutY_mut-f | Set 3.400_mut-f mascPCR | GGCGCGCCGGTTTAA (SEQ ID NO:141) |
| glcC_mut-fm | Set 3.300_mut-f mascPCR | GCTGGAGATGAACCTGAGTTAA (SEQ ID NO:142) |
| yghQ_mut-f | Set 3.250_mut-f mascPCR | CTCGAAGCGTATGACCTGATTTAA (SEQ ID NO:143) |
| yghT_mut-f | Set 3.200_mut-f mascPCR | CGCGCGTGGTTATCACTAA (SEQ ID NO:144) |
| ygiZ_mut-f | Set 3.150_mut-f mascPCR | TGGGGACGGTTTATATTTTGCTATTAA (SEQ ID NO:145) |
| yqiB_mut-f | Set 3.100_mut-f mascPCR | CGATGGCGATTCCGGTTTATTAA (SEQ ID NO:146) |
| ygfJ_MUT | Set 3X.850_mut-f mascPCR | GCTGCCGGATTATCATCAAGG (SEQ ID NO:147) |

TABLE 1-continued

| Name | Used for | Sequence |
| --- | --- | --- |
| ygfT_MUT | Set 3X.700_mut-f mascPCR | GCAATGGCCGCAGGAAGA (SEQ ID NO:148) |
| ubiH_MUT | Set 3X.600_mut-f mascPCR | GCACGGTACGATGGGTAATAGAC (SEQ ID NO:149) |
| argO_MUT | Set 3X.500_mut-f mascPCR | GAAGTCATGAAGCAAGGCAGG (SEQ ID NO:150) |
| yqgC_MUT | Set 3X.400_mut-f mascPCR | GGCAGGTATGCAAAGCAGG (SEQ ID NO:151) |
| trmI_MUT | Set 3X.300_mut-f mascPCR | GAGTATGGGACTTAATGTTCGAGAGA (SEQ ID NO:152) |
| glcC_MUT | Set 3.250_mut-f mascPCR | GAGGGCGAATCGGCAAGA (SEQ ID NO:153) |
| yghT_MUT | Set 3X.200_mut-f mascPCR | AAAATATGGTGCTGCCGAAAGG (SEQ ID NO:154) |
| ygiZ_MUT | Set 3X.150_mut-f mascPCR | CTTCTTACGCCACTTATTATTCTTATCTTAAGG (SEQ ID NO:155) |
| cpdA_MUT | Set 3X.100_mut-f mascPCR | GGCTGGTGAGGCCAGG (SEQ ID NO:156) |
| exoX.KO*-mut-f | exoX mut-f mascPCR primer | GCGCATTATCGATACAGAAACTGA (SEQ ID NO:157) |
| xseA.KO*-mut-f | xseA mut-f mascPCR primer | CTTCTCAATCCCCTGCAATTGA (SEQ ID NO:158) |
| recJ.KO*-mut-f | recJ mut-f mascPCR primer | CAACAGATACAACTTCGTCGTGA (SEQ ID NO:159) |
| xonA.KO*-mut-f | xonA mut-f mascPCR primer | GAATGACGGTAAGCAACAATCTGA (SEQ ID NO:160) |
| Lexo_MUT-f | Lambda exo KO mut-f mascPCR primer | TGGCAGCATGACACCGTAA (SEQ ID NO:161) |
| dnaG_Q576A_mut-f | dnaG_Q576A mut-f mascPCR primer | GGAGCTCTGGACATTAAAC<u>GC</u> (SEQ ID NO:162) |
| dnaG_K580A_mut-f | dnaG_K580A mut-f mascPCR primer | AC<u>C</u>AGGAACTGGCGG<u>GC</u> (SEQ ID NO:163) |
| ygaR_rev | Set 1.850_rev mascPCR | TAGGTAGAGCAACCTTTATTAAGCTACG (SEQ ID NO:164) |
| yqaC_rev | Set 1.700_rev mascPCR | TAAAAATATCTACATTTCTGAAAAATGCGCA (SEQ ID NO:165) |
| gabT_rev | Set 1.600_rev mascPCR | GCGGCGATGTTGGCTT (SEQ ID NO:166) |
| ygaU_rev | Set 1.500_rev mascPCR | AGGGTATCGGGTGGCG (SEQ ID NO:167) |
| ygaM_rev | Set 1.400_rev mascPCR | CGCAACGCTTCTGCCG (SEQ ID NO:168) |
| luxS_rev | Set 1.300_rev mascPCR | ATGCCCAGGCGATGTACA (SEQ ID NO:169) |
| mltB_rev | Set 1.250_rev mascPCR | AGACTCGGCAGTTGTTACGG (SEQ ID NO:170) |
| srlE_rev | Set 1.200_rev mascPCR | GGATGGAGTGCACCTTTCAAC (SEQ ID NO:171) |
| norW_rev | Set 1.150_rev mascPCR | GTGTTGCATTTGGACACCATTG (SEQ ID NO:172) |
| ascB_rev | Set 1.100-rev mascPCR | CGCTTATCGGGCCTTCATG (SEQ ID NO:173) |

TABLE 1-continued

| Name | Used for | Sequence |
|---|---|---|
| bioD_rev | Set 2.850_rev mascPCR | CGGGAAGAACTCTTTCATTTCGC (SEQ ID NO:174) |
| moaE_rev | Set 2.700_rev mascPCR | CGTCAATCCGACAAAGACAATCA (SEQ ID NO:175) |
| ybhM_rev | Set 2.600_rev mascPCR | TTACTGGCAGGGATTATCTTTACCG (SEQ ID NO:176) |
| ybhS_rev | Set 2.500_rev mascPCR | CTGTTGTTAGGTTTCGGTTTTCCT (SEQ ID NO:177) |
| ybiH_rev | Set 2.400_rev mascPCR | GTCATAGGCGGCTTGCG (SEQ ID NO:178) |
| ybiR_rev | Set 2.300_rev mascPCR | ATGAGCCGGTAAAAGCGAC (SEQ ID NO:179) |
| yliD_rev | Set 2.250-rev mascPCR | AATAAAATTATCAGCCTTATCTTTATCTTTTCG TATAAA (SEQ ID NO:180) |
| yliE_rev | Set 2.200_rev mascPCR | CAGCAATATTTGCCACCGCA (SEQ ID NO:181) |
| ybjK_rev | Set 2.150_rev mascPCR | AACTTTTCCGCAGGGCATC (SEQ ID NO:182) |
| rimK_rev | Set 2.100_rev mascPCR | TACAACCTCTTTCGATAAAAAGACCG (SEQ ID NO:183) |
| ygfJ_rev | Set 3.850 rev mascPCR | GATGAACTGTTGCATCGGCG (SEQ ID NO:184) |
| recJ_rev | Set 3.700 rev mascPCR | CTGTACGCAGCCAGCC (SEQ ID NO:185) |
| argO_rev | Set 3.600 rev mascPCR | AATCGCTGCCTTACGCG (SEQ ID NO:186) |
| yggU_rev | Set 3.500 rev mascPCR | TAACCAAAGCCACCAGTGC (SEQ ID NO:187) |
| mutY_rev | Set 3.400 rev mascPCR | CGCGAGATATTTTTTCATCATTCCG (SEQ ID NO:188) |
| glcC_rev | Set 3.300 rev mascPCR | GGGCAAAATTGCTGTGGC (SEQ ID NO:189) |
| yghQ_rev | Set 3.250 rev mascPCR | ACCAACTGGCGATGTTATTCAC (SEQ ID NO:190) |
| yghT_rev | Set 3.200 rev mascPCR | GACGATGGTGGTGGACGG (SEQ ID NO:191) |
| ygiZ_rev | Set 3.150 rev mascPCR | ATCGCCAAATTGCATGGCA (SEQ ID NO:192) |
| yqiB_rev | Set 3.100 rev mascPCR | AAAATCCTGACTCTGGCCTCA (SEQ ID NO:193) |
| ygfJ_rev | Set 3X.850 rev mascPCR | TCTGTTTGCACTGCGGGTAC (SEQ ID NO:194) |
| ygfT_rev | Set 3X.700 rev mascPCR | TGGTTGGGCAATCTAATAGATTCTCC (SEQ ID NO:195) |
| ubiH_rev | Set 3X.600 rev mascPCR | atgAGCGTAATCATCGTCGGTG (SEQ ID NO:196) |
| argO_rev | Set 3X.500 rev mascPCR | CCGTCTCTCGCCAGCTG (SEQ ID NO:197) |
| yqgC_rev | Set 3X.400 rev mascPCR | AGCACACGACGTTTCTTTCG (SEQ ID NO:198) |
| trml_rev | Set 3X.300 rev mascPCR | ATCTGTTCTTCCGATGTACCTTCC (SEQ ID NO:199) |

TABLE 1-continued

| Name | Used for | Sequence |
| --- | --- | --- |
| glcC_rev | Set 3X.250 rev mascPCR | CTTCCAGCTCGATATCGTGGAG (SEQ ID NO:200) |
| yghT_rev | Set 3X.200 rev mascPCR | CACCACCAAAGGTTAACTGTGG (SEQ ID NO:201) |
| ygiZ_rev | Set 3X.150 rev mascPCR | CACAAACCAGACAAATACCGAGC (SEQ ID NO:202) |
| cpdA_rev | Set 3X.100 rev mascPCR | CGATGGTATCCAGCGTAAAGTTG (SEQ ID NO:203) |
| exoX.KO*-r | exoX rev mascPCR primer | GACCATGGCTTCGGTGATG (SEQ ID NO:204) |
| xseA.KO*-r | xseA rev mascPCR primer | GGTACGCTTAAGTTGATTTTCCAGC (SEQ ID NO:205) |
| recJ.KO*-r | recJ rev mascPCR primer | GGCCTGATCGACCACTTCC (SEQ ID NO:206) |
| xonA.KO*-r | xonA rev mascPCR primer | GAAATGTCTCCTGCCAAATCCAC (SEQ ID NO:207) |
| Lexo-r | Lambda exo KO rev mascPCR primer | CAAGGCCGTTGCCGTC (SEQ ID NO:208) |
| dnaG_seq-r | dnaG rev mascPCR primer for both Q576A and K580A | GCTCCATAAGACGGTATCCACA (SEQ ID NO:209) |
| Rx-P19 | forward screening primer for wt tolC deletion | GTTTCTCGTGCAATAATTTCTACATC (SEQ ID NO:210) |
| Rx-P20 | reverse screening primer for wt tolC deletion | CGTATGGATTTTGTCCGTTTCA (SEQ ID NO:211) |
| lacZ_jackpot_seq-f | forward sequencing primer for lacZ jackpot alleles | GAATTGTGAGCGGATAACAATTTC (SEQ ID NO:212) |
| lacZ_jackpot_seq-r | reverse sequencing primer for lacZ jackpot alleles | CCAGCGGCTTACCATCC (SEQ ID NO:213) |
| cat_mut* | cat inactivation oligo | G*C*ATCGTAAAGAACATTTTGAGGCATTTCA GTCAGTTGCTTAATGTACCTATAACCAGACCG TTCAGCTGGATATTACGGCCTTTTTA*A*A (SEQ ID NO:214) |
| cat_restore* | cat reactivation oligo | G*C*ATCGTAAAGAACATTTTGAGGCATTTCA GTCAGTTGCTCAATGTACCTATAACCAGACCG TTCAGCTGGATATTACGGCCTTTTTA*A*A (SEQ ID NO:215) |
| tolC-r_null_mut* | tolC inactivation oligo | A*G*CAAGCACGCCTTAGTAACCCGGAATTGC GTAAGTCTGCCGCTAAATCGTGATGCTGCCTT TGAAAAAATTAATGAAGCGCGCAGTCCA (SEQ ID NO:216) |
| tolC-r_null_revert* | tolC reactivation oligo | C*A*GCAAGCACGCCTTAGTAACCCGGAATTG CGTAAGTCTGCCGCCGATCGTGATGCTGCCTT TGAAAAAATTAATGAAGCGCGCAGTCCA (SEQ ID NO:217) |
| tolC_null_revert* | tolC reactivation oligo (leading targeting) | T*G*GACTGCGCGCTTCATTAATTTTTTTCAAAG GCAGCATCACGATCGGCGGCAGACTTACGCA ATTCCGGGTTACTAAGGCGTGCTTGCTG (SEQ ID NO:218) |
| bla_mut* | bla inactivation oligo | G*C*C*A*CATAGCAGAACTTTAAAAGTGCTCA TCATTGGAAAACGTTATTAGGGGCGAAAACTC TCAAGGATCTTACCGCTGTTGAGATCCAG (SEQ ID NO:219) |
| bla_restore* | bla reactivation oligo | G*C*C*A*CATAGCAGAACTTTAAAAGTGCTCA TCATTGGAAAACGTTCTTCGGGGCGAAAACTC TCAAGGATCTTACCGCTGTTGAGATCCAG (SEQ ID NO:220) |

TABLE 1-continued

| Name | Used for | Sequence |
|---|---|---|
| 313000.T.lacZ.coMAGE-f | Cassette primer for T.co-lacZ (lacZ coselection) | TGCTTCTCATGAACGATAACACAACTTGTTCA TGAATTAACCATTCCGGATTGAGGCACATTAA CGCC (SEQ ID NO:221) |
| 313001.T.lacZ.coMAGE-r | Cassette primer for T.co-lacZ (lacZ coselection) | ACGGAAACCAGCCAGTTCCTTTCGATGCCTGA ATTTGATCCCATAGTTTATCTAGGGCGGCGGA TT (SEQ ID NO:222) |
| 312869.seq-f | Screening primer for tolC (lacZ coselection) | GAACTTGCACTACCCATCG (SEQ ID NO:223) |
| 313126.seq-r | Screening primer for tolC (lacZ coselection) | AGTGACGGGTTAATTATCTGAAAG (SEQ ID NO:224) |
| 1255700.S.12.13b-f | Cassette primer for S.12.13b | TTTCATCTTGCCAGCATATTGGAGCGTGATCA ATTTTGATCAGCTGTGAACAGCCAGGACAGAA ATGC (SEQ ID NO:225) |
| 1255701.S.12.13b-r | Cassette primer for S.12.13b | CATTAGCAGTGATATAACGTAAGTTTTTGTAT CACTACACATCAGCCCCCTGCAGAAATAAAA AGGCCTGC (SEQ ID NO:226) |
| 1255550.Seq-f | Screening primer for S.12.13b | CATTTTTGCATTACTAATAAGAAAAAGCAAA (SEQ ID NO:227) |
| 1255850.Seq-r | Screening primer for S.12.13b | GTCCTAATCATTCTTGTAACATCCTAC (SEQ ID NO:228) |
| 1710450.Z.16.17b-f | Cassette primer for Z.16.17b | TCAGGTTAAAATCATTTAAATTTACACACGCA ACAAATATTGACCTACAAGGTGTTGACAATTA ATCATCGGC (SEQ ID NO:229) |
| 1710451.Z.16.17b-r | Cassette primer for Z.16.17b | TTTTTACTAGTGAGATAGTCCAGTTTCTGAAA AATAGCCAGTGTAATGTTAGCTTGCAAATTAA AGCCTTCG (SEQ ID NO:230) |
| 1710300.Seq-f | Screening primer for Z.16.17b | TCAGGTAATCCGTTTGCGG (SEQ ID NO:231) |
| 1710600.Seq-r | Screening primer for Z.16.17b | AACGGCAGATTTTTTCACTGC (SEQ ID NO:232) |
| LacZ::KanR.full-f | Cassette primer for lacZ::kanR | TGACCATGATTACGGATTCACTGGCCGTCGTT TTACAACGTCGTGCCTGTGACGGAAGATCACT TCG (SEQ ID NO:233) |
| LacZ::KanR.full-r | Cassette primer for lacZ::kanR | GTGCTGCAAGGCGATTAAGTTGGGTAACGCCA GGGTTTTCCCAGTAACCAGCAATAGACATAAG CGG (SEQ ID NO:234) |

EXAMPLE II

Strain Creation

Oligo-mediated λ Red recombination was used to generate all mutations as described below. All of the strains described herein were generated from EcNR2 (*Escherichia coli* MG1655 ΔmutS::cat Δ(ybhB-bioAB)::[λcI857 N(cro-ea59)::tetR-bla]). Strain Nuc5-.dnaG.Q576A was generated by recombining oligo dnaG_Q576A into strain Nuc5- (EcNR2 XonA⁻, recJ⁻, XseA⁻, eXoX⁻, and redα⁻; Mosberg, J. A., Gregg, C. J., et al., in review). EcNR2.DT was created by deleting the endogenous tolC gene using the tolC90.del recombineering oligo. EcNR2.T.co-lacZ was created by recombining a tolC cassette (T.co-lacZ) into the genome of EcNR2.DT, upstream of the lac operon. CoS-MAGE strains were prepared by inactivating a chromosomal selectable marker (cat, tolC, or bla) using a synthetic oligo. Clones with a sensitivity to the appropriate antibiotic or SDS, See Tougu, K. and Marians, K. J. (1996), The Interaction between Helicase and Primase Sets the Replication Fork Clock, Journal of Biological Chemistry, 271, 21398-21405, were identified by replica plating. The growth rate of strains EcNR2, EcNR2.dnaG.K580A, and EcNR2.dnaG.Q576A are approximately equivalent, while Nuc5-.dnaG.Q576A has a doubling time that is only ~7% longer than the others.

EXAMPLE III

Generating dsDNA Cassettes for Recombination

The T.co-lacZ dsDNA recombineering cassette was generated by PCR using primers 313000.T.lacZ.coMAGE-f and 313001.T.lacZ.coMAGE-r (Table 1). The PCR was performed using KAPA HiFi HotStart ReadyMiX, with primer concentrations of 0.5 μM and 1 μL of T.5.6 used as template (a terminator was introduced downstream of the stop codon in the tolC cassette). PCRs (50 μL total) were heat activated at 95° C. for 5 min, then cycled 30 times at 98° C. (20 sec), 62° C. (15 sec), and 72° C. (45 sec). The final eXtension was at 72° C. for 5 min. The Qiagen PCR purification kit was used to isolate the PCR products (elution in 30 μL H₂O).

Purified PCR products were quantitated on a NanoDrop™ ND1000 spectrophotometer and analyzed on a 1% agarose gel with ethidium bromide staining to confirm that the eXpected band was present and pure.

EXAMPLE IV

Performing λ Red Recombination

λ Red recombinations of ssDNA and dsDNA were performed as previously described, See DeVito, J. A. (2008), Recombineering with tolC as a selectable/counter-selectable marker: remodeling the rRNA operons of *Escherichia coli*, Nucleic Acids Res, 36, e4. Briefly, 30 µL from an overnight culture was inoculated into 3 mL of $LB^L$ and grown at 30° C. in a rotator drum until an $OD_{600}$ of 0.4-0.6 was reached (typically 2-2.5 hrs). The cultures were transferred to a shaking water bath (300 rpm at 42° C.) for 15 minutes to induce λ Red, then immediately cooled on ice for at least 3 minutes. For each recombination, 1 mL of culture was washed twice in ice cold deionized water ($dH_2O$). Cells were pelleted between each wash by centrifuging at 16,000 rcf for 20 seconds. The cell pellet was resuspended in 50 µL of $dH_2O$ containing the DNA to be recombined. For recombination of dsDNA PCR products, 50 ng of PCR product was used. Recombination using dsDNA PCR products was not performed in Nuc5-strains, since λEXo is necessary to process dsDNA into a recombinogenic ssDNA intermediate prior to β-mediated annealing, See Mosberg, J. A., Lajoie, M. J. and Church, G. M. (2010), Lambda Red Recombineering in *Escherichia coli* Occurs Through a Fully Single-Stranded Intermediate, Genetics, 186, 791-799. For eXperiments in which a single oligo was recombined, 1 µM of oligo was used. For eXperiments in which sets of ten or twenty recombineering oligos were recombined along with a co-selection oligo, 0.5 µM of each recombineering oligo and 0.2 µM of the co-selection oligo were used (5.2 µM total for 10-pleX and 10.2 µM total for 20-pleX). A BioRad GenePulser™ was used for electroporation (0.1 cm cuvette, 1.78 kV, 200 Ω, 25 µF), and electroporated cells were allowed to recover in 3 mL $LB^L$ in a rotator drum at 30° C. for at least 3 hours before plating on selective media. For MAGE and CoS-MAGE eXperiments, cultures were recovered to apparent saturation (5 or more hours) to minimize polyclonal colonies (this was especially important for strains based on Nuc5-, which eXhibit slow recovery after λ Red induction/electroporation). MAGE recovery cultures were diluted to ~5000 cfu/mL, and 50 µL of this dilution was plated on non-selective $LB^L$ agar plates. To compensate for fewer recombinants surviving the co-selection, CoS-MAGE recovery cultures were diluted to ~1E5 cf/mL and 50 µL of this dilution was plated on appropriate selective media for the co-selected resistance marker ($LB^L$ with 50 µg/mL carbenicillin for bla, 20 µg/mL chloramphenicol for cat, or 0.005% w/v SDS for tolC). Leading-targeting CoS-MAGE recovery cultures were diluted to ~5E6 cfu/mL before plating.

EXAMPLE V

Recombination Analysis

GalK activity was assayed by plating recovered recombination cultures onto MacConkey agar supplemented with 1% galactose as a carbon source. Red colonies were scored as galK+ and white colonies were galK–. LacZ activity was assayed by plating recovery cultures onto $LB^L$ agar+X-gal/ IPTG (Fisher ChromoMaX IPTG/X-Gal solution). Blue colonies were scored as lacZ+ and white colonies were lacZ–.

PCR analysis was used to confirm genotype. Specifically, Kapa 2G Fast ReadyMiX was used in colony PCRs to screen for correct insertion of dsDNA selectable markers. PCRs had a total volume of 20 µL, with 0.5 µM of each primer. These PCRs were carried out with an initial activation step at 95° C. for 2 min, then cycled 30 times at 95° C. (15 sec), 56° C. (15 sec), 72° C. (40 sec), followed by a final eXtension at 72° C. (90 sec).

Allele-specific colony PCR (ascPCR) was used to detect the dnaG_K580A and dnaG_Q576A mutations. MultipleX allele-specific colony PCR (mascPCR), See Maresca, M., Erler, A., Fu, J., Friedrich, A., Zhang, Y. M. and Stewart, A. F. (2010), Single-stranded heteroduplex intermediates in lambda Red homologous recombination, BMC Mol. Biol., 11, was used to detect the 1-2 bp mutations generated in the MAGE and CoS-MAGE eXperiments. Each allele is interrogated by two separate PCRs—one with a forward primer whose 3' end anneals to the wild type allele, and the other with a forward primer whose 3' end anneals to the mutated allele (the same reverse primer is used in both reactions). Primers are designed to have a $T_m$~62° C., but a gradient PCR is necessary to optimize annealing temperature (typically between 63° C. and 67° C.) to achieve maXimal specificity and sensitivity for a given set of primers. A wild type allele is indicated by amplification only in the wt-detecting PCR, while a mutant allele is indicated by amplification only in the mutant-detecting PCR. For mascPCR assays, primer sets for interrogating up to 10 alleles are combined in a single reaction. Each allele has a unique amplicon size (100 bp, 150 bp, 200 bp, 250 bp, 300 bp, 400 bp, 500 bp, 600 bp, 700 bp, and 850 bp). Template is prepared by growing monoclonal colonies to late-log phase in 150 uL $LB^L$ and diluting 2 uL of culture into 100 uL dH2O. Typical mascPCR reactions use KAPA2GFast MultipleX PCR ReadyMiX and 10× Kapa dye in a total volume of 10 µL, with 0.2 µM of each primer and 2 µL of template. These PCRs were carried out with an initial activation step at 95° C. (3 min), then cycled 27 times at 95° C. (15 sec), 63-67° C. (30 sec; annealing temperature optimized for each set of mascPCR primers), and 72° C. (70 sec), followed by a final eXtension at 72° C. (5 min). All mascPCR and ascPCR assays were analyzed on 1.5% agarose/EtBr gels (180 V, duration depends on distance between electrodes) to ensure adequate band resolution.

Figure 3:
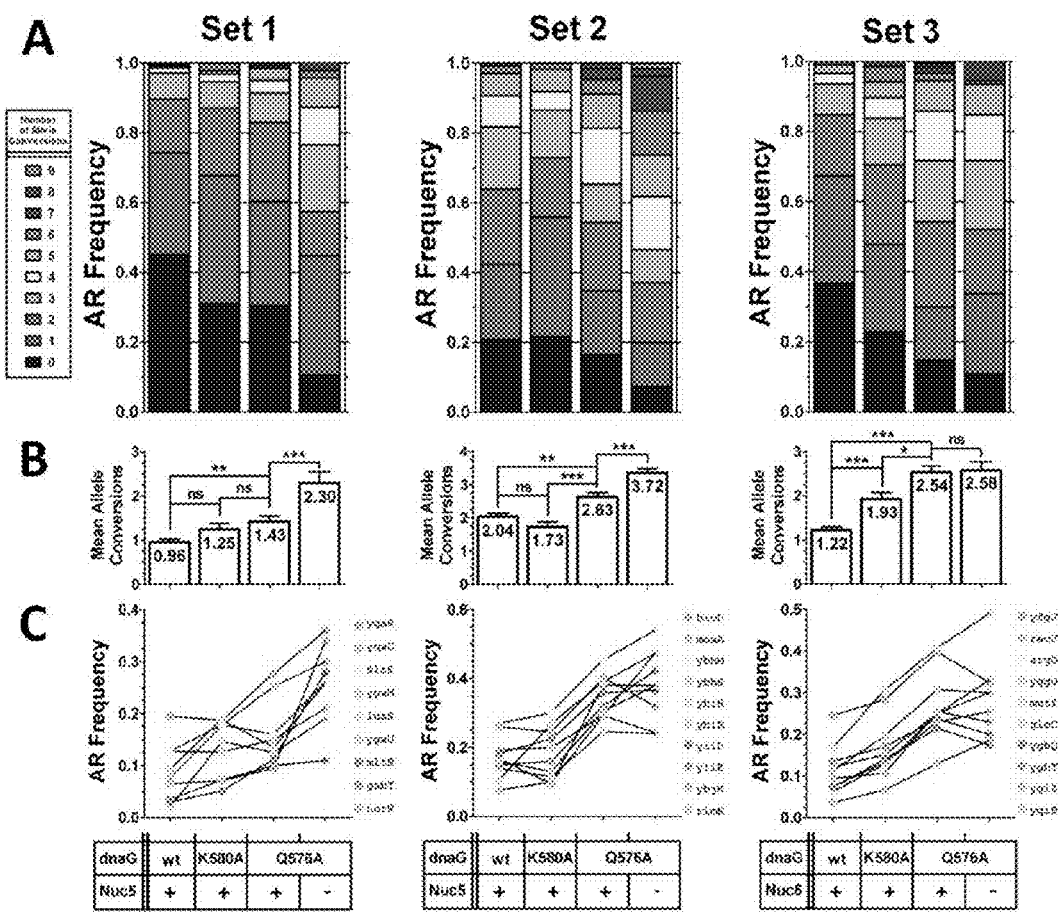
FIG. 3 is a graph of data showing that DnaG variants improve CoS-MAGE performance.
Figure 5:
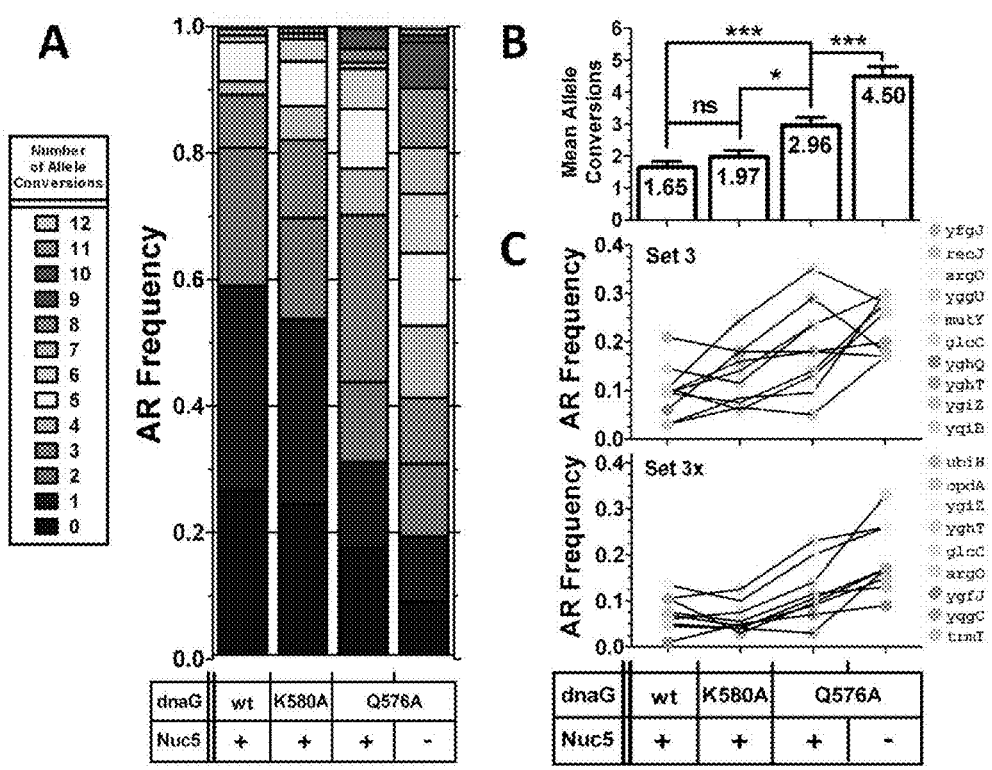
FIG. 5 is a graph indicating testing of DnaG variants with a 20-pleX CoS-MAGE oligo set.

At least two independent replicates for all strains were performed with each oligo set in CoS-MAGE eXperiments. All replicates for a given strain and oligo set were combined to generate a complete data set. Polyclonal or ambiguous mascPCR results were discarded. Mean number of alleles replaced per clone were determined by scoring each allele as 1 for converted or 0 for unmodified. Data for EcNR2 and Nuc5- are from Mosberg, J A, Gregg, C J, et al. (in review). Given the sample sizes tested in the CoS-MAGE eXperiments (n>47), parametric statistical analyses were used instead of their non-parametric equivalents, since the former are more robust with large sample sizes, See Wang, H. H. and Church, G. M. (2011), MultipleXed genome engineering and genotyping methods applications for synthetic biology and metabolic engineering, Methods Enzymol, 498, 409-426. A one way ANOVA was used to test for significant variance in CoS-MAGE performance of the strains (EcNR2, EcNR2.dnaG.K580A, EcNR2.dnaG.Q576A, & EcNR2.nuc5-.dnaG.Q576A) for a given oligo set. Subsequently, a Student's t-test was used to make pairwise comparisons with significance defined as p<0.05/n, where n is the number of pairwise comparisons. Here, n=15 as this data set was planned and collected as part of a larger set with 6 different strains although only EcNR2, EcNR2.dnaG.K580K, EcNR2.dnaG.Q576A, & EcNR2.nuc5-.dnaG.Q576A are presented here. As such, significance was defined as p<0.003 for the analyses presented in FIGS. 3 and 5. Statistical significance in FIGS. 3 and 5 are denoted using a star system where * denotes p<0.003,  denotes p<0.001, and * denotes p<0.0001. In the case of the eXperiment comparing EcNR2 and EcNR2.dnaG.Q576A using leading targeting oligos (FIG. 6), statistical significance was tested using a single t-test with significance defined as p<0.05.

For the eXperiment in which 10 oligos were targeted within lacZ, recombinants were identified by blue/white screening. The frequency of clones with 1 or more alleles replaced (# of white colonies/total # of colonies) was determined for every replicate. For white colonies only, a portion of lacZ gene was amplified with primers lacZ_jackpot_seq-f and lacZ_jackpot_seq-r (Table 1), using KAPA HiFi HotStart ReadyMiX as described above. PCR purified (Qiagen PCR purification kit) amplicons were submitted to Genewiz for Sanger sequencing in both directions using either lacZ_jackpot_seq-f or lacZ_jackpot_seq-r. Combined, the two sequencing reads for each clone interrogated all 10 alleles (i.e., unmodified or mutant sequence). Three replicates of recombinations and blue/white analysis were performed to ensure consistency, but only one replicate was sequenced (n=39 for EcNR2 and n=55 for EcNR2.dnaG.Q576A). Mean number of alleles replaced per clone were determined as described above. We tested for statistically significant differences in mean allele conversion between the strains using a Student's t-test with significance defined as p<0.05. Statistical significance in FIG. 4C is denoted using a star system where *** denotes p<0.0001.

EXAMPLE VI

Impaired Primase Activity Enhances MultipleX Allele Replacement Frequency

It is generally accepted that Redβ mediates annealing of eXogenous DNA to the lagging strand of the replication fork prior to eXtension as a nascent Okazaki Fragment, See Jekel, J. F., Katz, D. L., Elmore, J. G. and Wild, D. (2001), Epidemiology, Biostatistics, & Preventative Medicine. W.B. Saunders. The amount of ssDNA on the lagging strand was increased by disrupting the ability of DnaG primase to initiate OFs. DnaG K580A and Q576A mutations increase OF length in vitro by approXimately 1.5-fold and 8-fold, respectively. See Table 2 which is an estimation of Okazaki fragment length in EcNR2.dnaG.K580A and EcNR2.dnaG.Q576A.

TABLE 2

| [Primase] (nM) | WT dnaG Okazaki Frag (kb) | K580A Okazaki Frag (kb) | Q576A Okazaki Frag (kb) |
|---|---|---|---|
| 80 | 2.5 | 5 | 23 |
| 160 | 1.5 | 2.5 | 18 |
| 320 | 1 | 1 | 8 |
| 640 | 0.8 | nd | 3 |
| Average Fold effect compared to WT | | 1.6 | 8.2 |

According to Table 2, average Okazaki Fragment length was estimated based on in vitro results (gel images) from Tougu, K. and Marians, K. J. (1996), The Interaction between Helicase and Primase Sets the Replication Fork Clock, *Journal of Biological Chemistry,* 271, 21398-21405 for the same DnaG primase variants, tabulated above. The fold difference in OF sizes for the specified primase concentrations were compared and the average fold difference was determined (variant OF length/wt OF length). The in vivo OF lengths of ~2.3-3.1 kb and ~12-16 kb were estimated for the K580A and Q576A mutants, respectively, based on the reported ~1.5-2 kb OF lengths in wt cells grown in rich media. See Corn, J. E. and Berger, J. M. (2006), Regulation of bacterial priming and daughter strand synthesis through helicase-primase interactions, *Nucleic Acids Res.,* 34, 4082-4088; Lia, G., Michel, B. and Allemand, J.-F. (2012), Polymerase EXchange During Okazaki Fragment Synthesis Observed in Living Cells, *Science,* 335, 328-331; Okazaki, R., Okazaki, T., Sakabe, K., Sugimoto, K. and Sugino, A. (1968), Mechanism of DNA chain growth. I. Possible discontinuity and unusual secondary structure of newly synthesized chains, *Proceedings of the National Academy of Sciences,* 59, 598-605. However, these approXimations may be imperfect since Tougu et al. performed this analysis in vitro and did not use the same EcNR2.dnaG.K580A and EcNR2.dnaG.Q576A strains. Other conditions and/or host factors not accounted for in vitro may affect priming efficiency.

Figure 2:
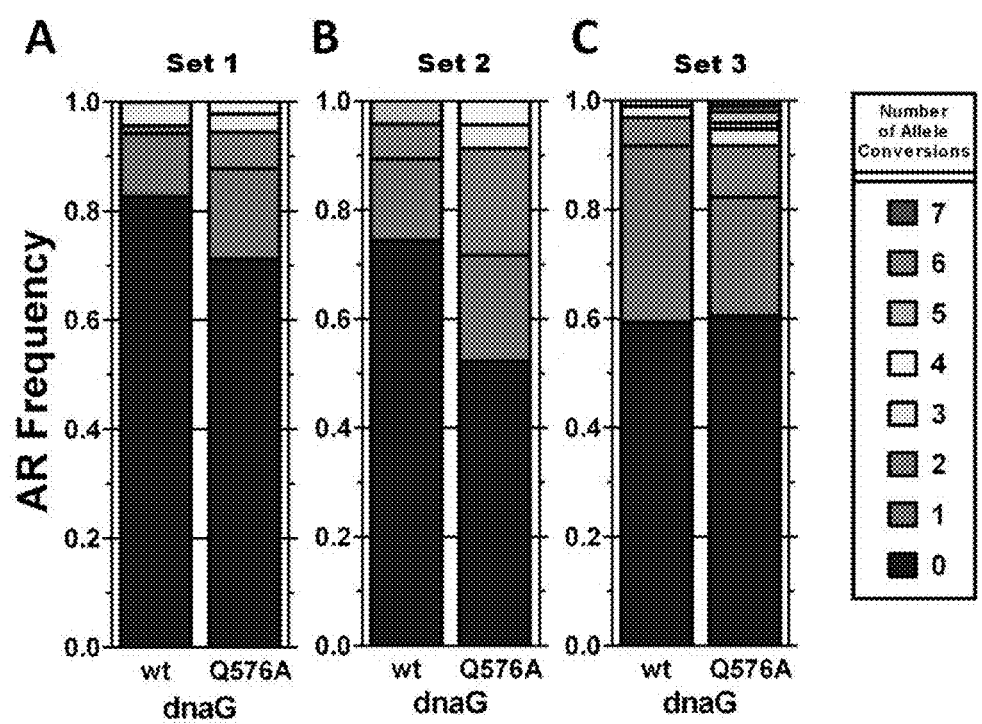
FIG. 2 is a graph of data showing that DnaG variants improve MAGE performance.

EcNR2, EcNR2.dnaG.K580A, and EcNR2.dnaG.Q576A were compared to determine whether longer OFs would improve recombination of eXogenous nucleic acids. Three sets of recombineering oligos (designed in to convert TAG codons to TAA and renamed herein for clarity as Sets 1-3) were used in order to control for potential oligo-, allele-, region-, and replichore-specific effects. FIG. 1A is a schematic showing the replication fork in *E. coli,* including the leading and lagging strands undergoing DNA synthesis. DnaG synthesizes RNA primers (red) onto the lagging template strand, which in turn initiate Okazaki fragment synthesis (blue) by PolIII. Compared to wt DnaG primase, the variants tested have lower affinities for DnaB helicase. Since the DnaG-DnaB interaction is necessary for primase function, primer synthesis occurs less frequently, thereby eXposing larger regions of ssDNA on the lagging template strand. FIG. 1B is a schematic representing the *E. coli* MG1655 genome with the origin (oriC) and terminus (T) of replication indicated, splitting the genome into Replichore 1 and Replichore 2. Each oligo set converts 10 TAG codons to TAA codons within the genomic regions indicated in gray. Co-selection marker positions are denoted by radial lines. The genomic regions targeted by these oligo sets are indicated in FIG. 1B. The AR distribution shifted to the right for EcNR2.dnaG.Q576A, as reflected by the increase in mean number of alleles converted per clone per MAGE cycle. See FIG. 2. EcNR2 (wt) and EcNR2.dnaG.Q576A (Q576A) were tested for their MAGE performance without co-selection using three sets of 10 oligos as described in FIG. 1B. For each set, all 10 alleles were simultaneously assayed by mascPCR after one cycle of MAGE. The data are presented using stacked AR frequency plots, which show the distribution of clones eXhibiting a given number of allele conversions. Compared to EcNR2 (A, Set 1, n=69; B, Set 2, n=47; C, Set 3, n=96), EcNR2.dnaG.Q576A eXhibited fewer clones with zero conversions for Set 1 (A, n=90) and Set 3 (C, n=96), but not for Set 2 (B, n=46). In all three sets, EcNR2.dnaG.Q576A displayed more clones with 2 or more allele conversions.

CoS-MAGE was then used in a similar eXperiment. In this eXperiment, each of the three oligo sets was paired with a co-selection oligo which restored the function of a nearby mutated selectable marker (cat for Set 1, bla for Set 2, and tolC for Set 3). Also, the dnaG.Q576A mutation was introduced into Nuc5-. EcNR2.dnaG.Q576A robustly outperformed EcNR2, yielding a significantly increased mean number of alleles converted (mean±std. error of mean) for Set 1 (FIG. 3B, left panel, 1.43±0.12 vs. 0.96±0.07. p=0.0003), Set 2 (FIG. 3B, middle panel, 2.63±0.13 vs. 2.04±0.10, p=0.0003), and Set 3 (FIG. 3B, right panel, 2.54±0.14 vs. 1.22±0.07, ***p<0.0001). In agreement with the previous observation for MAGE without co-selection, EcNR2.dnaG.Q576A eXhibited an increased AR distribution for all three oligo sets in CoS-MAGE (FIG. 3A). Furthermore, EcNR2.dnaG.K580A (intermediate-sized OFs) appears to have intermediate performance between EcNR2 (normal OFs) and EcNR2.dnaG.Q576A (longest OFs) indicating that OF length correlates with AR frequency and demonstrating that eXposing more ssDNA at the lagging strand of the replication fork enhances Redβ-mediated annealing.

Visualizing AR frequency for individual alleles in all three Sets (FIG. 3C) reinforces the relationship between OF size and MAGE performance. Compared to EcNR2, the K580A variant trends toward a modest increase in individual AR frequency, whereas the Q576A variant starkly improves AR frequency. Finally, the Nuc5-.dnaG.Q576A strain yielded the highest observed AR frequencies for all oligo sets, suggesting a combined effect of decreasing oligo degradation through nuclease inactivation and increasing the amount of eXposed target ssDNA at the lagging strand of the replication fork. EcNR2.dnaG.Q576A strongly outperformed Nuc5- for Set 3 (***p<0.0001), whereas EcNR2.dnaG.Q576A performance was not significantly different than that of Nuc5- for Sets 1 (p=0.33) and 2 (p=0.26). See Tables 3 and 4. This suggests that the relative importance of replication fork availability and oligo protection can vary for MAGE targets throughout the genome, possibly due to oligo and/or locus-specific effects that have not yet been elucidated.

TABLE 3

| Set | EcNR2 Mean ± SEM (n) | Nuc5- Mean ± SEM (n) | EcNR2.dnaG.Q576A Mean ± SEM (n) | Nuc5-.dnaG.Q576A Mean ± SEM (n) |
| --- | --- | --- | --- | --- |
| 1 | 0.96 ± 0.07 (319) | 1.58 ± 0.10 (257) | 1.43 ± 0.12 (141) | 2.30 ± 0.25 (92) |
| 2 | 2.04 ± 0.10 (269) | 2.89 ± 0.19 (142) | 2.63 ± 0.13 (236) | 3.72 ± 0.17 (191) |
| 3 | 1.22 ± 0.07 (327) | 1.61 ± 0.12 (139) | 2.54 ± 0.14 (184) | 2.59 ± 0.19 (92) |

Table 3 is a summary of mean number of alleles converted per clone for each MAGE oligo set. The mean number of alleles converted per clone, standard error of the mean (SEM), and sample size (n) were compared for EcNR2, Nuc5-, EcNR2.dnaG.Q576A, and Nuc5-.dnaG.Q576A. Nuc5- and EcNR2.dnaG.Q576A had statistically equivalent performance for Sets 1 and 2, while EcNR2.dnaG.Q576A strongly outperformed Nuc5- for Set 3. Nuc5-.dnaG.Q576A consistently outperformed all other strains. Data for EcNR2.dnaG.Q576A and Nuc5-.dnaG.Q576A were determined in this work. Data for EcNR2 and Nuc5- are from Mosberg, J. A., Gregg, C. J., et al. (in review).

TABLE 4

CoS-MAGE Allele Replacement performance of modified strains (presented as fold change from EcNR2)

| Metric | Set | Nuc5- | E2.dnaG.Q576A | Nuc5-.dnaG.Q576A |
| --- | --- | --- | --- | --- |
| Average | 1 | 1.65 | 1.49 | 2.40 |
|  | 2 | 1.41 | 1.29 | 1.82 |
|  | 3 | 1.32 | 2.08 | 2.12 |
|  | Average | 1.46 | 1.62 | 2.11 |
| 5+ Conversions | 1 | 5.28 | 3.96 | 10.18 |
|  | 2 | 2.65 | 2.01 | 4.11 |
|  | 3 | 1.07 | 4.20 | 4.52 |
|  | Average | 3.00 | 3.39 | 6.27 |
| 0 Conversions | 1 | 0.67 | 0.68 | 0.24 |
|  | 2 | 0.58 | 0.79 | 0.35 |
|  | 3 | 0.71 | 0.40 | 0.30 |
|  | Average | 0.65 | 0.62 | 0.29 |

Table 4 shows CoS-MAGE allele replacement performance of modified strains (presented as fold change from EcNR2). The fold improvement was calculated as (strain performance)/(EcNR2 performance), where performance refers to the average number of allele conversions per clone, or the fraction of clones with 5+ or 0 conversions. These metrics were the average of individual metrics for Oligo Sets 1, 2, and 3. In all three categories, Nuc5-.dnaG.Q576A eXhibited an effect that was roughly an additive combination of the effects yielded in Nuc5- and EcNR2.dnaG.Q576A. Data for EcNR2.dnaG.Q576A and Nuc5-.dnaG.Q576A were determined in this work. Data for EcNR2 and Nuc5- are from Mosberg, J. A., Gregg, C. J., et al. (in review).

With respect to FIG. 3, EcNR2, EcNR2.dnaG.K580A, EcNR2.dnaG.Q576A, and Nuc5-.dnaG.Q576A were tested for their performance in CoS-MAGE using three sets of 10 oligos as described in FIG. 1B. For each set, all 10 alleles were simultaneously assayed by mascPCR in recombinant clones after one cycle of CoS-MAGE. (A) The data are presented using stacked AR frequency plots, which show the distribution of clones eXhibiting a given number of allele conversions. (B) Mean number of alleles converted for each strain are shown with p-values indicated above the bars. Statistical significance is denoted using a star system where * denotes p<0.003,  denotes p<0.001, and * denotes p<0.0001. The data are presented as the mean (reported numerically inside each bar)±standard error of the mean. (C) AR frequencies for each individual allele are shown for all tested strains. Overall, the relative performance of each strain was Nuc5-.dnaG.Q576A>EcNR2.dnaG.Q576A>EcNR2.dnaG.K580A>EcNR2. This trend reflects an improvement commensurate with the severity of primase attenuation (i.e. the Q576A variant has more severely disrupted primase and larger OFs than the K580A variant). Furthermore, Nuc5-.dnaG.Q576A combines the benefits of the DnaG Q576A variant and the benefits of the inactivation of 5 potent eXonucleases (Mosberg, J. A., Gregg, C. J., et al., in review). For Set 1: EcNR2, n=319; EcNR2.dnaG.K580A, n=93; EcNR2.dnaG.Q576A, n=141; Nuc5⁻.dnaG.Q576A, n=47. For Set 2: EcNR2, n=269; EcNR2.dnaG.K580A, n=111; EcNR2.dnaG.Q576A, n=236; Nuc5⁻.dnaG.Q576A, n=191. For set 3: EcNR2, n=327; EcNR2.dnaG.K580A, n=136; EcNR2.dnaG.Q576A, n=184; Nuc5⁻.dnaG.Q576A, n=92.

EXAMPLE VII

Okazaki Fragment Location is not a Major Determinant of Available ssDNA on the Lagging Strand of the Replication Fork Given the significant enhancement of CoS-MAGE performance in EcNR2.dnaG.Q576A, it was investigated whether localizing all 10 targeted alleles to a single putative OF would result in "jackpot" recombinants with all 10 alleles converted. Without wishing to be bound by scientific theory, nascent Okazaki Fragments sometimes obstruct target alleles, leading to a non-accessible lagging strand. Successful replacement of one allele should indicate permissive OF localization, greatly increasing the chance that other alleles occurring within the same OF could be replaced. The larger OF size in EcNR2.dnaG.Q576A may allow many changes to occur within 1 large OF. Therefore, 10 MAGE oligos were designed that introduce inactivating nonsense mutations into a region spanning 1829 bp of lacZ. Despite their close proXimity, all 10 alleles were spaced far enough apart that their corresponding MAGE oligos would not overlap. Given the difference in average OF sizes between strains, it is unlikely for all 10 alleles to be located in the same OF in EcNR2, but quite likely that all 10 alleles would be located in the same OF in EcNR2.dnaG.Q576A. A tolC cassette (T.co-lacZ) was installed ~50 kb upstream of lacZ for efficient co-selection. Prior to use, this cassette was inactivated using the tolC-r_null_mut* oligo. Since the placement of these mutations is not compatible with mascPCR analysis, Sanger sequencing was used for analysis of white colonies. Blue colonies were scored as having zero conferred mutations. For EcNR2, 59% of the clones were white with 1.24±0.23 (mean±standard error of the mean) conversions per clone, whereas 84% of the EcNR2.dnaG.Q576A clones were white with 2.52±0.25 allele conversions per clone (FIG. 4A, 4C). While EcNR2.dnaG.Q576A eXhibits more mean allele conversions in CoS-MAGE than EcNR2 (***p<0.0001), the magnitude of this improvement (FIG. 4B) is comparable with those observed for Sets 1-3 (FIG. 3) where non-selectable oligos were spread across 70, 85, and 162 kb, respectively. Moreover, "jackpot" clones with 7+ converted alleles were not frequently observed for EcNR2.dnaG.Q576A using this oligo set. Thus although replication fork position is relevant, OF placement is not the predominant limiting factor for multipleX allele replacement. Other important factors could include target site occlusion by single stranded binding proteins or the availability of oligos, Redβ, or host factors.

Figure 4:
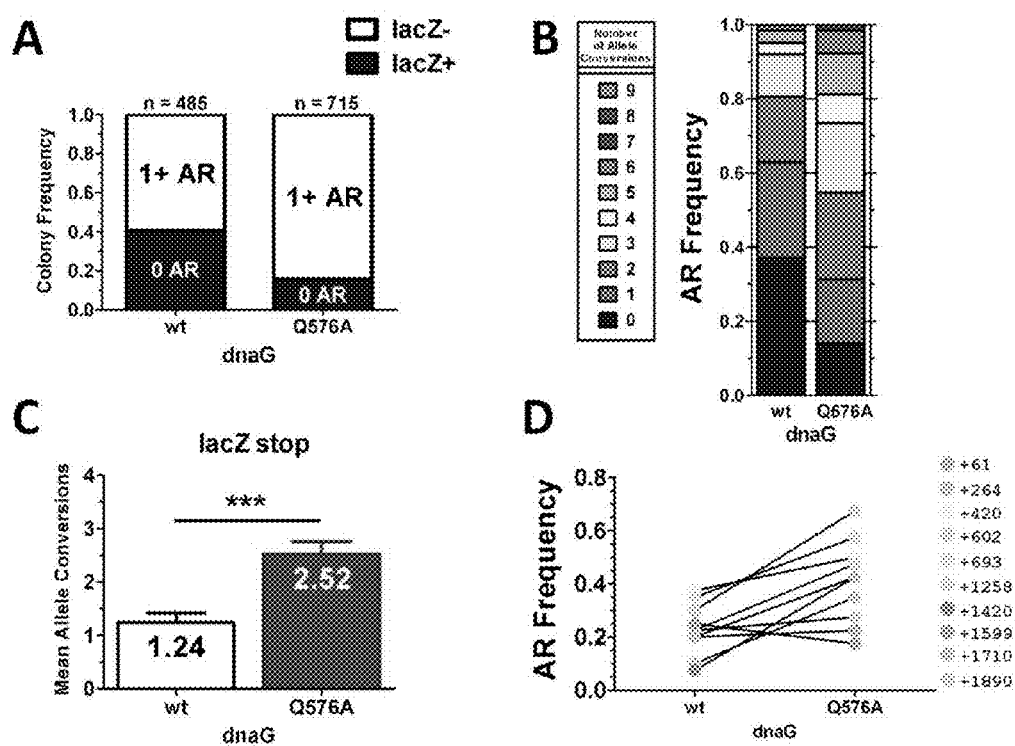
FIG. 4 is a graph of data showing that placing all targeted alleles within one Okazaki fragment does not cause a bimodal distribution for recombination frequency.

With respect to FIG. 4, EcNR2 and EcNR2.dnaG.Q576A were tested for their performance in CoS-MAGE using a set of 10 non-overlapping oligos that introduce 10 premature stop codons in the first 1,890 bp of lacZ. The targeted region of the genome is likely to be small enough to be frequently encompassed within a single Okazaki Fragment in EcNR2.dnaG.Q576A. After one cycle of CoS-MAGE, LacZ⁻ recombinant clones were Sanger sequenced to assay all 10 alleles. Recombinations were performed in triplicate to estimate the frequency of white colonies (lacZ⁻), but sequencing was only performed on a single replicate. (A) EcNR2.dnaG.Q576A (n=715, 5.33:1) eXhibited a significant increase in the lacZ⁻:lacZ⁺ ratio compared to EcNR2 (n=485, 1.46:1). (B) EcNR2.dnaG.Q576A eXhibited an AR distribution similar to those observed with Sets 1-3 (which span 70 kb, 85 kb, and 162 kb, respectively). (C) Compared to EcNR2, EcNR2.dnaG.Q576A eXhibited a higher mean number of alleles converted (unpaired t-test, ***p<0.0001). For EcNR2, n=39, and for EcNR2.dnaG.Q576A, n=55. (D) Compared to EcNR2, AR frequencies increased for 9 out of 10 individual alleles in EcNR2.dnaG.Q576A. The alleles are represented by their positions in lacZ (e.g., "+61" means that this oligo introduces a nonsense mutation by generating a mismatch at the 61$^{st}$ nucleotide of lacZ). Taken together, all of these results demonstrate improved CoS-MAGE in EcNR2.dnaG.Q576A compared to EcNR2, but no significant enhancement was obtained from targeting all oligos to a single putative OF.

EXAMPLE VIII

Improved Strains Have Larger Optimal Oligo Pool Size for MultipleX Allele Replacement A MAGE oligo pool size of approXimately 10 was found to be most effective in prior studies. 10 additional MAGE oligos (Set 3X) were designed that swapped synonymous AGA and AGG codons in alleles within the same region targeted by the Set 3 oligos. The ygfT allele (Set 3X) was not successfully assayed by mascPCR, so a maXimum of 19 allele replacements could be detected out of the 20 conversions attempted. One round of CoS-MAGE using the combined oligo Sets 3 and 3X with tolC as a selectable marker improved AR frequency in all strains (FIG. 5A). The mean number of alleles converted (and fold increase over 10-pleX means for Set 3 alone) per clone are as follows: 1.65 (1.35-fold) for EcNR2; 1.97 (1.02-fold) for EcNR2.dnaG.K580A; 2.96 (1.17-fold) for EcNR2.dnaG.Q576A; and 4.50 (1.74-fold) for Nuc5-.dnaG.Q576A (FIG. 5B). Nuc5-.dnaG.Q576A eXhibited the greatest improvement with the eXpanded oligo set, suggesting that preventing oligo degradation is important when the intracellular concentration of each individual oligo is low. Longer OFs then increase the probability that scarce oligos will find their genomic target. This observation assumes that a limited number of oligos are internalized during electroporation, which is consistent with the fact that the mole fraction of an oligo in a multipleX eXperiment affects its relative AR frequency at saturating oligo concentrations. Notably, the Set 3X oligos yielded lower recombination frequencies compared to the Set 3 alleles that converted TAG to TAA codons, and Nuc5-.dnaG.Q576A strongly elevated the AR frequency of these alleles (FIG. 5C). Nuc5-.dnaG.Q576A eXhibited the largest number of simultaneous allele conversions in a single recombination (tolC plus 12 additional alleles converted).

With respect to FIG. 5, EcNR2, EcNR2.dnaG.K580A, EcNR2.dnaG.Q576A, and Nuc5-.dnaG.Q576A were tested for their performance in CoS-MAGE using an eXpanded set of 20 oligos (Sets 3+3X). Genotypes of recombinant clones were assayed by mascPCR after one cycle of CoS-MAGE (ygfT could not be assayed by mascPCR). (A) AR frequency distributions. (B) Mean number of alleles converted±standard error of the mean, with p-values indicated above the bars. Statistical significance is denoted using a star system where * denotes p<0.003,  denotes p<0.001, and * denotes p<0.0001. (C) Mean individual AR frequencies. As seen with the smaller oligo sets, the dnaG variants reduce the number of clones with zero conversions and increase the average number of conversions per clone. Nuc5⁻.dnaG.Q576A strongly outperforms all other strains, with a mean of 4.50 alleles converted and fewer than 10% of clones having zero conversions. Notably, Nuc5-.dnaG.Q576A has strongly improved performance with Sets 3+3X compared to Set 3, whereas EcNR2.dnaG.Q576A does not. EcNR2, n=96; EcNR2.dnaG.K580A, n=113; EcNR2.dnaG.Q576A, n=95; Nuc5⁻.dnaG.Q576A, n=96.

EXAMPLE IX

Disrupting DnaG Primase Activity Enhances Leading Strand Recombination

Since DnaG primase synthesizes RNA primers only at the lagging strand of the replication fork, its alteration has minimal effect on Redβ-mediated annealing to the leading strand. Oligos designed to target the Set 3 alleles on the leading strand (reverse complements of the Set 3 oligos described above) were tested. The tolC-reverting co-selection oligo was also re-designed to target the leading strand so that the correct strand would be co-selected. Although the number of tolC-reverted co-selected recombinants were few, of the tolC+ clones, EcNR2 gave 0.85±0.13 allele conversions per clone (mean±std. error of the mean, n=88), whereas EcNR2.dnaG.Q576A gave 1.39±0.18 conversions (n=91), which was significantly different (*p=0.018). Similar to lagging targeting Set 3, a reduction in zero conversion events for EcNR2.dnaG.Q576A was observed, as well as a broadening of the distribution of total allele conversions per clone and a greater maXimum number of alleles converted (FIG. 6A). Leading-targeting CoS-MAGE yields recombination frequencies nearly within two-fold of those attained with lagging-targeting CoS-MAGE (1.22±0.07 vs. 2.54±0.14 for EcNR2 and EcNR2.dnaG.Q576A, respectively). EcNR2.dnaG.Q576A eXhibited significantly enhanced AR frequency over EcNR2 at 9 out of 10 alleles on the leading strand (FIG. 6C). Using leading targeting oligos, the co-selection advantage diminished with distance (FIG. 6B, top panel). In contrast, co-selection using lagging targeting oligos increases the AR frequency of other alleles spanning a large genomic distance (~0.5 Mb; (9)), as observed for the lagging-targeting Set 3 oligos (FIG. 6B, bottom panel).

Figure 6:
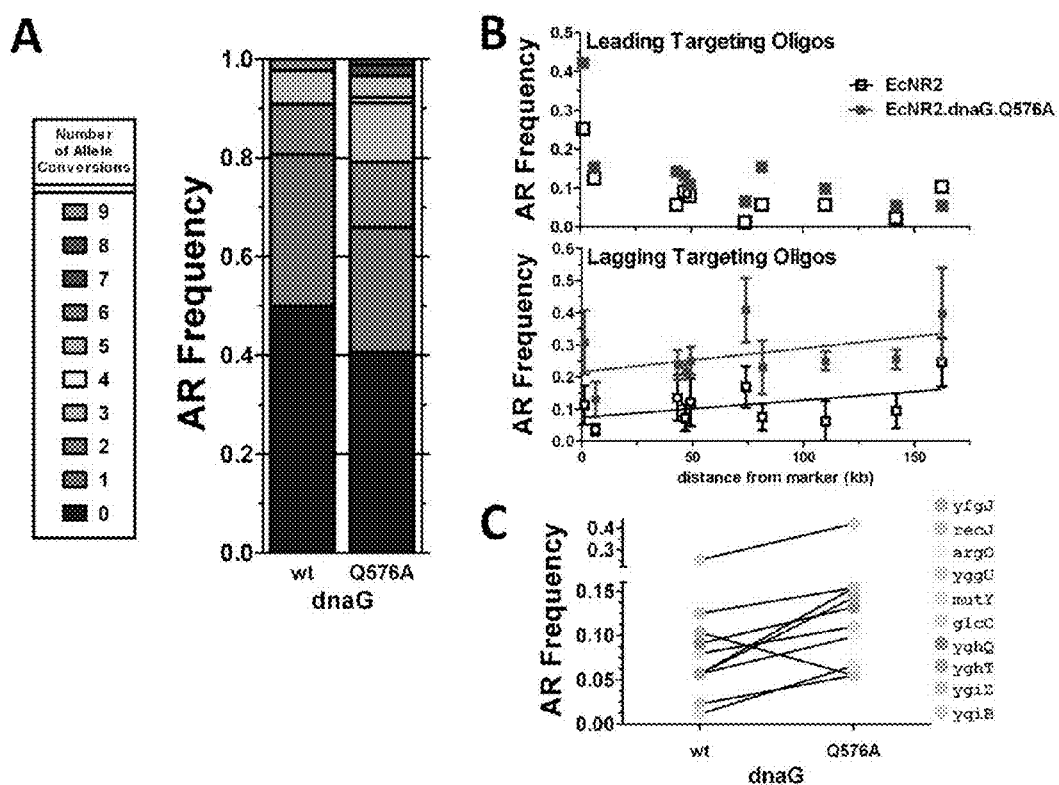
FIG. 6 are graphs showing the effect of dnaG variants and co-selection on leading-targeting CoS-MAGE.

More specifically, FIG. 6 is described as follows. (A) EcNR2.dnaG.Q576A (n=91) outperformed EcNR2 (wt, n=88) in leading-targeting Set 3 CoS-MAGE, with a reduction in zero conversion events as well as a broadening of the distribution of total allele conversions per clone. (B) For leading-targeting Set 3 oligos, AR frequency decays rapidly with increasing distance from the selectable marker (top panel). In contrast, co-selection using the corresponding set of lagging targeting oligos (see also FIG. 3C, right panel) provides robust co-selection spanning at least 0.162 Mb (bottom panel). For the lagging-targeting oligos (bottom panel), linear regression analyses (solid trendline) show that co-selection does not decrease with distance for either strain over this 0.162 Mb genomic region. (C) Individual CoS-MAGE AR frequency is plotted for each leading-targeting Set 3 oligo in EcNR2 (wt) and EcNR2.dnaG.Q576A (Q576A). AR frequency is improved for 9/10 alleles in EcNR2.dnaG.Q576A. Note that the most proXimal allele to the selectable marker (yqiB) is separated from the other alleles with a broken aXis, since its AR frequency was much higher than that of the others.

EXAMPLE X

Disrupting DnaG Primase Activity Enhances Deletions but not Insertions

MAGE is most effective at introducing short mismatches, insertions, and deletions, as these can be efficiently generated using λ Red-mediated recombination without direct selection. However, large deletions and gene-sized insertions are also important classes of mutations that could increase the scope of applications for MAGE. For eXample, combinatorial deletions could be harnessed for minimizing genomes, See Erler, A., Wegmann, S., Elie-Caille, C., Bradshaw, C. R., Maresca, M., Seidel, R., Habermann, B., Muller, D. J. and Stewart, A. F. (2009), Conformational Adaptability of Red beta during DNA Annealing and Implications for Its Structural Relationship with Rad52, J. Mol. Biol., 391, 586-598, and efficient insertions could increase the ease of building biosynthetic pathways by removing the need for linking inserted genes to selectable markers, See Posfai, G., Plunkett, G., Feher, T., Frisch, D., Keil, G. M., Umenhoffer, K., Kolisnychenko, V., Stahl, B., Sharma, S. S., de Arruda, M. et al. (2006), Emergent properties of reduced-genome Escherichia coli, Science, 312, 1044-1046 and Blomfield, I. C., Vaughn, V., Rest, R. F. and Eisenstein, B. I. (1991), Allelic eXchange in Escherichia coli the Bacillus subtilis sacB gene and a temperature-sensitive pSC101 replicon, Mol. Microbiol., 5, 1447-1457 and Warming, S., Costantino, N., Court, D. L., Jenkins, N. A. and Copeland, N. G. (2005) Simple and highly efficient BAC recombineering using galK selection, Nucleic Acids Res., 33, e36. Large deletions require two separate annealing events often spanning multiple OFs, but large insertions should anneal within the same OF, as the heterologous portion loops out and allows the flanking homologies to anneal to their adjacent targets. Maresca et al. have demonstrated that the length of deletions have little effect on Redβ-mediated recombination, but that insertion frequency is highly dependent on insert size (presumably due to constraints on λEXo-mediated degradation of the leading-targeting strand and not the lagging-targeting strand). The following study was conducted to determine whether diminishing DnaG primase function would enhance deletion and/or insertion frequencies.

Three oligos were designed that deleted 100 bp, 1,149 bp, or 7,895 bp of the genome, including a portion of galK. In addition to galK, oligo galK_KO1.7895 deleted several nonessential genes (galM, gpmA, aroG, ybgS, zitB, pnuC, and nadA). The recombined populations were screened for the GalK− phenotype (white colonies) on MacConkey agar plates supplemented with galactose as a carbon source. EcNR2.dnaG.Q576A significantly outperformed EcNR2 for the 100 bp (*p=0.03) and 1,149 bp (*p=0.03) deletions, but there was no difference detected between the two strains for the 7,895 bp deletion (p=0.74, FIG. 7). The lack of improvement using galK_KO1.7895 may be due to reduced target availability if the two homology sites are split across two or more OFs even in EcNR2.dnaG.Q576A. From the perspective of the ssDNA intermediate model for λRed recombination, deletion frequency was enhanced in EcNR2.dnaG.Q576A especially for intermediate-sized deletions (500 bp-10 kb), since less frequent priming increases the probability of both homology regions being located in the same OF.

Figure 7:
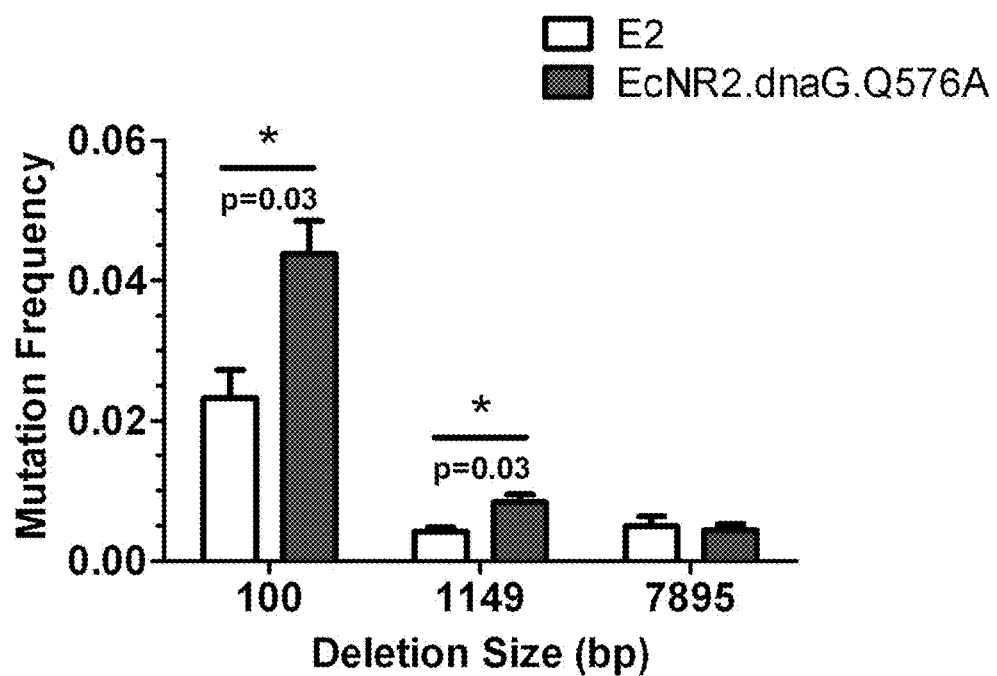
FIG. 7 are graphs showing the effect of dnaG attenuation on deletion frequency.

FIG. 7 is described as follows. DnaG primase disruption enhances gene-sized deletion frequency. Oligos that deleted 100 bp, 1,149 bp, or 7,895 bp of the genome, including a portion of galK, were recombined into EcNR2 and EcNR2.dnaG.Q576A. The recombined populations were screened for the GalK− phenotype (white colonies) on MacConkey agar plates supplemented with galactose as a carbon source. EcNR2.dnaG.Q576A significantly outperformed EcNR2 for the 100 bp and 1,149 bp deletions, but there was no difference detected between the two strains for the 7,895 bp deletion.

The insertion frequency of a selectable kanamycin resistance cassette (lacZ::kanR, 1.3 kb) targeted to lacZ was quantified. Insertion of lacZ::kanR (4, 14) in three replicates yielded recombination frequencies of 1.81E-04±6.24E-05 in EcNR2 versus 1.28E-04±4.52E-05 in EcNR2.dnaG.Q576A (p=0.30 by unpaired t-test). Modifying DnaG primase function does not appear to significantly affect λ Red-mediated gene insertion.

REFERENCES

References identified herein and listed as follows are hereby incorporated by reference herein in their entireties for all purposes. The references identified below may be referred to herein by the number associated with the reference.

1. Smith, H. O., Hutchison, C. A., Pfannkoch, C. and Venter, J. C. (2003) Generating a synthetic genome by whole genome assembly: phi X174 bacteriophage from synthetic oligonucleotides. *Proc. Natl. Acad. Sci. U.S.A.*, 100, 15440-15445.
2. Gibson, D. G., Glass, J. I., Lartigue, C., Noskov, V. N., Chuang, R. Y., Algire, M. A., Benders, G. A., Montague, M. G., Ma, L., Moodie, M. M. et al. (2010) Creation of a Bacterial Cell Controlled by a Chemically Synthesized Genome. *Science*, 329, 52-56.
3. Ellis, H. M., Yu, D. G., DiTizio, T. and Court, D. L. (2001) High efficiency mutagenesis, repair, and engineering of chromosomal DNA using single-stranded oligonucleotides. *Proc. Natl. Acad. Sci. U.S.A.*, 98, 6742-6746.
4. Wang, H. H., Isaacs, F. J., Can, P. A., Sun, Z. Z., Xu, G., Forest, C. R. and Church, G. M. (2009) Programming cells by multipleX genome engineering and accelerated evolution. *Nature*, 460, 894-898.
5. Isaacs, F. J., Carr, P. A., Wang, H. H., Lajoie, M. J., Sterling, B., Kraal, L., Tolonen, A. C., Gianoulis, T. A., Goodman, D. B., Reppas, N. B. et al. (2011) Precise manipulation of chromosomes in vivo enables genome-wide codon replacement. *Science*, 333, 348-353.
6. Li, X. T., Costantino, N., Lu, L. Y., Liu, D. P., Watt, R. M., Cheah, K. S., Court, D. L. and Huang, J. D. (2003) Identification of factors influencing strand bias in oligonucleotide-mediated recombination in *Escherichia coli*. *Nucleic Acids Res*, 31, 6674-6687.
7. Wang, H. H., Xu, G., Vonner, A. J. and Church, G. M. (2011) Modified bases enable high-efficiency oligonucleotide-mediated allelic replacement via mismatch repair evasion. *Nucleic Acids Res*, 39, 7336-7347.
8. Costantino, N. and Court, D. L. (2003) Enhanced levels of lambda Red-mediated recombinants in mismatch repair mutants. *Proc Natl Acad Sci USA*, 100, 15748-15753.
9. Carr, P. A., Wang, H. H., Sterling, B., Isaacs, F. J., Lajoie, M. J., Xu, G., Church, G. M. and Jacobson, J. M. (2012) Enhanced MultipleX Genome Engineering through Cooperative Oligonucleotide Co-selection. *Nucleic Acids Res.*, 1-11.
10. Wang, H. H., Kim, H., Cong, L., Jeong, J., Bang, D. and Church, G. M. (2012) Genome-scale promoter engineering by coselection MAGE. *Nat Meth*, 9, 591-593.
11. Zechner, E. L., Wu, C. A. and Marians, K. J. (1992) Coordinated leading- and lagging-strand synthesis at the *Escherichia coli* DNA replication fork. II. Frequency of primer synthesis and efficiency of primer utilization control Okazaki fragment size. *Journal of Biological Chemistry*, 267, 4045-4053.
12. Tougu, K. and Marians, K. J. (1996) The EXtreme C Terminus of Primase Is Required for Interaction with DnaB at the Replication Fork. *Journal of Biological Chemistry*, 271, 21391-21397.
13. Tougu, K. and Marians, K. J. (1996) The Interaction between Helicase and Primase Sets the Replication Fork Clock. *Journal of Biological Chemistry*, 271, 21398-21405.
14. DeVito, J. A. (2008) Recombineering with tolC as a selectable/counter-selectable marker: remodeling the rRNA operons of *Escherichia coli*. *Nucleic Acids Res*, 36, e4.
15. Mosberg, J. A., Lajoie, M. J. and Church, G. M. (2010) Lambda Red Recombineering in *Escherichia coli* Occurs Through a Fully Single-Stranded Intermediate. *Genetics*, 186, 791-799.
16. Maresca, M., Erler, A., Fu, J., Friedrich, A., Zhang, Y. M. and Stewart, A. F. (2010) Single-stranded heterodupleX intermediates in lambda Red homologous recombination. *BMC Mol. Biol.*, 11.
17. Wang, H. H. and Church, G. M. (2011) MultipleXed genome engineering and genotyping methods applications for synthetic biology and metabolic engineering. *Methods Enzymol*, 498, 409-426.
18. Jekel, J., Katz, D. L., Elmore, J. G. and Wild, D. (2001) *Epidemiology, Biostatistics, & Preventative Medicine*. W.B. Saunders.
19. Erler, A., Wegmann, S., Elie-Caille, C., Bradshaw, C. R., Maresca, M., Seidel, R., Habermann, B., Muller, D. J. and Stewart, A. F. (2009) Conformational Adaptability of Red beta during DNA Annealing and Implications for Its Structural Relationship with Rad52. *J. Mol. Biol.*, 391, 586-598.
20. Posfai, G., Plunkett, G., Feher, T., Frisch, D., Keil, G. M., Umenhoffer, K., Kolisnychenko, V., Stahl, B., Sharma, S. S., de Arruda, M. et al. (2006) Emergent properties of reduced-genome *Escherichia coli*. *Science*, 312, 1044-1046.
21. Blomfield, I. C., Vaughn, V., Rest, R. F. and Eisenstein, B. I. (1991) Allelic eXchange in *Escherichia coli* using the *Bacillus subtilis* sacB gene and a temperature-sensitive pSC101 replicon. *Mol. Microbiol.*, 5, 1447-1457.
22. Warming, S., Costantino, N., Court, D. L., Jenkins, N. A. and Copeland, N. G. (2005) Simple and highly efficient BAC recombineering using galK selection. *Nucleic Acids Res.*, 33, e36.
23. Tashiro, Y., Fukutomi, H., Terakubo, K., Saito, K. and Umeno, D. (2011) A nucleoside kinase as a dual selector for genetic switches and circuits. *Nucleic Acids Res.*, 39, e12.
24. Oakley, A. J., Loscha, K. V., Schaeffer, P. M., Liepinsh, E., Pintacuda, G., Wilce, M. C. J., Otting, G. and DiXon, N. E. (2005) Crystal and Solution Structures of the Helicase-binding Domain of *Escherichia coli* Primase. *Journal of Biological Chemistry*, 280, 11495-11504.

25. Corn, J. E. and Berger, J. M. (2006) Regulation of bacterial priming and daughter strand synthesis through helicase-primase interactions. *Nucleic Acids Res.*, 34, 4082-4088.
26. Lia, G., Michel, B. and Allemand, J.-F. (2012) Polymerase EXchange During Okazaki Fragment Synthesis Observed in Living Cells. *Science*, 335, 328-331.
27. Tanner, N. A., Hamdan, S. M., Jergic, S., Loscha, K. V., Schaeffer, P. M., DiXon, N. E. and van Oijen, A. M. (2008) Single-molecule studies of fork dynamics in *Escherichia coli* DNA replication. *Nat Struct Mol Biol*, 15, 170-176.
28. Nakayama, M. and Ohara, O. (2005) Improvement of recombination efficiency by mutation of Red proteins. *Biotechniques*, 38, 917-924.
29. Yao, N. Y., Georgescu, R. E., Finkelstein, J. and O'Donnell, M. E. (2009) Single-molecule analysis reveals that the lagging strand increases replisome processivity but slows replication fork progression. *Proceedings of the National Academy of Sciences*, 106, 13236-13241.
30. Rybalchenko, N., Golub, E. I., Bi, B. and Radding, C. M. (2004) Strand invasion promoted by recombination protein β of coliphage λ. *Proc. Natl. Acad. Sci. U.S.A.*, 101, 17056-17060.
31. Asai, T. and Kogoma, T. (1994) D-loops and R-loops: alternative mechanisms for the initiation of chromosome replication in *Escherichia coli*. *Journal of Bacteriology*, 176, 1807-1812.
32. Okazaki, R., Okazaki, T., Sakabe, K., Sugimoto, K. and Sugino, A. (1968) Mechanism of DNA chain growth. I. Possible discontinuity and unusual secondary structure of newly synthesized chains. *Proceedings of the National Academy of Sciences*, 59, 598-605.

EQUIVALENTS

Other embodiments will be evident to those of skill in the art. It should be understood that the foregoing description is provided for clarity only and is merely eXemplary. The spirit and scope of the present invention are not limited to the above eXample, but are encompassed by the claims. All publications, patents and patent applications cited above are incorporated by reference herein in their entirety for all purposes to the same eXtent as if each individual publication or patent application were specifically indicated to be so incorporated by reference.

What is claimed is:

1. A method of introducing a nucleic acid sequence into the genome of a cell where the cell has impaired or inhibited or disrupted DnaG primase activity, or impaired or inhibited or disrupted DnaB helicase activity, comprising transforming the cell with a nucleic acid oligomer, wherein the nucleic acid oligomer is introduced into the genome of the cell through recombination, and wherein the nucleic acid oligomer is single-stranded DNA.

2. The method of claim 1 wherein the cell is transformed with multiple nucleic acid oligomers.

3. The method of claim 1, wherein multiple mutations are generated in a chromosome of the cell through recombination.

4. The method of claim 1, wherein multiple mutations are generated in the genome of the cell through recombination.

5. The method of claim 1, wherein the cell is contacted with a pool of nucleic acid oligomers.

6. The method of claim 1 wherein the cell is deficient in at least one nuclease.

7. The method of claim 1 wherein the cell is grown into a population of cells having impaired or inhibited or disrupted DnaG primase activity or impaired or inhibited or disrupted DnaB helicase activity, and the population of cells is transformed with at least one nucleic acid oligomer.

8. The method of claim 1 wherein the cell is grown into a population of cells having impaired or inhibited or disrupted DnaG primase activity or impaired or inhibited or disrupted DnaB helicase activity, and the population of cells is transformed with at least one nucleic acid oligomer and the steps of growing and transforming are repeated until a plurality of nucleic acid sequences have been introduced into the cells.

9. A method of serially introducing a nucleic acid sequence into the genome of a cell where the cell has impaired or inhibited or disrupted DnaG primase activity or impaired or inhibited or disrupted DnaB helicase activity, comprising transforming the cell with a nucleic acid oligomer two or more times, wherein the nucleic acid oligomer is introduced into the genome of the cell through recombination, and wherein the nucleic acid oligomer is single-stranded DNA.

10. The method of claim 9 wherein the cell is transformed with multiple nucleic acid oligomers.

11. The method of claim 9, wherein multiple mutations are generated in a chromosome of the cell through recombination.

12. The method of claim 9, wherein multiple mutations are generated in the genome of the cell through recombination.

13. The method of claim 9, wherein the cell is contacted with a pool of nucleic acid oligomers.

14. The method of claim 9 wherein the cell is deficient in at least one nuclease.

15. The method of claim 9 wherein the cell is grown into a population of cells having impaired or inhibited or disrupted DnaG primase activity or impaired or inhibited or disrupted DnaB helicase activity, and the population of cells is transformed with at least one nucleic acid oligomer.

16. The method of claim 9 wherein the cell is grown into a population of cells having impaired or inhibited or disrupted DnaG primase activity or impaired or inhibited or disrupted DnaB helicase activity, and the population of cells is transformed with at least one nucleic acid oligomer and the steps of growing and transforming are repeated until a plurality of nucleic acid sequences have been introduced into the cells.

17. A method of introducing a nucleic acid sequence into the genome of a cell where the cell has impaired or inhibited or disrupted DnaG primase activity or impaired or inhibited or disrupted DnaB helicase activity, and is deficient in at least one nuclease comprising transforming the cell with a nucleic acid oligomer, wherein the nucleic acid oligomer is introduced into the genome of the cell through recombination, and wherein the nucleic acid oligomer is single-stranded DNA.

18. The method of claim 17 wherein a plurality of exogenous nucleic acid sequences are introduced through recombination into the genome of the cells having impaired or inhibited or disrupted DnaG primase activity or impaired or inhibited or disrupted DnaB helicase activity, and being deficient in at least one nuclease.

* * * * *

SEQUENCE LISTING

```
<160> NUMBER OF SEQ ID NOS: 236

<210> SEQ ID NO 1
<211> LENGTH: 90
<212> TYPE: DNA
<213> ORGANISM: Artificial
<220> FEATURE:
<223> OTHER INFORMATION: Oligonucleotide

<400> SEQUENCE: 1
gcgaagatca gtaaagatat agaaggtggt atccctggct attaacaagg tcaggttttg      60
attccattca ttaaagatcc agtaacaaaa                                       90

<210> SEQ ID NO 2
<211> LENGTH: 90
<212> TYPE: DNA
<213> ORGANISM: Artificial
<220> FEATURE:
<223> OTHER INFORMATION: Oligonucleotide

<400> SEQUENCE: 2
attaaaaatt atgatgggtc cacgcgtgtc ggcggtgagg cgtaacttaa taaaggttgc      60
tctacctatc agcagctcta caatgaattc                                       90

<210> SEQ ID NO 3
<211> LENGTH: 90
<212> TYPE: DNA
<213> ORGANISM: Artificial
<220> FEATURE:
<223> OTHER INFORMATION: Oligonucleotide

<400> SEQUENCE: 3
tcaccattga agacgctcag atccgtcagg gtctggagat catcagccag tgttttgatg      60
aggcgaagca gtaacgccgc tcctatgccg                                       90

<210> SEQ ID NO 4
<211> LENGTH: 90
<212> TYPE: DNA
<213> ORGANISM: Artificial
```

```
<220> FEATURE:
<223> OTHER INFORMATION: Oligonucleotide

<400> SEQUENCE: 4
tgacgccaat tcccattatc cagcaggcga tggctggcaa ttaattactc ttccggaata    60
cgcaacactt gccccggata aatttatcc                                      90

<210> SEQ ID NO 5
<211> LENGTH: 90
<212> TYPE: DNA
<213> ORGANISM: Artificial
<220> FEATURE:
<223> OTHER INFORMATION: Oligonucleotide

<400> SEQUENCE: 5
gtaggtattt ttatcggcgc actgttaagc atgcgcaaat cgtaatgcaa aaatgataat    60
aaatacgcgt ctttgacccc gaagcctgtc                                     90

<210> SEQ ID NO 6
<211> LENGTH: 90
<212> TYPE: DNA
<213> ORGANISM: Artificial
<220> FEATURE:
<223> OTHER INFORMATION: Oligonucleotide

<400> SEQUENCE: 6
tttgaactgg ctttttcaa ttaattgtga agatagttta ctgattagat gtgcagttcc     60
tgcaacttct ctttcggcag tgccagttct                                     90

<210> SEQ ID NO 7
<211> LENGTH: 90
<212> TYPE: DNA
<213> ORGANISM: Artificial
<220> FEATURE:
<223> OTHER INFORMATION: Oligonucleotide

<400> SEQUENCE: 7
aattttacga ggaggattca gaaaaaagct gattagccag agggaagctc acgccccct     60 cttgtaaata gttactgtac tcgcgccagc                                     90

<210> SEQ ID NO 8
<211> LENGTH: 90
<212> TYPE: DNA
<213> ORGANISM: Artificial
<220> FEATURE:
<223> OTHER INFORMATION: Oligonucleotide

<400> SEQUENCE: 8
actgtactga tcgcctggtt tgtctccggt tttatctatc aataaaggct gaaacatgac    60
cgttatttat cagaccacca tcacccgtat                                     90

<210> SEQ ID NO 9
<211> LENGTH: 90
<212> TYPE: DNA
<213> ORGANISM: Artificial
<220> FEATURE:
<223> OTHER INFORMATION: Oligonucleotide

<400> SEQUENCE: 9
atcggatgaa agaggcattt ggattgttga aaacattgcc gatgtaagtg ggctactgtg    60
cctaaaatgt cggatgcgac gctggcgcgt                                     90
```

```
<210> SEQ ID NO 10
<211> LENGTH: 90
<212> TYPE: DNA
<213> ORGANISM: Artificial
<220> FEATURE:
<223> OTHER INFORMATION: Oligonucleotide

<400> SEQUENCE: 10
atcattctgg tggtataaaa aagtgattgc cagtaatggg gaagatttag agtaagtaac    60
agtgccggat gcggcgtgaa cgccttatcc                                    90

<210> SEQ ID NO 11
<211> LENGTH: 90
<212> TYPE: DNA
<213> ORGANISM: Artificial
<220> FEATURE:
<223> OTHER INFORMATION: Oligonucleotide

<400> SEQUENCE: 11
tcgaagacgc gatctcgctc gcaatttaac caaatacaga atggttacaa caaggcaagg    60
tttatgtact ttccggttgc cgcattttct                                    90

<210> SEQ ID NO 12
<211> LENGTH: 90
<212> TYPE: DNA
<213> ORGANISM: Artificial
<220> FEATURE:
<223> OTHER INFORMATION: Oligonucleotide

<400> SEQUENCE: 12
cgtaaacgta tgtactgagc ggtgaaattg ccggacgcag cggtgcctta tccggctaac    60
aaaaaattac cagcgttttg ccgcctgctg                                    90

<210> SEQ ID NO 13
<211> LENGTH: 90
<212> TYPE: DNA
<213> ORGANISM: Artificial
<220> FEATURE:
<223> OTHER INFORMATION: Oligonucleotide

<400> SEQUENCE: 13
gcgatgtgaa gtttagttaa gttctttagt atgtgcattt acggttaatg aaaaaaacgc    60
gtatgccttt gccagacaag cgttatagct                                    90

<210> SEQ ID NO 14
<211> LENGTH: 90
<212> TYPE: DNA
<213> ORGANISM: Artificial
<220> FEATURE:
<223> OTHER INFORMATION: Oligonucleotide

<400> SEQUENCE: 14
tttatcggcc tgacgtggct gaaaaccaaa cgtcggctgg attaaggaga agagcatgtt    60
tcatcgctta tggacgttaa tccgcaaaga                                    90

<210> SEQ ID NO 15
<211> LENGTH: 90
<212> TYPE: DNA
<213> ORGANISM: Artificial
<220> FEATURE:
<223> OTHER INFORMATION: Oligonucleotide

<400> SEQUENCE: 15
```

```
catatcgacc tgattttgca aggattatcg caaaggagtt tgtaatgatg aaaaaacctg    60
tcgtgatcgg attggcggta gtggtacttg                                    90
```

<210> SEQ ID NO 16
<211> LENGTH: 90
<212> TYPE: DNA
<213> ORGANISM: Artificial
<220> FEATURE:
<223> OTHER INFORMATION: Oligonucleotide

<400> SEQUENCE: 16

```
tctgaattaa tcttcaaaac ttaaagcaaa aggcggactc ataatccgcc tttttatt     60 gccagacctt agttggccgg gagtataact                                    90
```

<210> SEQ ID NO 17
<211> LENGTH: 90
<212> TYPE: DNA
<213> ORGANISM: Artificial
<220> FEATURE:
<223> OTHER INFORMATION: Oligonucleotide

<400> SEQUENCE: 17

```
tttcctgtga ggtgattacc ctttcaagca atattcaaac gtaattatcc tttaattttc   60
ggatccagcg catcgcgtaa accatcgccc                                    90
```

<210> SEQ ID NO 18
<211> LENGTH: 90
<212> TYPE: DNA
<213> ORGANISM: Artificial
<220> FEATURE:
<223> OTHER INFORMATION: Oligonucleotide

<400> SEQUENCE: 18

```
gactgactgt aagtacgaac ttattgattc tggacatacg taaattactc ttttactaat   60
tttccacttt tatcccaggc ggagaatggc                                    90
```

<210> SEQ ID NO 19
<211> LENGTH: 90
<212> TYPE: DNA
<213> ORGANISM: Artificial
<220> FEATURE:
<223> OTHER INFORMATION: Oligonucleotide

<400> SEQUENCE: 19

```
tcggttcaag gttgatgggt tttttgttat ctaaaactta tctattaccc tgcaaccctc   60
tcaaccatcc tcaaaatctc ctcgcgcgat                                    90
```

<210> SEQ ID NO 20
<211> LENGTH: 90
<212> TYPE: DNA
<213> ORGANISM: Artificial
<220> FEATURE:
<223> OTHER INFORMATION: Oligonucleotide

<400> SEQUENCE: 20

```
cgcaaaaagc gcaggcaaaa ccatgatcag taatgtgatt gcgattaacc acccgttttc   60
aggcaatatt ctgtcgtagc gtggcgttcg                                    90
```

<210> SEQ ID NO 21
<211> LENGTH: 90
<212> TYPE: DNA

```
<213> ORGANISM: Artificial
<220> FEATURE:
<223> OTHER INFORMATION: Oligonucleotide

<400> SEQUENCE: 21
ccggacgact ttattacagc gaaggaaagg tatactgaaa tttaaaaaac gtagttaaac      60
gattgcgttc aaatatttaa tccttccggc                                      90

<210> SEQ ID NO 22
<211> LENGTH: 90
<212> TYPE: DNA
<213> ORGANISM: Artificial
<220> FEATURE:
<223> OTHER INFORMATION: Oligonucleotide

<400> SEQUENCE: 22
gggattgtac ccaatccacg ctctttttta tagagaagat gacgttaaat tggccagata      60
ttgtcgatga taatttgcag gctgcggttg                                      90

<210> SEQ ID NO 23
<211> LENGTH: 90
<212> TYPE: DNA
<213> ORGANISM: Artificial
<220> FEATURE:
<223> OTHER INFORMATION: Oligonucleotide

<400> SEQUENCE: 23
ctctggaggc aagcttagcg cctctgtttt attttccat cagatagcgc ttaactgaac       60
aaggcttgtg catgagcaat accgtctctc                                      90

<210> SEQ ID NO 24
<211> LENGTH: 90
<212> TYPE: DNA
<213> ORGANISM: Artificial
<220> FEATURE:
<223> OTHER INFORMATION: Oligonucleotide

<400> SEQUENCE: 24
aatccgcaac aaatcccgcc agaaatcgcg gcgttaatta attaagtatc ctatgcaaaa      60
agttgtcctc gcaaccggca atgtcggtaa                                      90

<210> SEQ ID NO 25
<211> LENGTH: 90
<212> TYPE: DNA
<213> ORGANISM: Artificial
<220> FEATURE:
<223> OTHER INFORMATION: Oligonucleotide

<400> SEQUENCE: 25
gtggagcgtt tgttacagca gttacgcact ggcgcgccgg tttaacgcgt gagtcgataa      60
agaggatgat ttatgagcag aacgattttt                                      90

<210> SEQ ID NO 26
<211> LENGTH: 90
<212> TYPE: DNA
<213> ORGANISM: Artificial
<220> FEATURE:
<223> OTHER INFORMATION: Oligonucleotide

<400> SEQUENCE: 26
gccaccattt gattcgctcg gcggtgccgc tggagatgaa cctgagttaa ctggtattaa      60
atctgctttt catacaatcg gtaacgcttg                                      90
```

<210> SEQ ID NO 27
<211> LENGTH: 90
<212> TYPE: DNA
<213> ORGANISM: Artificial
<220> FEATURE:
<223> OTHER INFORMATION: Oligonucleotide

<400> SEQUENCE: 27
actgagtcag ccgagaagaa tttccccgct tattcgcacc ttccttaaat caggtcatac    60
gcttcgagat acttaacgcc aaacaccagc    90

<210> SEQ ID NO 28
<211> LENGTH: 90
<212> TYPE: DNA
<213> ORGANISM: Artificial
<220> FEATURE:
<223> OTHER INFORMATION: Oligonucleotide

<400> SEQUENCE: 28
tggttgatgc agaaaaagcg attacggatt ttatgaccgc gcgtggttat cactaatcaa    60
aaatggaaat gcccgatcgc caggaccggg    90

<210> SEQ ID NO 29
<211> LENGTH: 90
<212> TYPE: DNA
<213> ORGANISM: Artificial
<220> FEATURE:
<223> OTHER INFORMATION: Oligonucleotide

<400> SEQUENCE: 29
ttctctgtct atgagagccg ttaaaacgac tctcatagat tttattaata gcaaaatata    60
aaccgtcccc aaaaaagcca ccaaccacaa    90

<210> SEQ ID NO 30
<211> LENGTH: 90
<212> TYPE: DNA
<213> ORGANISM: Artificial
<220> FEATURE:
<223> OTHER INFORMATION: Oligonucleotide

<400> SEQUENCE: 30
agggttaaca ggctttccaa atggtgtcct taggtttcac gacgttaata aaccggaatc    60
gccatcgctc catgtgctaa acagtatcgc    90

<210> SEQ ID NO 31
<211> LENGTH: 90
<212> TYPE: DNA
<213> ORGANISM: Artificial
<220> FEATURE:
<223> OTHER INFORMATION: Oligonucleotide

<400> SEQUENCE: 31
ccactatgtc agccatcgac tgtataatta ccgctgccgg attatcatca aggatggggc    60
aatggaaaat gatgttaccc tgggaacagg    90

<210> SEQ ID NO 32
<211> LENGTH: 90
<212> TYPE: DNA
<213> ORGANISM: Artificial
<220> FEATURE:
<223> OTHER INFORMATION: Oligonucleotide

```
<400> SEQUENCE: 32
gatgccttcg tatcaaacag agttaacata tcgcgcgccg cctgtcttcc tgcggccatt      60
gcagtgacaa ccagatccgc gccatgaact                                      90

<210> SEQ ID NO 33
<211> LENGTH: 90
<212> TYPE: DNA
<213> ORGANISM: Artificial
<220> FEATURE:
<223> OTHER INFORMATION: Oligonucleotide

<400> SEQUENCE: 33
gtgcagagtt tgcgccgcat tgcccaccag cacggtacga tgggtaatag acctggcggc      60
gtgggttaac gccagcggat aagcactgcg                                      90

<210> SEQ ID NO 34
<211> LENGTH: 90
<212> TYPE: DNA
<213> ORGANISM: Artificial
<220> FEATURE:
<223> OTHER INFORMATION: Oligonucleotide

<400> SEQUENCE: 34
ggattcagcc aggtcactgc caacatggtg gcgataattt ccacctgcc ttgcttcatg      60 acttcggcgc tggctaactc aatattactg                                      90

<210> SEQ ID NO 35
<211> LENGTH: 90
<212> TYPE: DNA
<213> ORGANISM: Artificial
<220> FEATURE:
<223> OTHER INFORMATION: Oligonucleotide

<400> SEQUENCE: 35
gaatcctgag aagcgccgag atgggtataa catcggcagg tatgcaaagc agggatgcag      60
agtgcgggga acgaatcttc accagaacgg                                      90

<210> SEQ ID NO 36
<211> LENGTH: 90
<212> TYPE: DNA
<213> ORGANISM: Artificial
<220> FEATURE:
<223> OTHER INFORMATION: Oligonucleotide

<400> SEQUENCE: 36 tttttacgc agacgacggc tacggttctt tgccattatt tcactctctc gaacattaag      60
tcccatactc cgtgaccaag acgatgacca                                      90

<210> SEQ ID NO 37
<211> LENGTH: 90
<212> TYPE: DNA
<213> ORGANISM: Artificial
<220> FEATURE:
<223> OTHER INFORMATION: Oligonucleotide

<400> SEQUENCE: 37
acgatctgct cgacgttcgc gcattactgg agggcgaatc ggcaagactg gcggcaacgc      60
tgggaacgca ggctgatttt gttgtgataa                                      90

<210> SEQ ID NO 38
<211> LENGTH: 90
```

```
<212> TYPE: DNA
<213> ORGANISM: Artificial
<220> FEATURE:
<223> OTHER INFORMATION: Oligonucleotide

<400> SEQUENCE: 38
gtgaacatct tattaccgtt gtcgaaaaat atggtgctgc cgaaagggtt catttaggaa     60
aacaggccgg aaatgtcggt cgtgcagtga                                      90

<210> SEQ ID NO 39
<211> LENGTH: 90
<212> TYPE: DNA
<213> ORGANISM: Artificial
<220> FEATURE:
<223> OTHER INFORMATION: Oligonucleotide

<400> SEQUENCE: 39
aatacatata cccaaaactc gaacatttcc cgcataaaga gtttccttaa gataagaata     60
ataagtggcg taagaagaaa aaatgctgca                                      90

<210> SEQ ID NO 40
<211> LENGTH: 90
<212> TYPE: DNA
<213> ORGANISM: Artificial
<220> FEATURE:
<223> OTHER INFORMATION: Oligonucleotide

<400> SEQUENCE: 40
cttcgtgctt ttgtgcaaac aggtgagtgt cggtaatttg taaaatcctg accctggcct     60
caccagccag aggaagggtt aacaggcttt                                      90

<210> SEQ ID NO 41
<211> LENGTH: 90
<212> TYPE: DNA
<213> ORGANISM: Artificial
<220> FEATURE:
<223> OTHER INFORMATION: Oligonucleotide

<400> SEQUENCE: 41
tcactggccg tcgttttaca acgtcgtgac tgggaaaacc cttgagttac ccaacttaat     60
cgccttgcag cacatccccc tttcgccagc                                      90

<210> SEQ ID NO 42
<211> LENGTH: 90
<212> TYPE: DNA
<213> ORGANISM: Artificial
<220> FEATURE:
<223> OTHER INFORMATION: Oligonucleotide

<400> SEQUENCE: 42
gctggagtgc gatcttcctg aggccgatac tgtcgtcgtc ccctcataat ggcagatgca     60
cggttacgat gcgcccatct acaccaacgt                                      90

<210> SEQ ID NO 43
<211> LENGTH: 90
<212> TYPE: DNA
<213> ORGANISM: Artificial
<220> FEATURE:
<223> OTHER INFORMATION: Oligonucleotide

<400> SEQUENCE: 43
cacatttaat gttgatgaaa gctggctaca ggaaggccag acgtaaatta ttttgatgg      60
```

```
cgttaactcg gcgtttcatc tgtggtgcaa                                              90

<210> SEQ ID NO 44
<211> LENGTH: 90
<212> TYPE: DNA
<213> ORGANISM: Artificial
<220> FEATURE:
<223> OTHER INFORMATION: Oligonucleotide

<400> SEQUENCE: 44
tgatggtgct gcgctggagt gacggcagtt atctggaaga tcagtagatg tggcggatga     60
gcggcatttt ccgtgacgtc tcgttgctgc                                      90

<210> SEQ ID NO 45
<211> LENGTH: 90
<212> TYPE: DNA
<213> ORGANISM: Artificial
<220> FEATURE:
<223> OTHER INFORMATION: Oligonucleotide

<400> SEQUENCE: 45
taaaccgact acacaaatca gcgatttcca tgttgccact cgctaaaatg atgatttcag     60
ccgcgctgta ctggaggctg aagttcagat                                      90

<210> SEQ ID NO 46
<211> LENGTH: 90
<212> TYPE: DNA
<213> ORGANISM: Artificial
<220> FEATURE:
<223> OTHER INFORMATION: Oligonucleotide

<400> SEQUENCE: 46
tacggcctgt atgtggtgga tgaagccaat attgaaaccc actgaatggt gccaatgaat     60
cgtctgaccg atgatccgcg ctggctaccg                                      90

<210> SEQ ID NO 47
<211> LENGTH: 90
<212> TYPE: DNA
<213> ORGANISM: Artificial
<220> FEATURE:
<223> OTHER INFORMATION: Oligonucleotide

<400> SEQUENCE: 47
gggaatgaat caggccacgg cgctaatcac gacgcgctgt attgatggat caaatctgtc     60
gatccttccc gcccggtgca gtatgaaggc                                      90

<210> SEQ ID NO 48
<211> LENGTH: 90
<212> TYPE: DNA
<213> ORGANISM: Artificial
<220> FEATURE:
<223> OTHER INFORMATION: Oligonucleotide

<400> SEQUENCE: 48
gtccatcaaa aaatggcttt cgctacctgg agagacgcgc ccgtagatcc tttgcgaata     60
cgcccacgcg atgggtaaca gtcttggcgg                                      90

<210> SEQ ID NO 49
<211> LENGTH: 90
<212> TYPE: DNA
<213> ORGANISM: Artificial
<220> FEATURE:
<223> OTHER INFORMATION: Oligonucleotide
```

<400> SEQUENCE: 49
gtttcgtcag tatccccgtt tacagggcgg cttcgtctgg gactaagtgg atcagtcgct     60
gattaaatat gatgaaaacg gcaacccgtg                                      90

<210> SEQ ID NO 50
<211> LENGTH: 90
<212> TYPE: DNA
<213> ORGANISM: Artificial
<220> FEATURE:
<223> OTHER INFORMATION: Oligonucleotide

<400> SEQUENCE: 50
agcgctgacg gaagcaaaac accagcagca gttttttccag ttctgattat ccgggcaaac    60
catcgaagtg accagcgaat acctgttccg                                      90

<210> SEQ ID NO 51
<211> LENGTH: 90
<212> TYPE: DNA
<213> ORGANISM: Artificial
<220> FEATURE:
<223> OTHER INFORMATION: Oligonucleotide

<400> SEQUENCE: 51
gccggaagga ttaaatattt gaacgcaatc gtttaactac gttttttaaa tttcagtata    60
cctttccttc gctgtaataa agtcgtccgg                                      90

<210> SEQ ID NO 52
<211> LENGTH: 90
<212> TYPE: DNA
<213> ORGANISM: Artificial
<220> FEATURE:
<223> OTHER INFORMATION: Oligonucleotide

<400> SEQUENCE: 52
caaccgcagc ctgcaaatta tcatcgacaa tatctggcca atttaacgtc atcttctcta    60 taaaaagag cgtggattgg gtacaatccc                                       90

<210> SEQ ID NO 53
<211> LENGTH: 90
<212> TYPE: DNA
<213> ORGANISM: Artificial
<220> FEATURE:
<223> OTHER INFORMATION: Oligonucleotide

<400> SEQUENCE: 53
gagagacggt attgctcatg cacaagcctt gttcagttaa gcgctatctg atggaaaaat    60
aaaacagagg cgctaagctt gcctccagag                                      90

<210> SEQ ID NO 54
<211> LENGTH: 90
<212> TYPE: DNA
<213> ORGANISM: Artificial
<220> FEATURE:
<223> OTHER INFORMATION: Oligonucleotide

<400> SEQUENCE: 54
ttaccgacat tgccggttgc gaggacaact ttttgcatag gatacttaat taattaacgc    60
cgcgatttct ggcgggattt gttgcggatt                                      90

<210> SEQ ID NO 55

```
<211> LENGTH: 90
<212> TYPE: DNA
<213> ORGANISM: Artificial
<220> FEATURE:
<223> OTHER INFORMATION: Oligonucleotide

<400> SEQUENCE: 55
aaaaatcgtt ctgctcataa atcatcctct ttatcgactc acgcgttaaa ccggcgcgcc      60
agtgcgtaac tgctgtaaca aacgctccac                                       90

<210> SEQ ID NO 56
<211> LENGTH: 90
<212> TYPE: DNA
<213> ORGANISM: Artificial
<220> FEATURE:
<223> OTHER INFORMATION: Oligonucleotide

<400> SEQUENCE: 56
caagcgttac cgattgtatg aaaagcagat ttaataccag ttaactcagg ttcatctcca      60
gcggcaccgc cgagcgaatc aaatggtggc                                       90

<210> SEQ ID NO 57
<211> LENGTH: 90
<212> TYPE: DNA
<213> ORGANISM: Artificial
<220> FEATURE:
<223> OTHER INFORMATION: Oligonucleotide

<400> SEQUENCE: 57
gctggtgttt ggcgttaagt atctcgaagc gtatgacctg atttaaggaa ggtgcgaata      60
agcggggaaa ttcttctcgg ctgactcagt                                       90

<210> SEQ ID NO 58
<211> LENGTH: 90
<212> TYPE: DNA
<213> ORGANISM: Artificial
<220> FEATURE:
<223> OTHER INFORMATION: Oligonucleotide

<400> SEQUENCE: 58
cccggtcctg gcgatcgggc atttccattt ttgattagtg ataaccacgc gcggtcataa      60
aatccgtaat cgcttttttct gcatcaacca                                      90

<210> SEQ ID NO 59
<211> LENGTH: 90
<212> TYPE: DNA
<213> ORGANISM: Artificial
<220> FEATURE:
<223> OTHER INFORMATION: Oligonucleotide

<400> SEQUENCE: 59
ttgtggttgg tggcttttttt ggggacggtt tatattttgc tattaataaa atctatgaga    60
gtcgttttaa cggctctcat agacagagaa                                       90

<210> SEQ ID NO 60
<211> LENGTH: 90
<212> TYPE: DNA
<213> ORGANISM: Artificial
<220> FEATURE:
<223> OTHER INFORMATION: Oligonucleotide

<400> SEQUENCE: 60
gcgatactgt ttagcacatg gagcgatggc gattccggtt tattaacgtc gtgaaaccta     60
```

```
aggacaccat tggaaagcc tgttaaccct                                              90

<210> SEQ ID NO 61
<211> LENGTH: 90
<212> TYPE: DNA
<213> ORGANISM: Artificial
<220> FEATURE:
<223> OTHER INFORMATION: Oligonucleotide

<400> SEQUENCE: 61
ttcggcctgg agcatgccat gttgcgcatt atcgatacag aaactgatgc ggtttgcagg           60
gagggatcgt tgagattgcc tctgttgatg                                            90

<210> SEQ ID NO 62
<211> LENGTH: 90
<212> TYPE: DNA
<213> ORGANISM: Artificial
<220> FEATURE:
<223> OTHER INFORMATION: Oligonucleotide

<400> SEQUENCE: 62
gaatttgatc tcgctcacat gttaccttct caatcccctg caattgattt accgttagtc           60
gcctgaatca aacggttcgt ctgctgcttg                                            90

<210> SEQ ID NO 63
<211> LENGTH: 90
<212> TYPE: DNA
<213> ORGANISM: Artificial
<220> FEATURE:
<223> OTHER INFORMATION: Oligonucleotide

<400> SEQUENCE: 63
ggaggcaatt cagcgggcaa gtctgccgtt tcatcgactt cacgtcacga cgaagttgta           60
tctgttgttt cacgcgaatt atttaccgct                                            90

<210> SEQ ID NO 64
<211> LENGTH: 90
<212> TYPE: DNA
<213> ORGANISM: Artificial
<220> FEATURE:
<223> OTHER INFORMATION: Oligonucleotide

<400> SEQUENCE: 64
aataacggat ttaacctaat gatgaatgac ggtaagcaac aatctgaacc tttttgtttc           60
acgattacga aacctttggc acgcaccccg                                            90

<210> SEQ ID NO 65
<211> LENGTH: 90
<212> TYPE: DNA
<213> ORGANISM: Artificial
<220> FEATURE:
<223> OTHER INFORMATION: Oligonucleotide

<400> SEQUENCE: 65
tgaaacagaa agccgcagag cagaaggtgg cagcatgaca ccgtaacatt atcctgcagc           60
gtaccgggat cgatgtgaga gctgtcgaac                                            90

<210> SEQ ID NO 66
<211> LENGTH: 90
<212> TYPE: DNA
<213> ORGANISM: Artificial
<220> FEATURE:
```

<223> OTHER INFORMATION: Oligonucleotide

<400> SEQUENCE: 66
gcacgcatgg tttaagcaac gaagaacgcc tggagctctg gacattaaac gcggaactgg    60
cgaaaaagtg atttaacggc ttaagtgccg    90

<210> SEQ ID NO 67
<211> LENGTH: 90
<212> TYPE: DNA
<213> ORGANISM: Artificial
<220> FEATURE:
<223> OTHER INFORMATION: Oligonucleotide

<400> SEQUENCE: 67
cgcacgcatg gtttaagcaa cgaagaacgc ctggagctct ggacattaaa ccaggaactg    60
gcggcaaagt gatttaacgg cttaagtgcc    90

<210> SEQ ID NO 68
<211> LENGTH: 92
<212> TYPE: DNA
<213> ORGANISM: Artificial
<220> FEATURE:
<223> OTHER INFORMATION: Oligonucleotide

<400> SEQUENCE: 68
gaatttcagc gacgtttgac tgccgtttga gcagtcatgt gttaaagctt cggccccgtc    60
tgaacgtaag gcaacgtaaa gatacggggtt at    92

<210> SEQ ID NO 69
<211> LENGTH: 90
<212> TYPE: DNA
<213> ORGANISM: Artificial
<220> FEATURE:
<223> OTHER INFORMATION: Oligonucleotide

<400> SEQUENCE: 69
cgcgcagtca gcgatatcca ttttcgcgaa tccggagtgt aagaaaacac accgactaca    60
acgacggttt cgttctgccc tgcgcgattg    90

<210> SEQ ID NO 70
<211> LENGTH: 90
<212> TYPE: DNA
<213> ORGANISM: Artificial
<220> FEATURE:
<223> OTHER INFORMATION: Oligonucleotide

<400> SEQUENCE: 70
cgcgcagtca gcgatatcca ttttcgcgaa tccggagtgt aagaaacgaa actcccgcac    60
tggcacccga tggtcagccg taccgactgt    90

<210> SEQ ID NO 71
<211> LENGTH: 90
<212> TYPE: DNA
<213> ORGANISM: Artificial
<220> FEATURE:
<223> OTHER INFORMATION: Oligonucleotide

<400> SEQUENCE: 71
cgcgcagtca gcgatatcca ttttcgcgaa tccggagtgt aagaacttac catctcgttt    60
tacaggctta acgttaaaac cgacattagc    90

<210> SEQ ID NO 72
<211> LENGTH: 23
<212> TYPE: DNA
<213> ORGANISM: Artificial
<220> FEATURE:
<223> OTHER INFORMATION: Oligonucleotide

<400> SEQUENCE: 72
aaggtggtat ccctggctat tag                                           23

<210> SEQ ID NO 73
<211> LENGTH: 16
<212> TYPE: DNA
<213> ORGANISM: Artificial
<220> FEATURE:
<223> OTHER INFORMATION: Oligonucleotide

<400> SEQUENCE: 73
cggcggtgag gcgtag                                                   16

<210> SEQ ID NO 74
<211> LENGTH: 22
<212> TYPE: DNA
<213> ORGANISM: Artificial
<220> FEATURE:
<223> OTHER INFORMATION: Oligonucleotide

<400> SEQUENCE: 74
ttttgatgag gcgaagcagt ag                                            22

<210> SEQ ID NO 75
<211> LENGTH: 22
<212> TYPE: DNA
<213> ORGANISM: Artificial
<220> FEATURE:
<223> OTHER INFORMATION: Oligonucleotide

<400> SEQUENCE: 75
gttgcgtatt ccggaagagt ag                                            22

<210> SEQ ID NO 76
<211> LENGTH: 22
<212> TYPE: DNA
<213> ORGANISM: Artificial
<220> FEATURE:
<223> OTHER INFORMATION: Oligonucleotide

<400> SEQUENCE: 76
gttaagcatg cgcaaatcgt ag                                            22

<210> SEQ ID NO 77
<211> LENGTH: 22
<212> TYPE: DNA
<213> ORGANISM: Artificial
<220> FEATURE:
<223> OTHER INFORMATION: Oligonucleotide

<400> SEQUENCE: 77
gttgcaggaa ctgcacatct ag                                            22

<210> SEQ ID NO 78
<211> LENGTH: 19
<212> TYPE: DNA
<213> ORGANISM: Artificial
<220> FEATURE:
<223> OTHER INFORMATION: Oligonucleotide

```
<400> SEQUENCE: 78
gctggcgcga gtacagtag                                                  19

<210> SEQ ID NO 79
<211> LENGTH: 29
<212> TYPE: DNA
<213> ORGANISM: Artificial
<220> FEATURE:
<223> OTHER INFORMATION: Oligonucleotide

<400> SEQUENCE: 79
ggtttgtctc cggttttatc tatcaatag                                       29

<210> SEQ ID NO 80
<211> LENGTH: 26
<212> TYPE: DNA
<213> ORGANISM: Artificial
<220> FEATURE:
<223> OTHER INFORMATION: Oligonucleotide

<400> SEQUENCE: 80
gattgttgaa aacattgccg atgtag                                          26

<210> SEQ ID NO 81
<211> LENGTH: 26
<212> TYPE: DNA
<213> ORGANISM: Artificial
<220> FEATURE:
<223> OTHER INFORMATION: Oligonucleotide

<400> SEQUENCE: 81
ccagtaatgg ggaagattta gagtag                                          26

<210> SEQ ID NO 82
<211> LENGTH: 26
<212> TYPE: DNA
<213> ORGANISM: Artificial
<220> FEATURE:
<223> OTHER INFORMATION: Oligonucleotide

<400> SEQUENCE: 82
agtacataaa ccttgccttg ttgtag                                          26

<210> SEQ ID NO 83
<211> LENGTH: 18
<212> TYPE: DNA
<213> ORGANISM: Artificial
<220> FEATURE:
<223> OTHER INFORMATION: Oligonucleotide

<400> SEQUENCE: 83
gcggcaaaac gctggtag                                                   18

<210> SEQ ID NO 84
<211> LENGTH: 25
<212> TYPE: DNA
<213> ORGANISM: Artificial
<220> FEATURE:
<223> OTHER INFORMATION: Oligonucleotide

<400> SEQUENCE: 84
aaggcatacg cgttttttc attag                                            25

<210> SEQ ID NO 85
<211> LENGTH: 20
```

<210> SEQ ID NO 85
<211> LENGTH: 20
<212> TYPE: DNA
<213> ORGANISM: Artificial
<220> FEATURE:
<223> OTHER INFORMATION: Oligonucleotide

<400> SEQUENCE: 85
ccaaacgtcg gctggattag                                          20

<210> SEQ ID NO 86
<211> LENGTH: 26
<212> TYPE: DNA
<213> ORGANISM: Artificial
<220> FEATURE:
<223> OTHER INFORMATION: Oligonucleotide

<400> SEQUENCE: 86
aaggattatc gcaaaggagt ttgtag                                   26

<210> SEQ ID NO 87
<211> LENGTH: 24
<212> TYPE: DNA
<213> ORGANISM: Artificial
<220> FEATURE:
<223> OTHER INFORMATION: Oligonucleotide

<400> SEQUENCE: 87
ttagttatac tcccggccaa ctag                                     24

<210> SEQ ID NO 88
<211> LENGTH: 26
<212> TYPE: DNA
<213> ORGANISM: Artificial
<220> FEATURE:
<223> OTHER INFORMATION: Oligonucleotide

<400> SEQUENCE: 88
cgctggatcc gaaaattaaa ggatag                                   26

<210> SEQ ID NO 89
<211> LENGTH: 33
<212> TYPE: DNA
<213> ORGANISM: Artificial
<220> FEATURE:
<223> OTHER INFORMATION: Oligonucleotide

<400> SEQUENCE: 89
tgggataaaa gtggaaaatt agtaaaagag tag                           33

<210> SEQ ID NO 90
<211> LENGTH: 20
<212> TYPE: DNA
<213> ORGANISM: Artificial
<220> FEATURE:
<223> OTHER INFORMATION: Oligonucleotide

<400> SEQUENCE: 90
ttgagagggt tgcagggtag                                          20

<210> SEQ ID NO 91
<211> LENGTH: 20
<212> TYPE: DNA
<213> ORGANISM: Artificial
<220> FEATURE:
<223> OTHER INFORMATION: Oligonucleotide

<400> SEQUENCE: 91

```
gcctgaaaac gggtggttag                                              20

<210> SEQ ID NO 92
<211> LENGTH: 28
<212> TYPE: DNA
<213> ORGANISM: Artificial
<220> FEATURE:
<223> OTHER INFORMATION: Oligonucleotide

<400> SEQUENCE: 92
agcgaaggaa aggtatactg aaatttag                                     28

<210> SEQ ID NO 93
<211> LENGTH: 26
<212> TYPE: DNA
<213> ORGANISM: Artificial
<220> FEATURE:
<223> OTHER INFORMATION: Oligonucleotide

<400> SEQUENCE: 93
tcatcgacaa tatctggcca atttag                                       26

<210> SEQ ID NO 94
<211> LENGTH: 22
<212> TYPE: DNA
<213> ORGANISM: Artificial
<220> FEATURE:
<223> OTHER INFORMATION: Oligonucleotide

<400> SEQUENCE: 94
tgcacaagcc ttgttcagtt ag                                           22

<210> SEQ ID NO 95
<211> LENGTH: 26
<212> TYPE: DNA
<213> ORGANISM: Artificial
<220> FEATURE:
<223> OTHER INFORMATION: Oligonucleotide

<400> SEQUENCE: 95
cagaaatcgc ggcgttaatt aattag                                       26

<210> SEQ ID NO 96
<211> LENGTH: 15
<212> TYPE: DNA
<213> ORGANISM: Artificial
<220> FEATURE:
<223> OTHER INFORMATION: Oligonucleotide

<400> SEQUENCE: 96
ggcgcgccgg tttag                                                   15

<210> SEQ ID NO 97
<211> LENGTH: 22
<212> TYPE: DNA
<213> ORGANISM: Artificial
<220> FEATURE:
<223> OTHER INFORMATION: Oligonucleotide

<400> SEQUENCE: 97
gctggagatg aacctgagtt ag                                           22

<210> SEQ ID NO 98
<211> LENGTH: 24
<212> TYPE: DNA
<213> ORGANISM: Artificial
```

```
<220> FEATURE:
<223> OTHER INFORMATION: Oligonucleotide

<400> SEQUENCE: 98
ctcgaagcgt atgacctgat ttag                                          24

<210> SEQ ID NO 99
<211> LENGTH: 19
<212> TYPE: DNA
<213> ORGANISM: Artificial
<220> FEATURE:
<223> OTHER INFORMATION: Oligonucleotide

<400> SEQUENCE: 99
cgcgcgtggt tatcactag                                                19

<210> SEQ ID NO 100
<211> LENGTH: 27
<212> TYPE: DNA
<213> ORGANISM: Artificial
<220> FEATURE:
<223> OTHER INFORMATION: Oligonucleotide

<400> SEQUENCE: 100
tggggacggt ttatattttg ctattag                                       27

<210> SEQ ID NO 101
<211> LENGTH: 18
<212> TYPE: DNA
<213> ORGANISM: Artificial
<220> FEATURE:
<223> OTHER INFORMATION: Oligonucleotide

<400> SEQUENCE: 101
gcaatggccg caggaagg                                                 18

<210> SEQ ID NO 102
<211> LENGTH: 23
<212> TYPE: DNA
<213> ORGANISM: Artificial
<220> FEATURE:
<223> OTHER INFORMATION: Oligonucleotide

<400> SEQUENCE: 102
gcacggtacg atgggtaata gat                                           23

<210> SEQ ID NO 103
<211> LENGTH: 21
<212> TYPE: DNA
<213> ORGANISM: Artificial
<220> FEATURE:
<223> OTHER INFORMATION: Oligonucleotide

<400> SEQUENCE: 103
gaagtcatga agcaaggcag a                                             21

<210> SEQ ID NO 104
<211> LENGTH: 20
<212> TYPE: DNA
<213> ORGANISM: Artificial
<220> FEATURE:
<223> OTHER INFORMATION: Oligonucleotide

<400> SEQUENCE: 104
cggcaggtat gcaaagcaga                                               20
```

```
<210> SEQ ID NO 105
<211> LENGTH: 25
<212> TYPE: DNA
<213> ORGANISM: Artificial
<220> FEATURE:
<223> OTHER INFORMATION: Oligonucleotide

<400> SEQUENCE: 105
agtatgggac ttaatgttcg agagg                                          25

<210> SEQ ID NO 106
<211> LENGTH: 17
<212> TYPE: DNA
<213> ORGANISM: Artificial
<220> FEATURE:
<223> OTHER INFORMATION: Oligonucleotide

<400> SEQUENCE: 106
agggcgaatc ggcaagg                                                   17

<210> SEQ ID NO 107
<211> LENGTH: 24
<212> TYPE: DNA
<213> ORGANISM: Artificial
<220> FEATURE:
<223> OTHER INFORMATION: Oligonucleotide

<400> SEQUENCE: 107
gaaaaatatg gtgctgccga aaga                                           24

<210> SEQ ID NO 108
<211> LENGTH: 33
<212> TYPE: DNA
<213> ORGANISM: Artificial
<220> FEATURE:
<223> OTHER INFORMATION: Oligonucleotide

<400> SEQUENCE: 108
cttcttacgc cacttattat tcttatctta aga                                 33

<210> SEQ ID NO 109
<211> LENGTH: 17
<212> TYPE: DNA
<213> ORGANISM: Artificial
<220> FEATURE:
<223> OTHER INFORMATION: Oligonucleotide

<400> SEQUENCE: 109
tggctggtga ggccaga                                                   17

<210> SEQ ID NO 110
<211> LENGTH: 23
<212> TYPE: DNA
<213> ORGANISM: Artificial
<220> FEATURE:
<223> OTHER INFORMATION: Oligonucleotide

<400> SEQUENCE: 110
gcgcattatc gatacagaaa cct                                            23

<210> SEQ ID NO 111
<211> LENGTH: 26
<212> TYPE: DNA
<213> ORGANISM: Artificial
<220> FEATURE:
<223> OTHER INFORMATION: Oligonucleotide
```

<400> SEQUENCE: 111
cttctcaatc ccctgcaatt tttacc    26

<210> SEQ ID NO 112
<211> LENGTH: 22
<212> TYPE: DNA
<213> ORGANISM: Artificial
<220> FEATURE:
<223> OTHER INFORMATION: Oligonucleotide

<400> SEQUENCE: 112
caacagatac aacttcgtcg cc    22

<210> SEQ ID NO 113
<211> LENGTH: 25
<212> TYPE: DNA
<213> ORGANISM: Artificial
<220> FEATURE:
<223> OTHER INFORMATION: Oligonucleotide

<400> SEQUENCE: 113
gaatgacggt aagcaacaat ctacc    25

<210> SEQ ID NO 114
<211> LENGTH: 17
<212> TYPE: DNA
<213> ORGANISM: Artificial
<220> FEATURE:
<223> OTHER INFORMATION: Oligonucleotide

<400> SEQUENCE: 114
ggcagcatga caccgga    17

<210> SEQ ID NO 115
<211> LENGTH: 22
<212> TYPE: DNA
<213> ORGANISM: Artificial
<220> FEATURE:
<223> OTHER INFORMATION: Oligonucleotide

<400> SEQUENCE: 115
tggagctctg gacattaaac ca    22

<210> SEQ ID NO 116
<211> LENGTH: 22
<212> TYPE: DNA
<213> ORGANISM: Artificial
<220> FEATURE:
<223> OTHER INFORMATION: Oligonucleotide

<400> SEQUENCE: 116
cattaaacca ggaactggcg aa    22

<210> SEQ ID NO 117
<211> LENGTH: 23
<212> TYPE: DNA
<213> ORGANISM: Artificial
<220> FEATURE:
<223> OTHER INFORMATION: Oligonucleotide

<400> SEQUENCE: 117
aaggtggtat ccctggctat taa    23

<210> SEQ ID NO 118

```
<211> LENGTH: 16
<212> TYPE: DNA
<213> ORGANISM: Artificial
<220> FEATURE:
<223> OTHER INFORMATION: Oligonucleotide

<400> SEQUENCE: 118
cggcggtgag gcgtaa                                                     16

<210> SEQ ID NO 119
<211> LENGTH: 22
<212> TYPE: DNA
<213> ORGANISM: Artificial
<220> FEATURE:
<223> OTHER INFORMATION: Oligonucleotide

<400> SEQUENCE: 119
ttttgatgag gcgaagcagt aa                                              22

<210> SEQ ID NO 120
<211> LENGTH: 22
<212> TYPE: DNA
<213> ORGANISM: Artificial
<220> FEATURE:
<223> OTHER INFORMATION: Oligonucleotide

<400> SEQUENCE: 120
gttgcgtatt ccggaagagt aa                                              22

<210> SEQ ID NO 121
<211> LENGTH: 22
<212> TYPE: DNA
<213> ORGANISM: Artificial
<220> FEATURE:
<223> OTHER INFORMATION: Oligonucleotide

<400> SEQUENCE: 121
gttaagcatg cgcaaatcgt aa                                              22

<210> SEQ ID NO 122
<211> LENGTH: 22
<212> TYPE: DNA
<213> ORGANISM: Artificial
<220> FEATURE:
<223> OTHER INFORMATION: Oligonucleotide

<400> SEQUENCE: 122
gttgcaggaa ctgcacatct aa                                              22

<210> SEQ ID NO 123
<211> LENGTH: 19
<212> TYPE: DNA
<213> ORGANISM: Artificial
<220> FEATURE:
<223> OTHER INFORMATION: Oligonucleotide

<400> SEQUENCE: 123
gctggcgcga gtacagtaa                                                  19

<210> SEQ ID NO 124
<211> LENGTH: 29
<212> TYPE: DNA
<213> ORGANISM: Artificial
<220> FEATURE:
<223> OTHER INFORMATION: Oligonucleotide

<400> SEQUENCE: 124
```
ggtttgtctc cggttttatc tatcaataa                                         29

<210> SEQ ID NO 125
<211> LENGTH: 26
<212> TYPE: DNA
<213> ORGANISM: Artificial
<220> FEATURE:
<223> OTHER INFORMATION: Oligonucleotide

<400> SEQUENCE: 125
gattgttgaa aacattgccg atgtaa                                            26

<210> SEQ ID NO 126
<211> LENGTH: 26
<212> TYPE: DNA
<213> ORGANISM: Artificial
<220> FEATURE:
<223> OTHER INFORMATION: Oligonucleotide

<400> SEQUENCE: 126
ccagtaatgg ggaagattta gagtaa                                            26

<210> SEQ ID NO 127
<211> LENGTH: 26
<212> TYPE: DNA
<213> ORGANISM: Artificial
<220> FEATURE:
<223> OTHER INFORMATION: Oligonucleotide

<400> SEQUENCE: 127
agtacataaa ccttgccttg ttgtaa                                            26

<210> SEQ ID NO 128
<211> LENGTH: 18
<212> TYPE: DNA
<213> ORGANISM: Artificial
<220> FEATURE:
<223> OTHER INFORMATION: Oligonucleotide

<400> SEQUENCE: 128
gcggcaaaac gctggtaa                                                     18

<210> SEQ ID NO 129
<211> LENGTH: 25
<212> TYPE: DNA
<213> ORGANISM: Artificial
<220> FEATURE:
<223> OTHER INFORMATION: Oligonucleotide

<400> SEQUENCE: 129
aaggcatacg cgttttttc attaa                                              25

<210> SEQ ID NO 130
<211> LENGTH: 20
<212> TYPE: DNA
<213> ORGANISM: Artificial
<220> FEATURE:
<223> OTHER INFORMATION: Oligonucleotide

<400> SEQUENCE: 130
ccaaacgtcg gctggattaa                                                   20

<210> SEQ ID NO 131
<211> LENGTH: 26
<212> TYPE: DNA

```
<213> ORGANISM: Artificial
<220> FEATURE:
<223> OTHER INFORMATION: Oligonucleotide

<400> SEQUENCE: 131
aaggattatc gcaaaggagt ttgtaa                                          26

<210> SEQ ID NO 132
<211> LENGTH: 24
<212> TYPE: DNA
<213> ORGANISM: Artificial
<220> FEATURE:
<223> OTHER INFORMATION: Oligonucleotide

<400> SEQUENCE: 132
ttagttatac tcccggccaa ctaa                                            24

<210> SEQ ID NO 133
<211> LENGTH: 26
<212> TYPE: DNA
<213> ORGANISM: Artificial
<220> FEATURE:
<223> OTHER INFORMATION: Oligonucleotide

<400> SEQUENCE: 133
cgctggatcc gaaaattaaa ggataa                                          26

<210> SEQ ID NO 134
<211> LENGTH: 33
<212> TYPE: DNA
<213> ORGANISM: Artificial
<220> FEATURE:
<223> OTHER INFORMATION: Oligonucleotide

<400> SEQUENCE: 134
tgggataaaa gtggaaaatt agtaaaagag taa                                  33

<210> SEQ ID NO 135
<211> LENGTH: 20
<212> TYPE: DNA
<213> ORGANISM: Artificial
<220> FEATURE:
<223> OTHER INFORMATION: Oligonucleotide

<400> SEQUENCE: 135
ttgagagggt tgcagggtaa                                                 20

<210> SEQ ID NO 136
<211> LENGTH: 20
<212> TYPE: DNA
<213> ORGANISM: Artificial
<220> FEATURE:
<223> OTHER INFORMATION: Oligonucleotide

<400> SEQUENCE: 136
gcctgaaaac gggtggttaa                                                 20

<210> SEQ ID NO 137
<211> LENGTH: 28
<212> TYPE: DNA
<213> ORGANISM: Artificial
<220> FEATURE:
<223> OTHER INFORMATION: Oligonucleotide

<400> SEQUENCE: 137
agcgaaggaa aggtatactg aaatttaa                                        28
```

<210> SEQ ID NO 138
<211> LENGTH: 26
<212> TYPE: DNA
<213> ORGANISM: Artificial
<220> FEATURE:
<223> OTHER INFORMATION: Oligonucleotide

<400> SEQUENCE: 138
tcatcgacaa tatctggcca atttaa                                          26

<210> SEQ ID NO 139
<211> LENGTH: 22
<212> TYPE: DNA
<213> ORGANISM: Artificial
<220> FEATURE:
<223> OTHER INFORMATION: Oligonucleotide

<400> SEQUENCE: 139
tgcacaagcc ttgttcagtt aa                                              22

<210> SEQ ID NO 140
<211> LENGTH: 26
<212> TYPE: DNA
<213> ORGANISM: Artificial
<220> FEATURE:
<223> OTHER INFORMATION: Oligonucleotide

<400> SEQUENCE: 140
cagaaatcgc ggcgttaatt aattaa                                          26

<210> SEQ ID NO 141
<211> LENGTH: 15
<212> TYPE: DNA
<213> ORGANISM: Artificial
<220> FEATURE:
<223> OTHER INFORMATION: Oligonucleotide

<400> SEQUENCE: 141
ggcgcgccgg tttaa                                                      15

<210> SEQ ID NO 142
<211> LENGTH: 22
<212> TYPE: DNA
<213> ORGANISM: Artificial
<220> FEATURE:
<223> OTHER INFORMATION: Oligonucleotide

<400> SEQUENCE: 142
gctggagatg aacctgagtt aa                                              22

<210> SEQ ID NO 143
<211> LENGTH: 24
<212> TYPE: DNA
<213> ORGANISM: Artificial
<220> FEATURE:
<223> OTHER INFORMATION: Oligonucleotide

<400> SEQUENCE: 143
ctcgaagcgt atgacctgat ttaa                                            24

<210> SEQ ID NO 144
<211> LENGTH: 19
<212> TYPE: DNA
<213> ORGANISM: Artificial
<220> FEATURE:

<223> OTHER INFORMATION: Oligonucleotide

<400> SEQUENCE: 144
cgcgcgtggt tatcactaa                                                    19

<210> SEQ ID NO 145
<211> LENGTH: 27
<212> TYPE: DNA
<213> ORGANISM: Artificial
<220> FEATURE:
<223> OTHER INFORMATION: Oligonucleotide

<400> SEQUENCE: 145
tggggacggt ttatattttg ctattaa                                           27

<210> SEQ ID NO 146
<211> LENGTH: 23
<212> TYPE: DNA
<213> ORGANISM: Artificial
<220> FEATURE:
<223> OTHER INFORMATION: Oligonucleotide

<400> SEQUENCE: 146
cgatggcgat tccggtttat taa                                               23

<210> SEQ ID NO 147
<211> LENGTH: 21
<212> TYPE: DNA
<213> ORGANISM: Artificial
<220> FEATURE:
<223> OTHER INFORMATION: Oligonucleotide

<400> SEQUENCE: 147
gctgccggat tatcatcaag g                                                 21

<210> SEQ ID NO 148
<211> LENGTH: 18
<212> TYPE: DNA
<213> ORGANISM: Artificial
<220> FEATURE:
<223> OTHER INFORMATION: Oligonucleotide

<400> SEQUENCE: 148
gcaatggccg caggaaga                                                     18

<210> SEQ ID NO 149
<211> LENGTH: 23
<212> TYPE: DNA
<213> ORGANISM: Artificial
<220> FEATURE:
<223> OTHER INFORMATION: Oligonucleotide

<400> SEQUENCE: 149
gcacggtacg atgggtaata gac                                               23

<210> SEQ ID NO 150
<211> LENGTH: 21
<212> TYPE: DNA
<213> ORGANISM: Artificial
<220> FEATURE:
<223> OTHER INFORMATION: Oligonucleotide

<400> SEQUENCE: 150
gaagtcatga agcaaggcag g                                                 21

```
<210> SEQ ID NO 151
<211> LENGTH: 19
<212> TYPE: DNA
<213> ORGANISM: Artificial
<220> FEATURE:
<223> OTHER INFORMATION: Oligonucleotide

<400> SEQUENCE: 151
ggcaggtatg caaagcagg                                              19

<210> SEQ ID NO 152
<211> LENGTH: 26
<212> TYPE: DNA
<213> ORGANISM: Artificial
<220> FEATURE:
<223> OTHER INFORMATION: Oligonucleotide

<400> SEQUENCE: 152
gagtatggga cttaatgttc gagaga                                      26

<210> SEQ ID NO 153
<211> LENGTH: 18
<212> TYPE: DNA
<213> ORGANISM: Artificial
<220> FEATURE:
<223> OTHER INFORMATION: Oligonucleotide

<400> SEQUENCE: 153
gagggcgaat cggcaaga                                               18

<210> SEQ ID NO 154
<211> LENGTH: 22
<212> TYPE: DNA
<213> ORGANISM: Artificial
<220> FEATURE:
<223> OTHER INFORMATION: Oligonucleotide

<400> SEQUENCE: 154
aaaatatggt gctgccgaaa gg                                          22

<210> SEQ ID NO 155
<211> LENGTH: 33
<212> TYPE: DNA
<213> ORGANISM: Artificial
<220> FEATURE:
<223> OTHER INFORMATION: Oligonucleotide

<400> SEQUENCE: 155
cttcttacgc cacttattat tcttatctta agg                              33

<210> SEQ ID NO 156
<211> LENGTH: 16
<212> TYPE: DNA
<213> ORGANISM: Artificial
<220> FEATURE:
<223> OTHER INFORMATION: Oligonucleotide

<400> SEQUENCE: 156
ggctggtgag gccagg                                                 16

<210> SEQ ID NO 157
<211> LENGTH: 24
<212> TYPE: DNA
<213> ORGANISM: Artificial
<220> FEATURE:
<223> OTHER INFORMATION: Oligonucleotide
```

<400> SEQUENCE: 157
gcgcattatc gatacagaaa ctga                                          24

<210> SEQ ID NO 158
<211> LENGTH: 22
<212> TYPE: DNA
<213> ORGANISM: Artificial
<220> FEATURE:
<223> OTHER INFORMATION: Oligonucleotide

<400> SEQUENCE: 158
cttctcaatc ccctgcaatt ga                                            22

<210> SEQ ID NO 159
<211> LENGTH: 23
<212> TYPE: DNA
<213> ORGANISM: Artificial
<220> FEATURE:
<223> OTHER INFORMATION: Oligonucleotide

<400> SEQUENCE: 159
caacagatac aacttcgtcg tga                                           23

<210> SEQ ID NO 160
<211> LENGTH: 24
<212> TYPE: DNA
<213> ORGANISM: Artificial
<220> FEATURE:
<223> OTHER INFORMATION: Oligonucleotide

<400> SEQUENCE: 160
gaatgacggt aagcaacaat ctga                                          24

<210> SEQ ID NO 161
<211> LENGTH: 19
<212> TYPE: DNA
<213> ORGANISM: Artificial
<220> FEATURE:
<223> OTHER INFORMATION: Oligonucleotide

<400> SEQUENCE: 161
tggcagcatg acaccgtaa                                                19

<210> SEQ ID NO 162
<211> LENGTH: 21
<212> TYPE: DNA
<213> ORGANISM: Artificial
<220> FEATURE:
<223> OTHER INFORMATION: Oligonucleotide

<400> SEQUENCE: 162
ggagctctgg acattaaacg c                                             21

<210> SEQ ID NO 163
<211> LENGTH: 16
<212> TYPE: DNA
<213> ORGANISM: Artificial
<220> FEATURE:
<223> OTHER INFORMATION: Oligonucleotide

<400> SEQUENCE: 163
accaggaact ggcggc                                                   16

<210> SEQ ID NO 164
<211> LENGTH: 28

```
<212> TYPE: DNA
<213> ORGANISM: Artificial
<220> FEATURE:
<223> OTHER INFORMATION: Oligonucleotide

<400> SEQUENCE: 164
taggtagagc aacctttatt aagctacg                                          28

<210> SEQ ID NO 165
<211> LENGTH: 31
<212> TYPE: DNA
<213> ORGANISM: Artificial
<220> FEATURE:
<223> OTHER INFORMATION: Oligonucleotide

<400> SEQUENCE: 165
taaaaatatc tacatttctg aaaaatgcgc a                                      31

<210> SEQ ID NO 166
<211> LENGTH: 16
<212> TYPE: DNA
<213> ORGANISM: Artificial
<220> FEATURE:
<223> OTHER INFORMATION: Oligonucleotide

<400> SEQUENCE: 166
gcggcgatgt tggctt                                                       16

<210> SEQ ID NO 167
<211> LENGTH: 16
<212> TYPE: DNA
<213> ORGANISM: Artificial
<220> FEATURE:
<223> OTHER INFORMATION: Oligonucleotide

<400> SEQUENCE: 167
agggtatcgg gtggcg                                                       16

<210> SEQ ID NO 168
<211> LENGTH: 16
<212> TYPE: DNA
<213> ORGANISM: Artificial
<220> FEATURE:
<223> OTHER INFORMATION: Oligonucleotide

<400> SEQUENCE: 168
cgcaacgctt ctgccg                                                       16

<210> SEQ ID NO 169
<211> LENGTH: 18
<212> TYPE: DNA
<213> ORGANISM: Artificial
<220> FEATURE:
<223> OTHER INFORMATION: Oligonucleotide

<400> SEQUENCE: 169
atgcccaggc gatgtaca                                                     18

<210> SEQ ID NO 170
<211> LENGTH: 20
<212> TYPE: DNA
<213> ORGANISM: Artificial
<220> FEATURE:
<223> OTHER INFORMATION: Oligonucleotide

<400> SEQUENCE: 170
```
agactcggca gttgttacgg    20

<210> SEQ ID NO 171
<211> LENGTH: 21
<212> TYPE: DNA
<213> ORGANISM: Artificial
<220> FEATURE:
<223> OTHER INFORMATION: Oligonucleotide

<400> SEQUENCE: 171
ggatggagtg cacctttcaa c    21

<210> SEQ ID NO 172
<211> LENGTH: 22
<212> TYPE: DNA
<213> ORGANISM: Artificial
<220> FEATURE:
<223> OTHER INFORMATION: Oligonucleotide

<400> SEQUENCE: 172
gtgttgcatt tggacaccat tg    22

<210> SEQ ID NO 173
<211> LENGTH: 19
<212> TYPE: DNA
<213> ORGANISM: Artificial
<220> FEATURE:
<223> OTHER INFORMATION: Oligonucleotide

<400> SEQUENCE: 173
cgcttatcgg gccttcatg    19

<210> SEQ ID NO 174
<211> LENGTH: 23
<212> TYPE: DNA
<213> ORGANISM: Artificial
<220> FEATURE:
<223> OTHER INFORMATION: Oligonucleotide

<400> SEQUENCE: 174
cgggaagaac tctttcattt cgc    23

<210> SEQ ID NO 175
<211> LENGTH: 23
<212> TYPE: DNA
<213> ORGANISM: Artificial
<220> FEATURE:
<223> OTHER INFORMATION: Oligonucleotide

<400> SEQUENCE: 175
cgtcaatccg acaaagacaa tca    23

<210> SEQ ID NO 176
<211> LENGTH: 25
<212> TYPE: DNA
<213> ORGANISM: Artificial
<220> FEATURE:
<223> OTHER INFORMATION: Oligonucleotide

<400> SEQUENCE: 176
ttactggcag ggattatctt taccg    25

<210> SEQ ID NO 177
<211> LENGTH: 24
<212> TYPE: DNA
<213> ORGANISM: Artificial

```
<220> FEATURE:
<223> OTHER INFORMATION: Oligonucleotide

<400> SEQUENCE: 177
ctgttgttag gtttcggttt tcct                                              24

<210> SEQ ID NO 178
<211> LENGTH: 17
<212> TYPE: DNA
<213> ORGANISM: Artificial
<220> FEATURE:
<223> OTHER INFORMATION: Oligonucleotide

<400> SEQUENCE: 178
gtcataggcg gcttgcg                                                      17

<210> SEQ ID NO 179
<211> LENGTH: 19
<212> TYPE: DNA
<213> ORGANISM: Artificial
<220> FEATURE:
<223> OTHER INFORMATION: Oligonucleotide

<400> SEQUENCE: 179
atgagccggt aaaagcgac                                                    19

<210> SEQ ID NO 180
<211> LENGTH: 39
<212> TYPE: DNA
<213> ORGANISM: Artificial
<220> FEATURE:
<223> OTHER INFORMATION: Oligonucleotide

<400> SEQUENCE: 180
aataaaatta tcagccttat ctttatcttt tcgtataaa                              39

<210> SEQ ID NO 181
<211> LENGTH: 20
<212> TYPE: DNA
<213> ORGANISM: Artificial
<220> FEATURE:
<223> OTHER INFORMATION: Oligonucleotide

<400> SEQUENCE: 181
cagcaatatt tgccaccgca                                                   20

<210> SEQ ID NO 182
<211> LENGTH: 19
<212> TYPE: DNA
<213> ORGANISM: Artificial
<220> FEATURE:
<223> OTHER INFORMATION: Oligonucleotide

<400> SEQUENCE: 182
aacttttccg cagggcatc                                                    19

<210> SEQ ID NO 183
<211> LENGTH: 26
<212> TYPE: DNA
<213> ORGANISM: Artificial
<220> FEATURE:
<223> OTHER INFORMATION: Oligonucleotide

<400> SEQUENCE: 183
tacaacctct ttcgataaaa agaccg                                            26
```

```
<210> SEQ ID NO 184
<211> LENGTH: 20
<212> TYPE: DNA
<213> ORGANISM: Artificial
<220> FEATURE:
<223> OTHER INFORMATION: Oligonucleotide

<400> SEQUENCE: 184
gatgaactgt tgcatcggcg                                               20

<210> SEQ ID NO 185
<211> LENGTH: 16
<212> TYPE: DNA
<213> ORGANISM: Artificial
<220> FEATURE:
<223> OTHER INFORMATION: Oligonucleotide

<400> SEQUENCE: 185
ctgtacgcag ccagcc                                                   16

<210> SEQ ID NO 186
<211> LENGTH: 17
<212> TYPE: DNA
<213> ORGANISM: Artificial
<220> FEATURE:
<223> OTHER INFORMATION: Oligonucleotide

<400> SEQUENCE: 186
aatcgctgcc ttacgcg                                                  17

<210> SEQ ID NO 187
<211> LENGTH: 19
<212> TYPE: DNA
<213> ORGANISM: Artificial
<220> FEATURE:
<223> OTHER INFORMATION: Oligonucleotide

<400> SEQUENCE: 187
taaccaaagc caccagtgc                                                19

<210> SEQ ID NO 188
<211> LENGTH: 25
<212> TYPE: DNA
<213> ORGANISM: Artificial
<220> FEATURE:
<223> OTHER INFORMATION: Oligonucleotide

<400> SEQUENCE: 188
cgcgagatat tttttcatca ttccg                                         25

<210> SEQ ID NO 189
<211> LENGTH: 18
<212> TYPE: DNA
<213> ORGANISM: Artificial
<220> FEATURE:
<223> OTHER INFORMATION: Oligonucleotide

<400> SEQUENCE: 189
gggcaaaatt gctgtggc                                                 18

<210> SEQ ID NO 190
<211> LENGTH: 22
<212> TYPE: DNA
<213> ORGANISM: Artificial
<220> FEATURE:
<223> OTHER INFORMATION: Oligonucleotide
```

```
<400> SEQUENCE: 190
accaactggc gatgttattc ac                                    22

<210> SEQ ID NO 191
<211> LENGTH: 18
<212> TYPE: DNA
<213> ORGANISM: Artificial
<220> FEATURE:
<223> OTHER INFORMATION: Oligonucleotide

<400> SEQUENCE: 191
gacgatggtg gtggacgg                                         18

<210> SEQ ID NO 192
<211> LENGTH: 19
<212> TYPE: DNA
<213> ORGANISM: Artificial
<220> FEATURE:
<223> OTHER INFORMATION: Oligonucleotide

<400> SEQUENCE: 192
atcgccaaat tgcatggca                                        19

<210> SEQ ID NO 193
<211> LENGTH: 21
<212> TYPE: DNA
<213> ORGANISM: Artificial
<220> FEATURE:
<223> OTHER INFORMATION: Oligonucleotide

<400> SEQUENCE: 193
aaaatcctga ctctggcctc a                                     21

<210> SEQ ID NO 194
<211> LENGTH: 20
<212> TYPE: DNA
<213> ORGANISM: Artificial
<220> FEATURE:
<223> OTHER INFORMATION: Oligonucleotide

<400> SEQUENCE: 194
tctgtttgca ctgcgggtac                                       20

<210> SEQ ID NO 195
<211> LENGTH: 26
<212> TYPE: DNA
<213> ORGANISM: Artificial
<220> FEATURE:
<223> OTHER INFORMATION: Oligonucleotide

<400> SEQUENCE: 195
tggttgggca atctaataga ttctcc                                26

<210> SEQ ID NO 196
<211> LENGTH: 22
<212> TYPE: DNA
<213> ORGANISM: Artificial
<220> FEATURE:
<223> OTHER INFORMATION: Oligonucleotide

<400> SEQUENCE: 196
atgagcgtaa tcatcgtcgg tg                                    22

<210> SEQ ID NO 197
```

```
<211> LENGTH: 17
<212> TYPE: DNA
<213> ORGANISM: Artificial
<220> FEATURE:
<223> OTHER INFORMATION: Oligonucleotide

<400> SEQUENCE: 197
ccgtctctcg ccagctg                                                    17

<210> SEQ ID NO 198
<211> LENGTH: 20
<212> TYPE: DNA
<213> ORGANISM: Artificial
<220> FEATURE:
<223> OTHER INFORMATION: Oligonucleotide

<400> SEQUENCE: 198
agcacacgac gtttctttcg                                                 20

<210> SEQ ID NO 199
<211> LENGTH: 24
<212> TYPE: DNA
<213> ORGANISM: Artificial
<220> FEATURE:
<223> OTHER INFORMATION: Oligonucleotide

<400> SEQUENCE: 199
atctgttctt ccgatgtacc ttcc                                            24

<210> SEQ ID NO 200
<211> LENGTH: 22
<212> TYPE: DNA
<213> ORGANISM: Artificial
<220> FEATURE:
<223> OTHER INFORMATION: Oligonucleotide

<400> SEQUENCE: 200
cttccagctc gatatcgtgg ag                                              22

<210> SEQ ID NO 201
<211> LENGTH: 22
<212> TYPE: DNA
<213> ORGANISM: Artificial
<220> FEATURE:
<223> OTHER INFORMATION: Oligonucleotide

<400> SEQUENCE: 201
caccaccaaa ggttaactgt gg                                              22

<210> SEQ ID NO 202
<211> LENGTH: 23
<212> TYPE: DNA
<213> ORGANISM: Artificial
<220> FEATURE:
<223> OTHER INFORMATION: Oligonucleotide

<400> SEQUENCE: 202
cacaaaccag acaaataccg agc                                             23

<210> SEQ ID NO 203
<211> LENGTH: 23
<212> TYPE: DNA
<213> ORGANISM: Artificial
<220> FEATURE:
<223> OTHER INFORMATION: Oligonucleotide

<400> SEQUENCE: 203
```

```
cgatggtatc cagcgtaaag ttg                                              23

<210> SEQ ID NO 204
<211> LENGTH: 19
<212> TYPE: DNA
<213> ORGANISM: Artificial
<220> FEATURE:
<223> OTHER INFORMATION: Oligonucleotide

<400> SEQUENCE: 204
gaccatggct tcggtgatg                                                   19

<210> SEQ ID NO 205
<211> LENGTH: 25
<212> TYPE: DNA
<213> ORGANISM: Artificial
<220> FEATURE:
<223> OTHER INFORMATION: Oligonucleotide

<400> SEQUENCE: 205
ggtacgctta agttgatttt ccagc                                            25

<210> SEQ ID NO 206
<211> LENGTH: 19
<212> TYPE: DNA
<213> ORGANISM: Artificial
<220> FEATURE:
<223> OTHER INFORMATION: Oligonucleotide

<400> SEQUENCE: 206
ggcctgatcg accacttcc                                                   19

<210> SEQ ID NO 207
<211> LENGTH: 23
<212> TYPE: DNA
<213> ORGANISM: Artificial
<220> FEATURE:
<223> OTHER INFORMATION: Oligonucleotide

<400> SEQUENCE: 207
gaaatgtctc ctgccaaatc cac                                              23

<210> SEQ ID NO 208
<211> LENGTH: 16
<212> TYPE: DNA
<213> ORGANISM: Artificial
<220> FEATURE:
<223> OTHER INFORMATION: Oligonucleotide

<400> SEQUENCE: 208
caaggccgtt gccgtc                                                      16

<210> SEQ ID NO 209
<211> LENGTH: 22
<212> TYPE: DNA
<213> ORGANISM: Artificial
<220> FEATURE:
<223> OTHER INFORMATION: Oligonucleotide

<400> SEQUENCE: 209
gctccataag acggtatcca ca                                               22

<210> SEQ ID NO 210
<211> LENGTH: 26
<212> TYPE: DNA
```

```
<213> ORGANISM: Artificial
<220> FEATURE:
<223> OTHER INFORMATION: Oligonucleotide

<400> SEQUENCE: 210
gtttctcgtg caataatttc tacatc                                          26

<210> SEQ ID NO 211
<211> LENGTH: 22
<212> TYPE: DNA
<213> ORGANISM: Artificial
<220> FEATURE:
<223> OTHER INFORMATION: Oligonucleotide

<400> SEQUENCE: 211
cgtatggatt ttgtccgttt ca                                              22

<210> SEQ ID NO 212
<211> LENGTH: 24
<212> TYPE: DNA
<213> ORGANISM: Artificial
<220> FEATURE:
<223> OTHER INFORMATION: Oligonucleotide

<400> SEQUENCE: 212
gaattgtgag cggataacaa tttc                                            24

<210> SEQ ID NO 213
<211> LENGTH: 17
<212> TYPE: DNA
<213> ORGANISM: Artificial
<220> FEATURE:
<223> OTHER INFORMATION: Oligonucleotide

<400> SEQUENCE: 213
ccagcggctt accatcc                                                    17

<210> SEQ ID NO 214
<211> LENGTH: 90
<212> TYPE: DNA
<213> ORGANISM: Artificial
<220> FEATURE:
<223> OTHER INFORMATION: Oligonucleotide

<400> SEQUENCE: 214
gcatcgtaaa gaacattttg aggcatttca gtcagttgct taatgtacct ataaccagac     60
cgttcagctg gatattacgg ccttttaaa                                       90

<210> SEQ ID NO 215
<211> LENGTH: 90
<212> TYPE: DNA
<213> ORGANISM: Artificial
<220> FEATURE:
<223> OTHER INFORMATION: Oligonucleotide

<400> SEQUENCE: 215
gcatcgtaaa gaacattttg aggcatttca gtcagttgct caatgtacct ataaccagac     60
cgttcagctg gatattacgg ccttttaaa                                       90

<210> SEQ ID NO 216
<211> LENGTH: 90
<212> TYPE: DNA
<213> ORGANISM: Artificial
<220> FEATURE:
<223> OTHER INFORMATION: Oligonucleotide
```

```
<400> SEQUENCE: 216
agcaagcacg ccttagtaac ccggaattgc gtaagtctgc cgctaaatcg tgatgctgcc    60
tttgaaaaaa ttaatgaagc gcgcagtcca                                    90

<210> SEQ ID NO 217
<211> LENGTH: 90
<212> TYPE: DNA
<213> ORGANISM: Artificial
<220> FEATURE:
<223> OTHER INFORMATION: Oligonucleotide

<400> SEQUENCE: 217
cagcaagcac gccttagtaa cccggaattg cgtaagtctg ccgccgatcg tgatgctgcc    60
tttgaaaaaa ttaatgaagc gcgcagtcca                                    90

<210> SEQ ID NO 218
<211> LENGTH: 90
<212> TYPE: DNA
<213> ORGANISM: Artificial
<220> FEATURE:
<223> OTHER INFORMATION: Oligonucleotide

<400> SEQUENCE: 218
tggactgcgc gcttcattaa ttttttcaaa ggcagcatca cgatcggcgg cagacttacg    60
caattccggg ttactaaggc gtgcttgctg                                    90

<210> SEQ ID NO 219
<211> LENGTH: 90
<212> TYPE: DNA
<213> ORGANISM: Artificial
<220> FEATURE:
<223> OTHER INFORMATION: Oligonucleotide

<400> SEQUENCE: 219
gccacatagc agaactttaa aagtgctcat cattggaaaa cgttattagg ggcgaaaact    60
ctcaaggatc ttaccgctgt tgagatccag                                    90

<210> SEQ ID NO 220
<211> LENGTH: 90
<212> TYPE: DNA
<213> ORGANISM: Artificial
<220> FEATURE:
<223> OTHER INFORMATION: Oligonucleotide

<400> SEQUENCE: 220
gccacatagc agaactttaa aagtgctcat cattggaaaa cgttcttcgg ggcgaaaact    60
ctcaaggatc ttaccgctgt tgagatccag                                    90

<210> SEQ ID NO 221
<211> LENGTH: 68
<212> TYPE: DNA
<213> ORGANISM: Artificial
<220> FEATURE:
<223> OTHER INFORMATION: Oligonucleotide

<400> SEQUENCE: 221
tgcttctcat gaacgataac acaacttgtt catgaattaa ccattccgga ttgaggcaca    60
ttaacgcc                                                            68

<210> SEQ ID NO 222
```

```
<211> LENGTH: 66
<212> TYPE: DNA
<213> ORGANISM: Artificial
<220> FEATURE:
<223> OTHER INFORMATION: Oligonucleotide

<400> SEQUENCE: 222
acggaaacca gccagttcct ttcgatgcct gaatttgatc ccatagttta tctagggcgg    60
cggatt                                                               66

<210> SEQ ID NO 223
<211> LENGTH: 19
<212> TYPE: DNA
<213> ORGANISM: Artificial
<220> FEATURE:
<223> OTHER INFORMATION: Oligonucleotide

<400> SEQUENCE: 223
gaacttgcac tacccatcg                                                 19

<210> SEQ ID NO 224
<211> LENGTH: 24
<212> TYPE: DNA
<213> ORGANISM: Artificial
<220> FEATURE:
<223> OTHER INFORMATION: Oligonucleotide

<400> SEQUENCE: 224
agtgacgggt taattatctg aaag                                           24

<210> SEQ ID NO 225
<211> LENGTH: 68
<212> TYPE: DNA
<213> ORGANISM: Artificial
<220> FEATURE:
<223> OTHER INFORMATION: Oligonucleotide

<400> SEQUENCE: 225
tttcatcttg ccagcatatt ggagcgtgat caattttgat cagctgtgaa cagccaggac    60
agaaatgc                                                             68

<210> SEQ ID NO 226
<211> LENGTH: 71
<212> TYPE: DNA
<213> ORGANISM: Artificial
<220> FEATURE:
<223> OTHER INFORMATION: Oligonucleotide

<400> SEQUENCE: 226
cattagcagt gatataacgt aagttttgt atcactacac atcagccccc tgcagaaata    60
aaaaggcctg c                                                         71

<210> SEQ ID NO 227
<211> LENGTH: 31
<212> TYPE: DNA
<213> ORGANISM: Artificial
<220> FEATURE:
<223> OTHER INFORMATION: Oligonucleotide

<400> SEQUENCE: 227 cattttgca ttactaataa gaaaaagcaa a                                    31

<210> SEQ ID NO 228
<211> LENGTH: 27
```

<212> TYPE: DNA
<213> ORGANISM: Artificial
<220> FEATURE:
<223> OTHER INFORMATION: Oligonucleotide

<400> SEQUENCE: 228
gtcctaatca ttcttgtaac atcctac                                27

<210> SEQ ID NO 229
<211> LENGTH: 73
<212> TYPE: DNA
<213> ORGANISM: Artificial
<220> FEATURE:
<223> OTHER INFORMATION: Oligonucleotide

<400> SEQUENCE: 229
tcaggttaaa atcatttaaa tttacacacg caacaaatat tgacctacaa ggtgttgaca   60
attaatcatc ggc                                               73

<210> SEQ ID NO 230
<211> LENGTH: 72
<212> TYPE: DNA
<213> ORGANISM: Artificial
<220> FEATURE:
<223> OTHER INFORMATION: Oligonucleotide

<400> SEQUENCE: 230
tttttactag tgagatagtc cagtttctga aaaatagcca gtgtaatgtt agcttgcaaa   60
ttaaagcctt cg                                                72

<210> SEQ ID NO 231
<211> LENGTH: 19
<212> TYPE: DNA
<213> ORGANISM: Artificial
<220> FEATURE:
<223> OTHER INFORMATION: Oligonucleotide

<400> SEQUENCE: 231
tcaggtaatc cgtttgcgg                                         19

<210> SEQ ID NO 232
<211> LENGTH: 21
<212> TYPE: DNA
<213> ORGANISM: Artificial
<220> FEATURE:
<223> OTHER INFORMATION: Oligonucleotide

<400> SEQUENCE: 232
aacggcagat tttttcactg c                                      21

<210> SEQ ID NO 233
<211> LENGTH: 67
<212> TYPE: DNA
<213> ORGANISM: Artificial
<220> FEATURE:
<223> OTHER INFORMATION: Oligonucleotide

<400> SEQUENCE: 233
tgaccatgat tacggattca ctggccgtcg ttttacaacg tcgtgcctgt gacggaagat   60
cacttcg                                                      67

<210> SEQ ID NO 234
<211> LENGTH: 67
<212> TYPE: DNA

```
<213> ORGANISM: Artificial
<220> FEATURE:
<223> OTHER INFORMATION: Oligonucleotide

<400> SEQUENCE: 234
gtgctgcaag gcgattaagt tgggtaacgc cagggttttc ccagtaacca gcaatagaca     60
taagcgg                                                              67

<210> SEQ ID NO 235
<211> LENGTH: 23
<212> TYPE: DNA
<213> ORGANISM: Artificial
<220> FEATURE:
<223> OTHER INFORMATION: Oligonucleotide

<400> SEQUENCE: 235
cgatggcgat tccggtttat tag                                            23

<210> SEQ ID NO 236
<211> LENGTH: 21
<212> TYPE: DNA
<213> ORGANISM: Artificial
<220> FEATURE:
<223> OTHER INFORMATION: Oligonucleotide

<400> SEQUENCE: 236
gctgccggat tatcatcaag a                                              21
```